(12) United States Patent
Chen et al.

(10) Patent No.: US 9,029,315 B2
(45) Date of Patent: May 12, 2015

(54) SOLUBLE PD-1 VARIANTS, FUSION CONSTRUCTS, AND USES THEREOF

(75) Inventors: Zhiwei Chen, Hong Kong (CN); Jingying Zhou, Hong Kong (CN)

(73) Assignee: The University of Hong Kong, Hong Kong (CN)

( * ) Notice: Subject to any disclaimer, the term of this patent is extended or adjusted under 35 U.S.C. 154(b) by 374 days.

(21) Appl. No.: 13/294,306

(22) Filed: Nov. 11, 2011

(65) Prior Publication Data
US 2012/0121634 A1    May 17, 2012

Related U.S. Application Data

(60) Provisional application No. 61/412,557, filed on Nov. 11, 2010.

(51) Int. Cl.
*A01N 61/00* (2006.01)
*A61K 38/00* (2006.01)
*A61K 38/16* (2006.01)
*C07K 14/705* (2006.01)
*A61K 39/21* (2006.01)
*C07K 14/005* (2006.01)
*A61K 39/00* (2006.01)

(52) U.S. Cl.
CPC ........... *C07K 14/70521* (2013.01); *A61K 39/21* (2013.01); *A61K 2039/53* (2013.01); *C07K 2319/00* (2013.01); *C07K 2319/30* (2013.01); *C07K 2319/32* (2013.01); *C07K 2319/33* (2013.01); *C12N 2740/16034* (2013.01); *C07K 14/005* (2013.01); *C12N 2740/16222* (2013.01)

(58) Field of Classification Search
None
See application file for complete search history.

(56) References Cited

U.S. PATENT DOCUMENTS

2012/0213780 A1*    8/2012    Zhu et al. ............... C12N 1/19

* cited by examiner

*Primary Examiner* — Louise Humphrey
*Assistant Examiner* — Stuart W Snyder
(74) *Attorney, Agent, or Firm* — Saliwanchik, Lloyd & Eisenschenk

(57) ABSTRACT

The subject invention provides novel soluble PD-1 (sPD-1) proteins, nucleic acids, and fusion constructs thereof, for enhancing humoral and cell-mediated immunity of a subject. Also provided are therapeutic compositions comprising the sPD-1 proteins, nucleic acids, and fusion constructs of the subject invention. In a preferred embodiment, the therapeutic composition is formulated as a vaccine composition. Advantageously, the sPD-1 proteins, nucleic acids, and therapeutic compositions provide protective immunity against pathogenic infection including HIV infection. In addition, the subject invention can be used in the prevention and/or treatment of tumor or cancer.

4 Claims, 36 Drawing Sheets

FIG. 1A

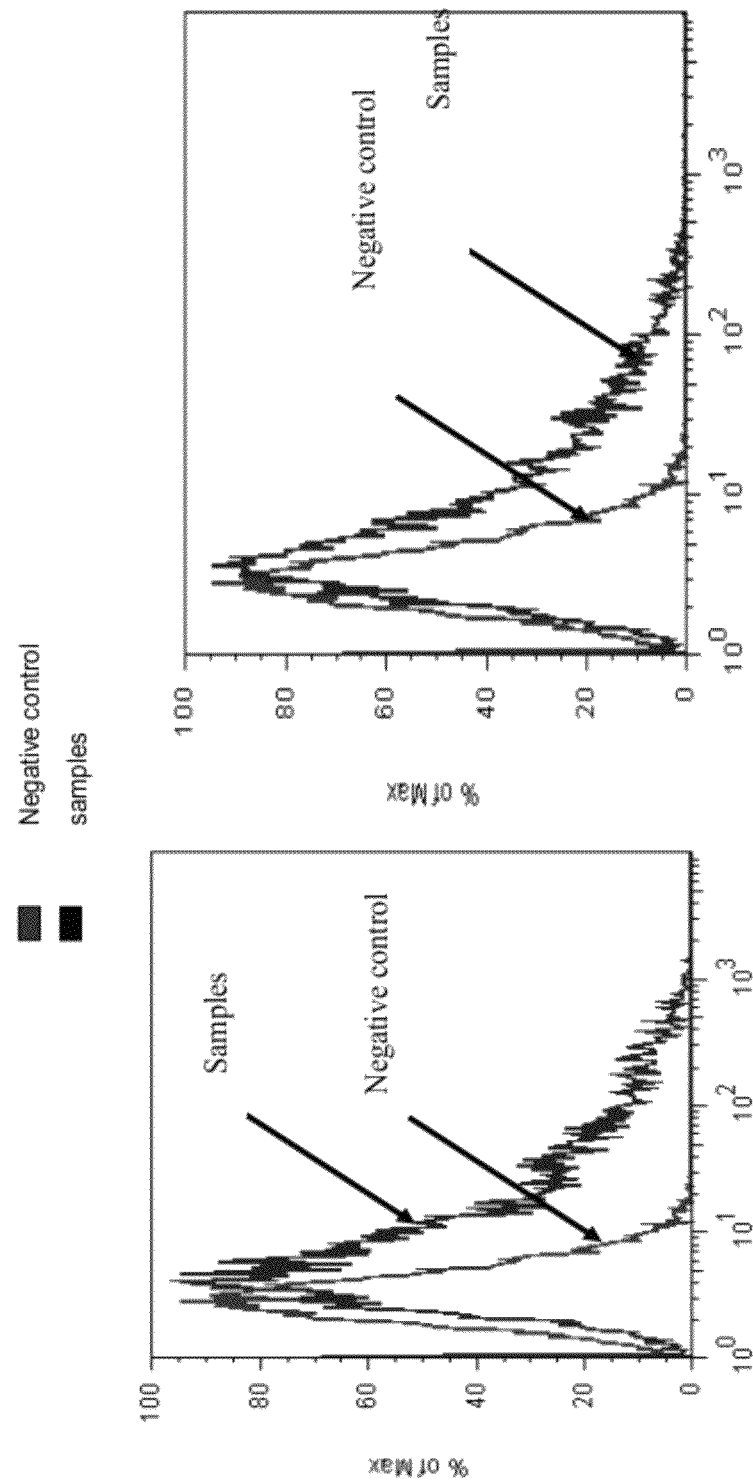

SEQ ID NO: 19 mspd1-p24-fc
SEQ ID NO: 13 mspd1-14del-p24-fc
SEQ ID NO: 17 mspd1-322mu-p24-fc
SEQ ID NO: 3  p24-fc

```
                     10        20        30        40        50        60        70        80        90       100
                      |         |         |         |         |         |         |         |         |         |
mspd1-p24-fc         MWVRQVPWSFTWAVLQLSWQSGWLLEVPNGPWRSLIFEAAWLITVSEGANAFTCSLSNWSEDLMLNWNRLSPSNQTEKQAAFCNGLSQPVQDAREQIIQL
mspd1-14del-p24-fc   ..................................----------........................................................
mspd1-322mu-p24-fc   ....................................................................................................
p24-fc               ----------------------------------------------------------------------------------------------------

110       120       130       140       150       160       170       180       190       200
                      |         |         |         |         |         |         |         |         |         |
mspd1-p24-fc         PNRHDPHMNALDTRRNDSGIYLCAISLHPKAKIEESPGAELVVTERILETSTRYPSPSPKPEGEQPEFRCGGSGGCPIVQNLQGGMVHQPISPRTLNA
mspd1-14del-p24-fc   ....................................................................................................
mspd1-322mu-p24-fc   ........V...........................................................................................
p24-fc               ----------------------------------------------------------------------------------------------------

210       220       230       240       250       260       270       280       290       300
                      |         |         |         |         |         |         |         |         |         |
mspd1-p24-fc         WVKVIEEKAFSPEVIPMFSALSEAATPQDLNTMLNTVGGHQAAMQMLKETINEEAAEWDRLHPVQAGPVAPGQMREPRGSDIAGTTSNLQEQIGWMTNNP
mspd1-14del-p24-fc   ....................................................................................................
mspd1-322mu-p24-fc   ....................................................................................................
p24-fc               ----------------------------------------------------------------------------------------------------

310       320       330       340       350       360       370       380       390       400
                      |         |         |         |         |         |         |         |         |         |
mspd1-p24-fc         PIPVGEIYKRWIILGLNKIVRMYSPTSILDIRQGPKEPFRDYVDRFYKTLR.EQASQEVKNWMTETLLVQNSNPDCKTIIKALGPAATLEEMMTACQGVG
mspd1-14del-p24-fc   ....................................................................................................
mspd1-322mu-p24-fc   ....................................................................................................
p24-fc               ----------------------------------------------------------------------------------------------------

410       420       430       440       450       460       470       480       490       500
                      |         |         |         |         |         |         |         |         |         |
mspd1-p24-fc         GPGHKARVLMQYIKANSKEIGITELKKLGGSNDIFNNPTVSFWLRVPKVSASHLEQYIEATNTKVDKTVAPSTCSKPMCEPPELLGGPSVFIFPPKPKDT
mspd1-14del-p24-fc   ....................................................................................................
mspd1-322mu-p24-fc   ....................................................................................................
p24-fc               ----------------------------------------------------------------------------------------------------

510       520       530       540       550       560       570       580       590       600
                      |         |         |         |         |         |         |         |         |         |
mspd1-p24-fc         LMISRTPEVTCVVVDVSQDDPEVQFSTWYINNEQVRTARPPLREQQFNSTIRVVSTLPIAHQDWLRGKEFKCKVHNKALPAPIEKTISKARGQPLEPKVYT
mspd1-14del-p24-fc   ....................................................................................................
mspd1-322mu-p24-fc   ....................................................................................................
p24-fc               ----------------------------------------------------------------------------------------------------

610       620       630       640       650       660       670       680       690
                      |         |         |         |         |         |         |         |         |
mspd1-p24-fc         MGPPREELSSRSVSLTCMINGFYPSDISVEWEKNGKAEDNYKTTPTVLDSDGSYFLYSKLSVPTSEWQRGDVTCSVMHEALHNHYTQKSISHSPGK
mspd1-14del-p24-fc   ..............................................................................................
mspd1-322mu-p24-fc   ..............................................................................................
p24-fc               ----------------------------------------------------------------------------------------------------
```

FIG. 7A

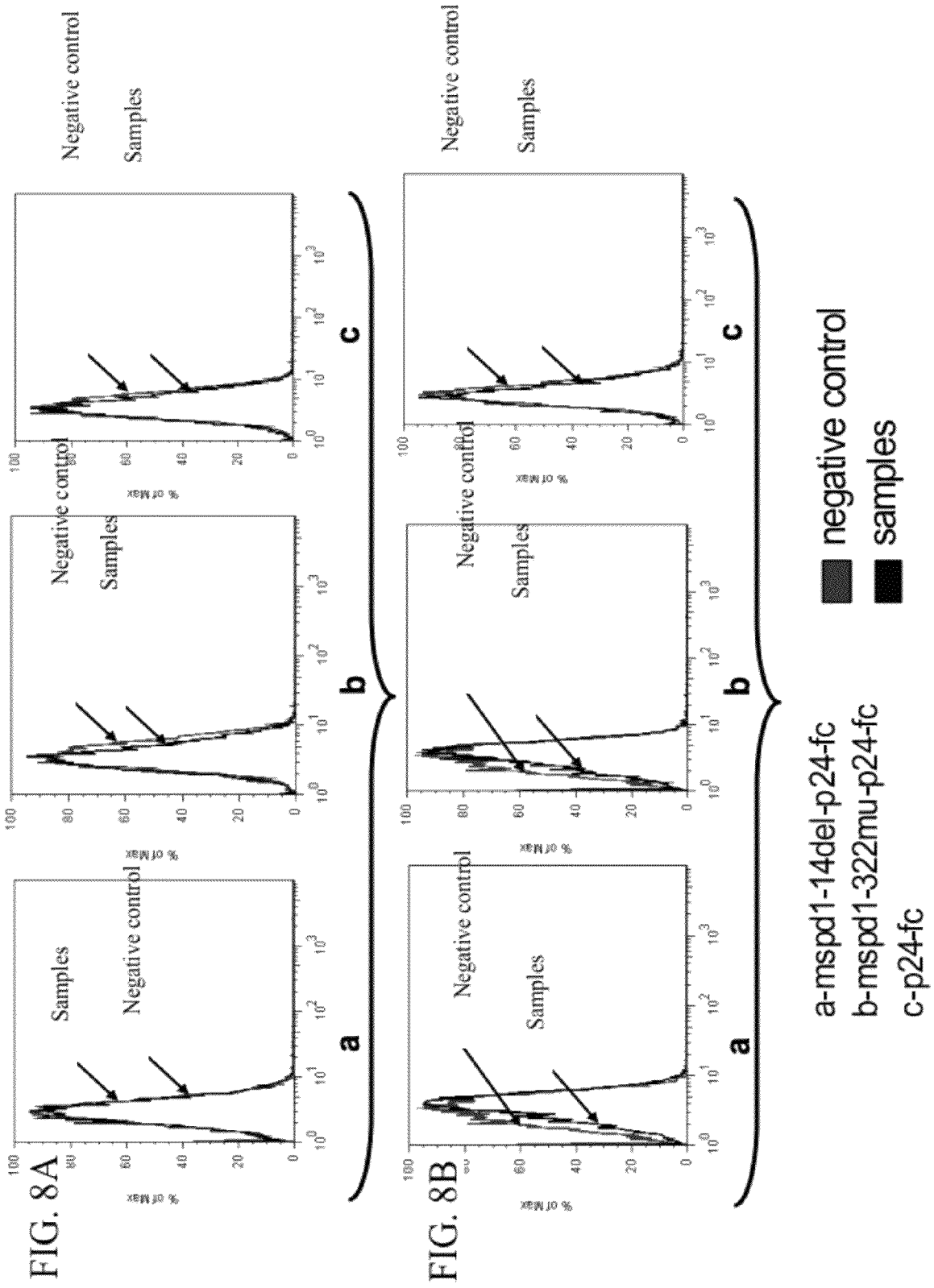

negative
sample

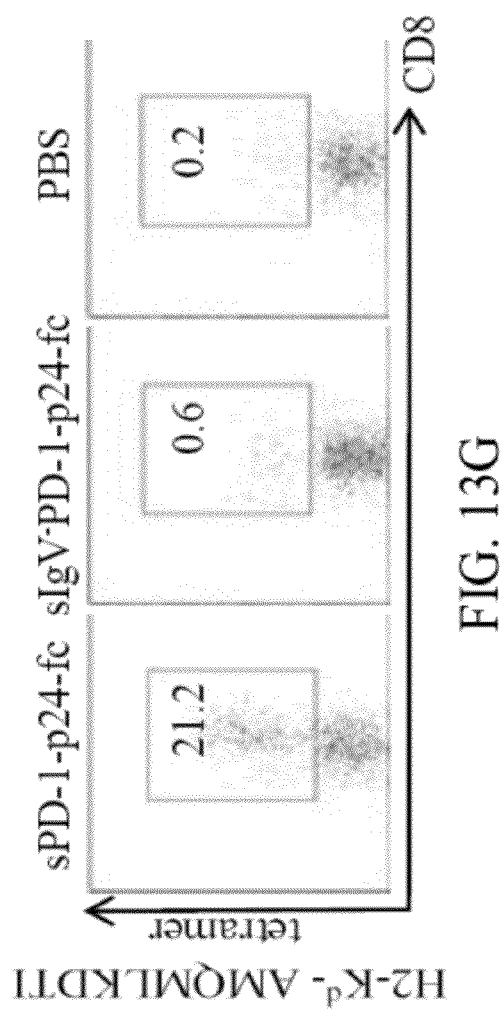
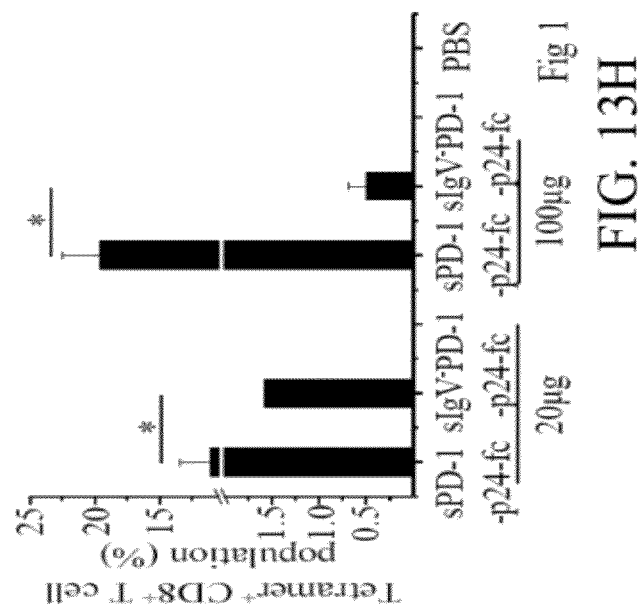
FIG. 13G
FIG. 13H

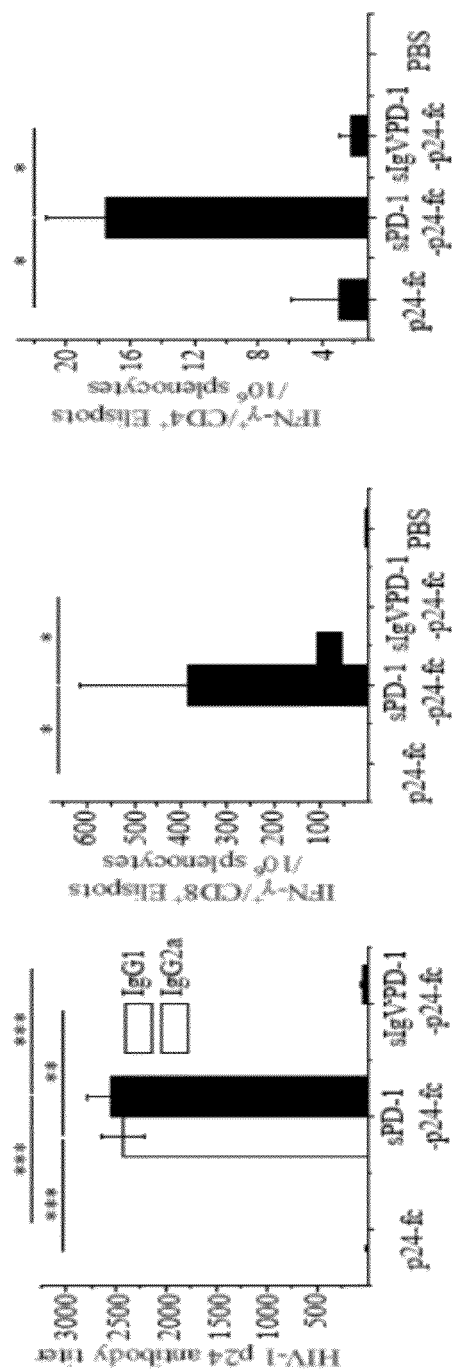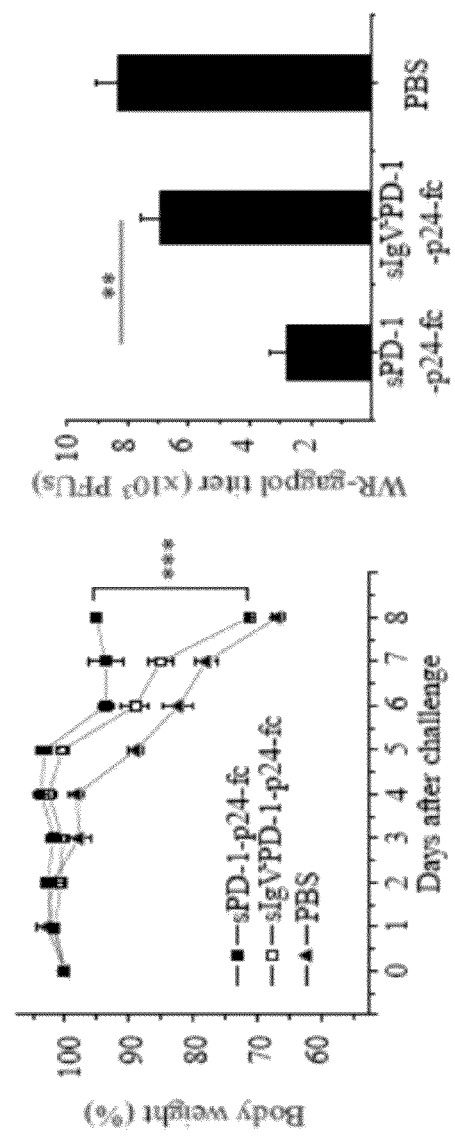
FIG. 15A  FIG. 15B  FIG. 15C  FIG. 15D  FIG. 15E

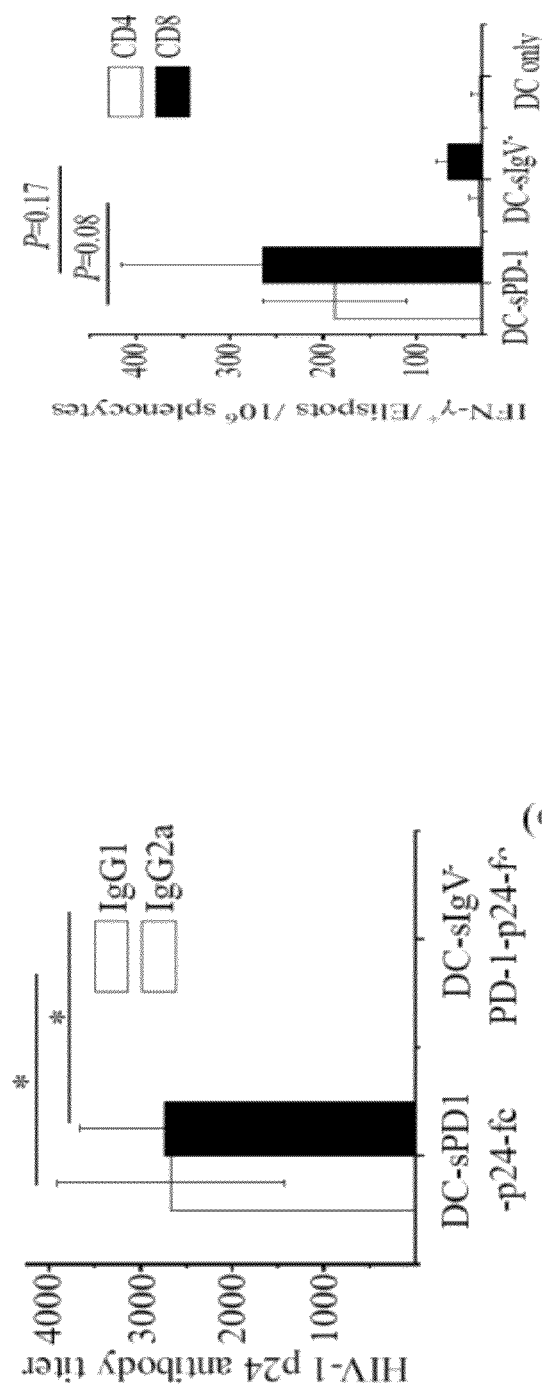
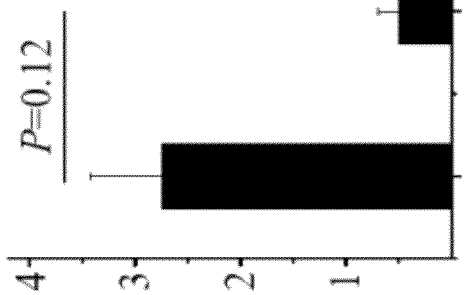
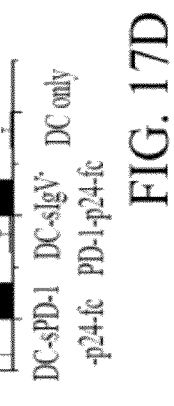
FIG. 17C
FIG. 17D
FIG. 17E

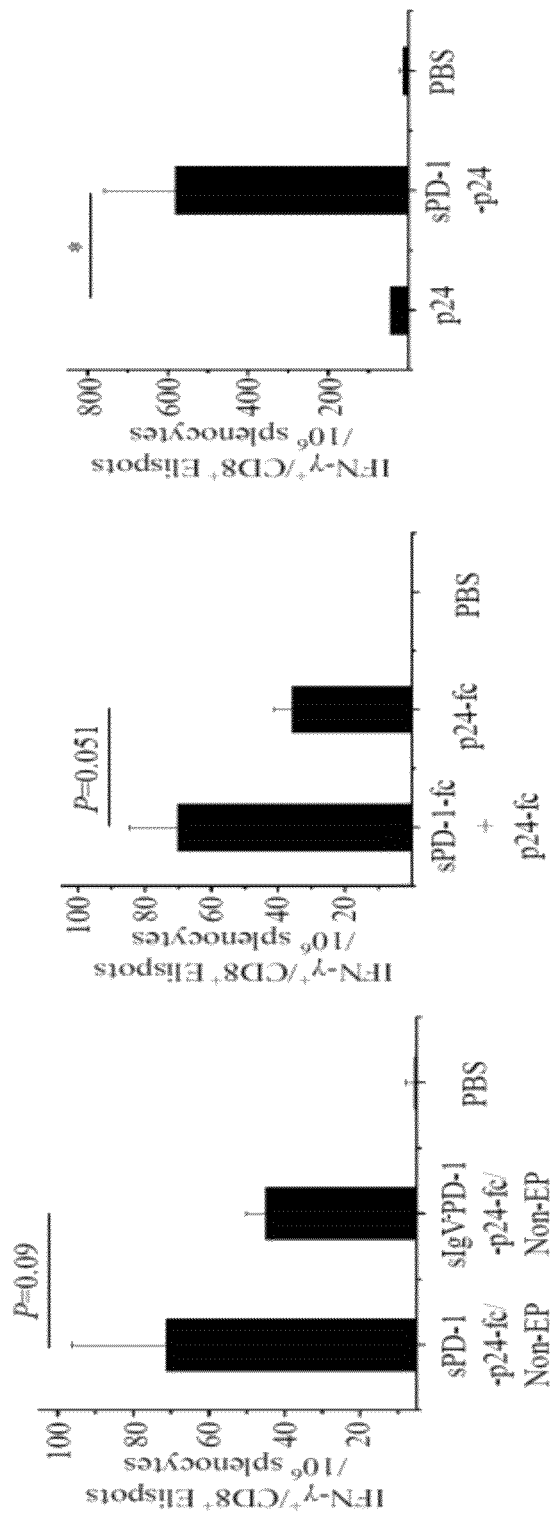

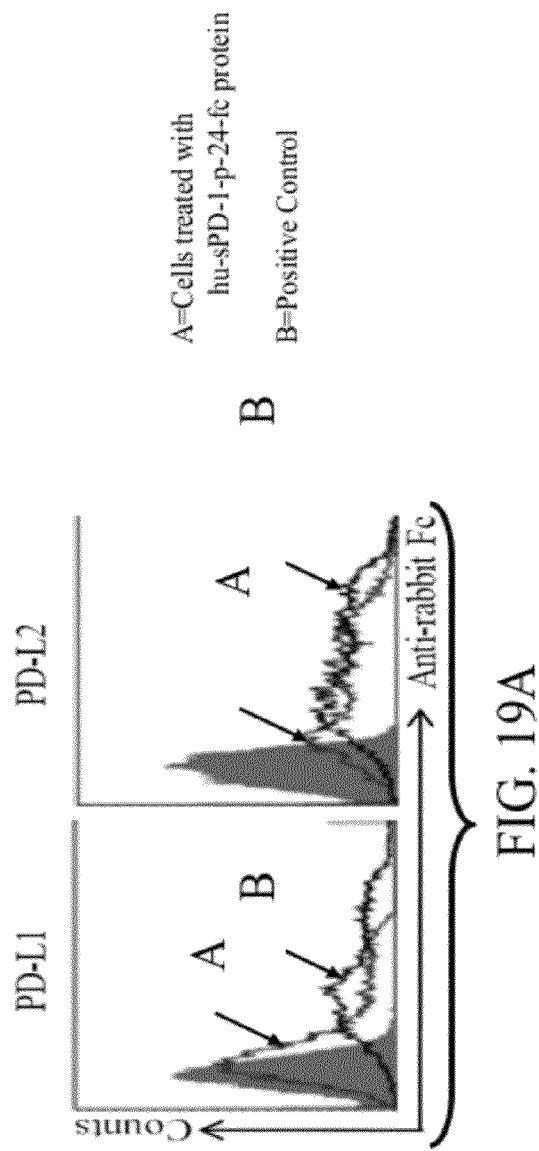
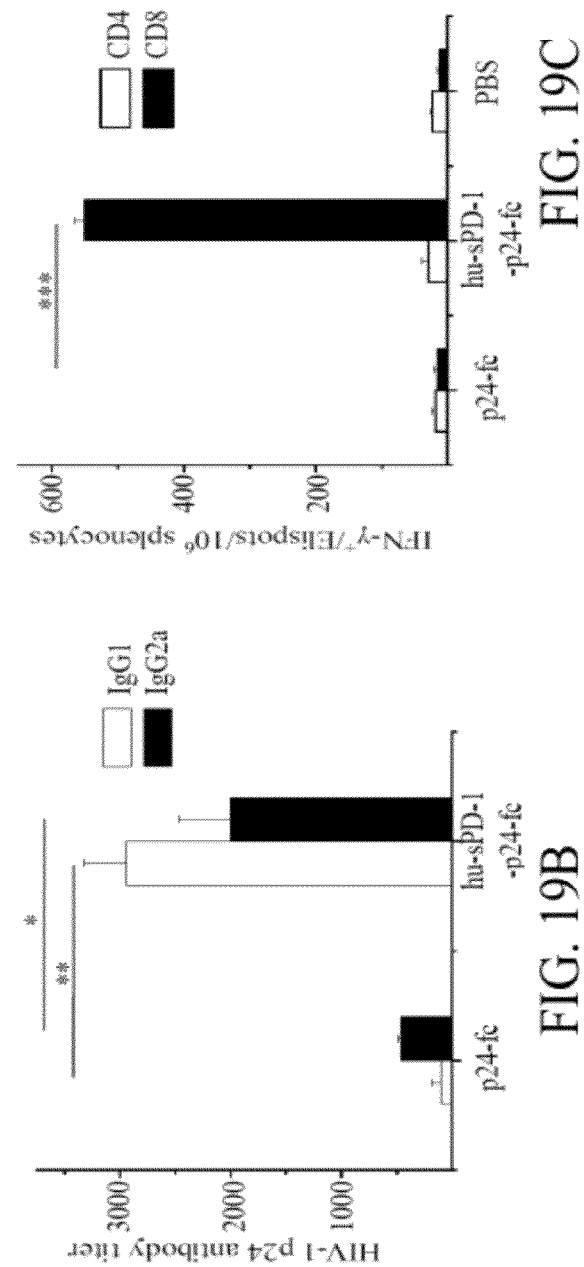
FIG. 19A
FIG. 19B
FIG. 19C

SOLUBLE PD-1 VARIANTS, FUSION CONSTRUCTS, AND USES THEREOF

CROSS-REFERENCE TO RELATED APPLICATION

This application claims the benefit of U.S. provisional application Ser. No. 61/412,557, filed Nov. 11, 2010, which is herein incorporated by reference in its entirety.

BACKGROUND OF THE INVENTION

Programmed death 1 (PD-1), expressed primarily on T cells, is a receptor for B7-H1 molecule (also known as programmed death ligand 1 (PD-L1)) and B7-DC molecule (also known as programmed death ligand 2 (PD-L2)). PD-L1 is expressed on many different cell types, whereas PD-L2 is expressed only on antigen-presenting cells such as B cells, dendritic cells and macrophages.

The PD-1/PD-L pathway, which transmits negative signals to immune cells, plays a critical role in the modulation of immune responses during infection and cancer. The interaction of PD-1 with PD-L1/L2 inhibits T cell function during HIV infection. A recent study suggested that the blockade of PD-1 during chronic simian immunodeficiency virus (SIV) infection by anti PD-1 antibody resulted in enhanced B cell responses as well as rapid expansion and restoration of SIV-specific polyfunctional CD8 T cells. Other studies suggested that the blockade of the PD-1/PD-L pathway facilitates the restoration of humoral and cell-mediated immune responses during LCMV and HBV infection.

Human immunodeficiency virus type I (HIV-1) has contributed to an estimated 25 million deaths since it was first recognized in 1981. Currently, over 33 million people worldwide are living with the virus. One of the existing HIV vaccine compositions, obtained by fusing HIV-1 p24 to DEC-205 antibody, enhances CD4 T cell immune responses and cytokine release. In addition, this vaccine composition confers protection against vaccinia-gag viral challenge. However, this HIV vaccine composition does not improve Th1 CD8 T cell response. Thus, improved HIV-1 vaccine compositions that enhance host immunity and protect against HIV infection are needed. As will be clear from the disclosure that follows, these and other benefits are provided by the present invention.

BRIEF SUMMARY OF THE INVENTION

The subject invention provides soluble PD-1 (sPD-1) proteins and nucleic acids, and therapeutic compositions comprising sPD-1 proteins and nucleic acids, for enhancing immunity of a subject. In one embodiment, the sPD-1 proteins, nucleic acids, and compositions are formulated as a vaccine composition.

One aspect of the subject invention provides sPD-1 protein variants. In an embodiment, the sPD-1 protein variant is mspd1-14del, which has an amino acid sequence comprising SEQ ID NO: 11. In an embodiment, the sPD-1 protein variant is mspd1-322 mu, which has an amino acid sequence comprising SEQ ID NO: 15. In an embodiment, the sPD-1 protein variant is hspd1-14del, which was found in healthy Chinese people. The hspd1-14del variant has an amino acid sequence comprising SEQ ID NO: 25.

Another aspect of the invention provides nucleic acid molecules that encode the sPD-1 proteins of the subject invention. In an embodiment, the nucleic acid molecule encodes mspd1-14del, and has a sequence comprising SEQ ID NO: 12. In an embodiment, the nucleic acid molecule encodes mspd1-322mu, and has a sequence comprising SEQ ID NO: 16. In an embodiment, the nucleic acid molecule encodes hspd1-14del, and has a sequence comprising SEQ ID NO: 26.

In addition, the subject invention provides sPD-1 fusion proteins. In specific embodiments, the subject sPD-1 fusion protein comprises SEQ ID NO: 13, SEQ ID NO: 17, SEQ ID NO: 19, SEQ ID NO: 23, or SEQ ID NO: 27. The subject invention also provides sPD-1 fusion nucleic acid molecules. In specific embodiments, the subject sPD-1 fusion DNA comprises SEQ ID NO: 14, SEQ ID NO: 18, SEQ ID NO: 20, SEQ ID NO: 24, or SEQ ID NO: 28.

Another aspect of the subject invention provides methods for the prevention and/or treatment of pathogenic infection, cancer or tumor, and other diseases in which induction of antigen-specific protective immunity would be beneficial. Advantageously, the methods of the subject invention enhance host humoral and cell-mediated immunity. The method comprises administering to a subject in need of such treatment an effective amount of a fusion protein or fusion nucleic acid molecule of the subject invention. In a preferred embodiment, the subject method can be used in the prevention and treatment of HIV or other pathogen infection. In addition, the methods can be used in the prevention and/or treatment of tumor or cancer.

The subject invention further provides for therapeutic or pharmaceutical compositions. In an embodiment, the composition comprises a therapeutically effective amount of a protein and/or nucleic acid molecule of the subject invention and, optionally, a pharmaceutically acceptable carrier. In a preferred embodiment, the therapeutic composition is a vaccine composition.

BRIEF DESCRIPTION OF THE DRAWINGS

Figure 1A:
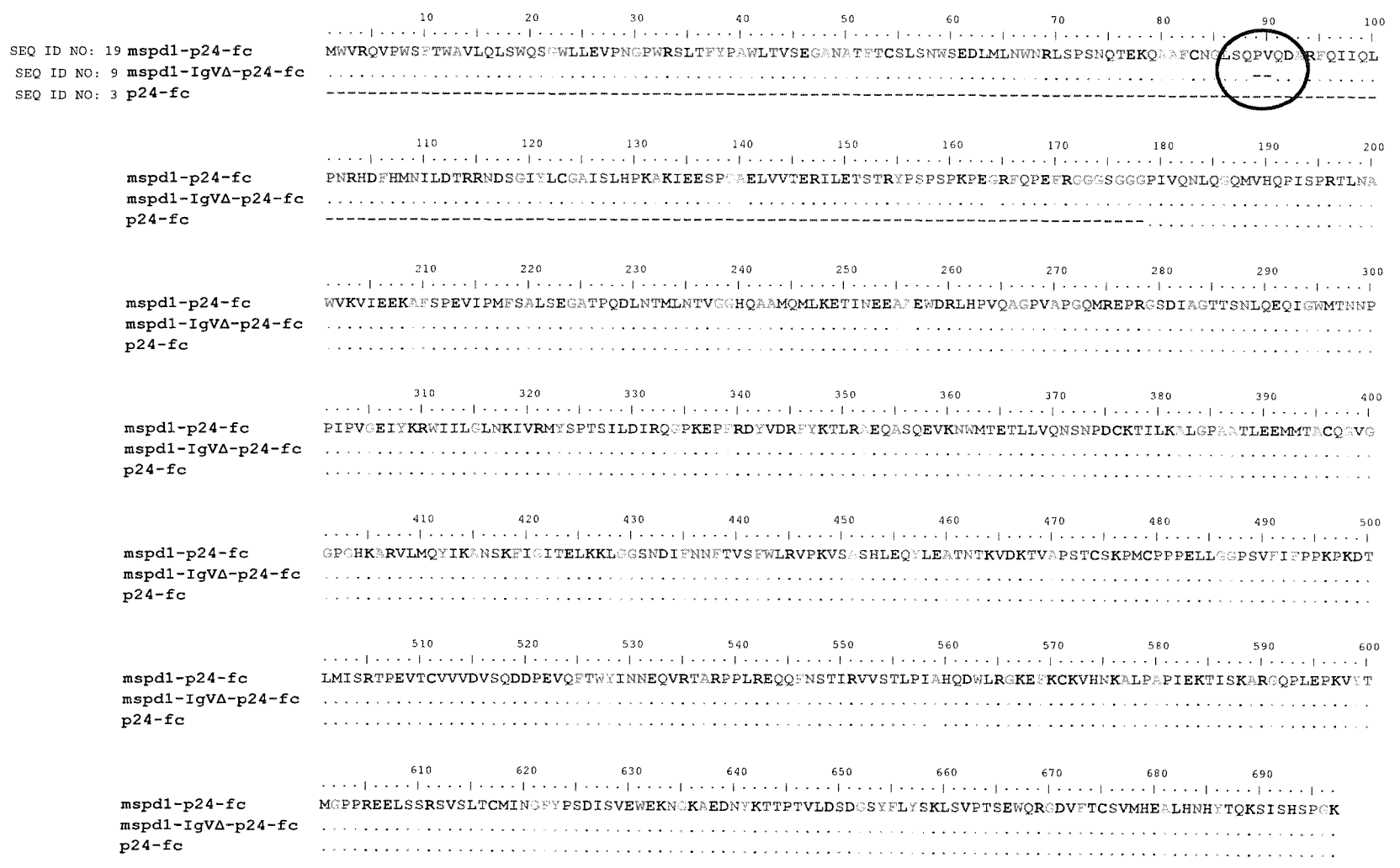

FIG. 1A shows alignment of amino acid sequences of mspd1-p24-Fc, mspd1-IgVΔ-p24-Fc and p24-Fc fusion proteins.

FIG. 7A shows alignment of amino acid sequences of mspd1-p24-Fc, mspd1-14del-p24-Fc, mspd1-322mu-p24-Fc, and p24-fc fusion proteins.

FIG. 8 shows the binding ability of mspd1-14del-p24-Fc, mspd1-322mu-p24-Fc, and p24-fc fusion proteins to sPD-1 ligands, respectively. (A) shows the binding ability of mspd1-14del-p24-Fc, mspd1-322mu-p24-Fc, and p24-Fc fusion proteins to PD-L1, respectively. (B) shows the binding ability of mspd1-14del-p24-Fc, mspd1-322mu-p24-Fc, and p24-Fc fusion proteins to PD-L2, respectively.

FIG. 15 shows that vaccination with sPD-1-p24-fc induces specific long lasting and protective immunity. Sera and splenocytes derived from mice 30 weeks after immunization were isolated and examined for antibody and CD8⁺ and CD4⁺ T cell responses. (A) Specific IgG1 and IgG2a antibodies against HIV-1 Gag p24 detected by ELISA. ELISpot assays using specific HIV-1 Gag p24 epitope for (B) CD8⁺ T cells and (C) CD4⁺ T cells was performed to test the ability of T cells to produce IFN-γ. Mice previously immunized with a dose of 100 μg DNA vaccines were challenged with 2×10⁵ PFUs of virulent WRgagpol three weeks post immunization to examine immune protection. Each group contained up to 5 mice. (D) Immunized mice were weighed daily for eight days after vaccinia challenge. (E) Virus titers in the lungs of immunized mice were evaluated by plaque formation on Vero cell monolayers.

FIG. 18 characterizes sPD-1-p24-fc DNA vaccination. CD8⁺ T cell ELISpot assay of immunization strategy by i.m. (A) without electroporation (EP), (B) with purified p24-fc and/or sPD-1-fc with EP, or (c) using DNA vaccines without rabbit Fc tag with EP. All data points represent the mean±standard error as error bars. *P<0.05.

FIG. 19 shows that human sPD-1-p24-fc elicits similar p24-specific immunity in mice. (A) Binding profiles of hu-sPD-1-p24-fc protein to murine PD-1 ligands transiently expressed on 293T cells. Flow cytometric signals were obtained by treating the cells with husPD-1-p24-fc protein followed by anti-rabbit Fc-FITC antibody for detection. Controls included transfected 293T cells stained with anti-rabbit Fc-FITC antibody (negative, shaded) or anti-mouse PD-L1- or L2-FITC antibodies (positive, solid line, not shaded). Balb/c mice were immunized with hu-sPD-1-p24-fc and p24-fc at a dose of 20 μg i.m./EP, or received PBS only serving as a negative control. (B) Detection of specific IgG1 and IgG2a antibodies against HIV-1 Gag p24 by ELISA two weeks post immunization in mice sera. (C) Frequencies of IFN-γ-secreting CD8+ and CD4+ T cells in mice splenocytes measured by ELISpot assay in specific response to HIV-1 Gag p24 epitopes specific for CD4+ and CD8+ T cells, respectively. Columns represent the mean values of three replicate mice with standard error as error bars. Data are representative of two independent immunization experiments. *P<0.05, P<0.01, *P<0.001.

BRIEF DESCRIPTION OF THE SEQUENCES

Figure 1B:
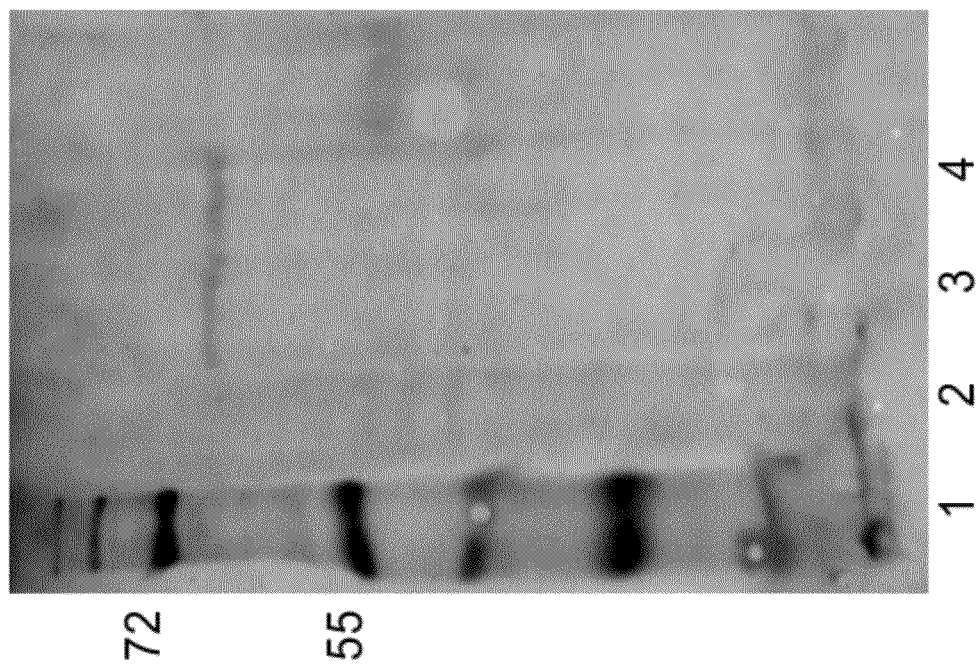
FIG. 1B shows Western blot analysis of mspd1-p24-Fc, mspd1-IgVΔ-p24-Fc and p24-Fc. Proteins are detected by anti-rabbit Fc antibody.

SEQ ID NO: 1 is an amino acid sequence of the wild-type soluble extracellular domain of mouse PD-1 (mouse spd1).

SEQ ID NO: 2 is a nucleic acid sequence of the wild-type mouse spd1 DNA.

SEQ ID NO: 3 is an amino acid sequence of HIV p24 useful according to the subject invention.

SEQ ID NO: 4 is a nucleic acid sequence of HIV p24 DNA useful according to the subject invention.

SEQ ID NO: 5 is an amino acid sequence of rabbit Fc domain useful to the subject invention.

SEQ ID NO: 6 is a nucleic acid sequence of rabbit Fc DNA useful to the subject invention.

SEQ ID NO: 7 is an amino acid sequence of mspd1-IgVΔ

SEQ ID NO: 8 is a nucleic acid sequence of mspd1-IgVΔ DNA.

SEQ ID NO: 9 is an amino acid sequence of mspd1-IgVΔ-p24-Fc fusion protein.

SEQ ID NO: 10 is a nucleic acid sequence of mspd1-IgVΔ-p24-Fc fusion DNA.

SEQ ID NO: 11 is an amino acid sequence of mspd1-14del.

SEQ ID NO: 12 is a nucleic acid sequence of mspd1-14del DNA.

SEQ ID NO: 13 is an amino acid sequence of mspd1-14del-p24-Fc fusion protein.

SEQ ID NO: 14 is a nucleic acid sequence of mspd1-14del-p24-Fc fusion DNA.

SEQ ID NO: 15 is an amino acid sequence of mspd1-322mu.

SEQ ID NO: 16 is a nucleic acid sequence of mspd1-322mu DNA.

SEQ ID NO: 17 is an amino acid sequence of mspd1-322mu-p24-Fc fusion protein.

SEQ ID NO: 18 is a nucleic acid sequence of mspd1-322mu-p24-Fc fusion DNA.

SEQ ID NO: 19 is an amino acid sequence of mspd1-p24-Fc fusion protein.

SEQ ID NO: 20 is a nucleic acid sequence of mspd1-p24-Fc fusion DNA.

SEQ ID NO: 21 is an amino acid sequence of the wild-type soluble extracellular domain of human PD-1 (human spd1).

SEQ ID NO: 22 is a nucleic acid sequence of the wild-type human spd1 DNA.

SEQ ID NO: 23 is an amino acid sequence of hspd1-p24-Fc fusion protein.

SEQ ID NO: 24 is a nucleic acid sequence of hspd1-p24-Fc fusion DNA.

SEQ ID NO: 25 is an amino acid sequence of hspd1-14del.

SEQ ID NO: 26 is a nucleic acid sequence of hspd1-14del DNA.

SEQ ID NO: 27 is an amino acid sequence of hspd1-14del-p24-Fc fusion protein.

SEQ ID NO: 28 is a nucleic acid sequence of hspd1-14del-p24-Fc fusion DNA.

SEQ ID NO: 29 is an amino acid sequence of a linker sequence useful according to the subject invention.

SEQ ID NO: 30 is an amino acid sequence of a linker sequence useful according to the subject invention.

SEQ ID NO: 31 is an amino acid sequence of a linker sequence useful according to the subject invention.

SEQ ID NO: 32 is an amino acid sequence of a linker sequence useful according to the subject invention.

SEQ ID NO: 33 is an amino acid sequence of a linker sequence useful according to the subject invention.

SEQ ID NO: 34 is an amino acid sequence of a linker sequence useful according to the subject invention.

SEQ ID NO: 35 is an amino acid sequence of a linker sequence useful according to the subject invention.

SEQ ID NO: 36 is an amino acid sequence of a linker sequence useful according to the subject invention.

SEQ ID NO: 37 is an amino acid sequence of a linker sequence useful according to the subject invention.

SEQ ID NO: 38 is an amino acid sequence of a linker sequence useful according to the subject invention.

SEQ ID NO: 39 is an amino acid sequence useful according the subject invention.

SEQ ID NO: 40 is an amino acid sequence useful according the subject invention.

DETAILED DISCLOSURE OF THE INVENTION

The subject invention provides soluble PD-1 (sPD-1) proteins and nucleic acids, and therapeutic compositions comprising soluble PD-1 proteins and nucleic acids, useful for inducing antigen-specific protective immunity against infection and cancer. In one embodiment, the subject sPD-1 proteins, nucleic acids, and compositions are formulated as a vaccine composition. In an embodiment, the subject invention provides novel fusion proteins mspd1-p24Fc, mspd1-14del-p24Fc, mspd1-322mu-p24Fc, and hspd1-14del-p24Fc, and nucleic acid molecules encoding these fusion proteins.

The subject invention is based on the findings that the immune regulatory PD-1/PD-L pathway down-regulates HIV-1-specific CD8+ T cells responses. The present inventors discovered a natural variant of PD-1 present in healthy people that does not interact with either PD-L1 or PD-L2 (the ligands of PD-1). In addition, a point mutation, which is essential for PD-1 and its ligands interaction, is discovered.

In one embodiment, the subject invention provides a novel DNA vaccine design that mimics the binding of programmed death-1 (PD-1) to its ligands expressed on dendritic cells (DCs) for functional activation, by fusing soluble PD-1 with an antigen of interest. Intramuscular immunization via electroporation (EP) of the fusion DNA vaccine elicited robust anti-Gag antibody titers in mice, with both IgG1 (Th2) and IgG2a (Th1) responses detected. High frequencies of Gag-specific, broadly reactive and polyfunctional T cells, especially CD8+ T cells were elicited following immunization. These responses were dose-dependent, long lasting and conferred protection against intranasal challenge with virulent vaccinia-Gag virus. Specifically, mspd-p24fc, mspd1-14del-p24fc and mspd1-322mu-p24fc enhance HIV-1 Gag-specific immune responses, as determined by the number of IFN-γ expressed CD4 and CD8 T cells using Elispot assays. Thus, soluble PD-1-based DNA/EP vaccination of the subject invention offers an easy, repeatable and effective way to induce durable and protective CD8+ cell immunity, which has important implications for vaccine development and gene therapy.

In one embodiment, the mspd1-14del protein variant is obtained by deleting amino acids 26-39 of the wild-type mspd1 (Amino acids 26-39 are the first 14 amino acids encoded by the second exon of the wild-type mouse PD-1 gene. These 14 amino acids of mspd1 have the same sequence as the first 14 amino acids encoded by the second exon of the human hspd1-14del homologue). The mspd1-322mu protein variant is obtained by changing amino acid residue 108 of the wild-type PD-1 protein from Met to Val. The hspd1-14del variant, which is derived from a natural isoform of human PD-1, has a deletion of amino acids 26-39 of the wild-type hspd1 (encoded by the first part of the second exon of the wild-type human PD-1 gene).

The mspd1-p24Fc fusion protein binds to PD-1 ligands PD-L1 and PD-L2, and the binding of PD-1 to PD-L can be blocked by anti-PD-L1/L2 antibodies. It is postulated that the binding of mspd1-p24Fc fusion protein inhibits the PD-1/PD-L pathway, which transmits negative signals to immune cells. In comparison, none of mspd1-14del-p24Fc, mspd1-322mu-p24Fc, and hspd1-14del-p24Fc fusion proteins binds to PD-L1 or PD-L2. This indicates that amino acid residues 26-39 encoded by DNA in exon 2 of spd1 and amino acid residue 108 Met of mspd1 are important for PD-L binding.

Advantageously, the administration of mspd1-p24Fc, mspd1-14del-p24Fc, mspd1-322mu-p24Fc, and hspd1-14del-p24Fc fusion proteins, or fusion DNA thereof, enhanced HIV-1 Gag-specific immune responses. As shown in FIGS. 3-6 and 8-11, administration of mspd1-p24Fc, mspd1-14del-p24Fc, mspd1-322mu-p24Fc, and hspd1-14del-p24Fc DNA significantly increased anti-p24 IgG1 (Th2) and IgG2a (Th1) antibody titers. In addition, the administration of mspd1-p24Fc, mspd1-14del-p24Fc, mspd1-322mu-p24Fc, and hspd1-14del-p24Fc DNA also significantly increased the number of IFN-γ-expressing CD4 and CD8 T cells in mice. Specifically, mice immunized mspd1-p24Fc, mspd1-14del-p24Fc, or mspd1-322mu-p24Fc DNA had significantly reduced titers of challenge virus upon vaccinia virus-gagpol (VTT-gagpol) challenges.

In comparison, mspd1-IgVΔ-p24-Fc, which is obtained by deleting amino acids 89-90 of the mouse PD-1 protein, does not bind to PD-1 ligands PD-L1 and PD-L2. In addition, the administration of mspd1-IgVΔ-p24-Fc DNA does not enhance humoral or cell-mediated immunity in mice. Further, the administration of mspd1-IgVΔ-p24-Fc DNA does not reduce HIV viral titers upon vaccinia virus-gagpol (MVTT-gagpol) challenges.

PD-1 Variants and Fusion Constructs

A first aspect of the subject invention provides sPD-1 protein variants. In one embodiment, the sPD-1 protein variant is obtained by deleting amino acid residues 26-39 of a wild-type sPD-1 protein. The wild-type sPD-1 protein is preferably of mammalian origin (such as a wild-type mouse, rabbit, non-human primates, or pig PD-1 protein), more preferably, of human origin.

In an embodiment, the sPD-1 protein variant is mspd1-14del, which has an amino acid sequence comprising SEQ ID NO: 11. In an embodiment, the sPD-1 protein variant is mspd1-322mu, which has an amino acid sequence comprising SEQ ID NO: 15. In an embodiment, the sPD-1 protein variant is hspd1-14del, which has an amino acid sequence comprising SEQ ID NO: 25.

In certain embodiments, the subject invention encompasses PD-1 protein variants that are homologous to mspd1-14del (SEQ ID NO: 11), mspd1-322mu (SEQ ID NO: 15), or hspd1-14del (SEQ ID NO: 25). In an embodiment, the sPD-1 protein variant has an amino acid sequence that is at least about 95%, 96%, 97%, 98%, 99%, or 99.5% identical to SEQ ID NO: 11. In an embodiment, the sPD-1 protein variant has an amino acid sequence that is at least about 95%, 96%, 97%, 98%, 99%, or 99.5% identical to SEQ ID NO: 15. In an embodiment, the sPD-1 protein variant has an amino acid sequence that is at least about 95%, 96%, 97%, 98%, 99%, or 99.5% identical to SEQ ID NO: 25. In an embodiment, the PD-1 protein variant does not comprise SEQ ID NO:7.

A second aspect of the subject invention provides nucleic acid molecules that encode the sPD-1 proteins of the subject invention. The nucleic acid molecules encompass DNA molecules (e.g. genomic DNA and cDNA) and RNA molecules. In addition, the subject nucleic acid molecules may be single-stranded or double-stranded.

In one embodiment, the nucleic acid molecule encodes a sPD-1 protein, which is obtained by deleting amino acid residues 26-39 of a wild-type sPD-1 protein (such as a wild-type human, mouse, or rabbit sPD-1 protein). In an embodiment, the nucleic acid molecule encodes mspd1-14del, and has a sequence comprising SEQ ID NO: 12. In an embodiment, the subject nucleic acid molecule encodes mspd1-322mu, and has a sequence comprising SEQ ID NO: 16. In an embodiment, the subject nucleic acid molecule encodes hspd1-14del, and has a sequence comprising SEQ ID NO: 26.

In certain embodiments, the subject invention encompasses nucleic acid molecules that are homologous to nucleic acids encoding mspd1-14del, mspd1-322mu, or hspd1-14del. In an embodiment, the nucleic acid molecule has a sequence that is at least about 95%, 96%, 97%, 98%, 99%, or 99.5% identical to SEQ ID NO: 12, SEQ ID NO: 16, or SEQ ID NO: 26. In an embodiment, the sPD-1 nucleic acid molecule does not comprise SEQ ID NO: 8.

A third aspect of the invention provides PD-1 fusion proteins. In one embodiment, the subject invention provides PD-1 fusion proteins, comprising a sPD-1 protein fragment fused with an antigenic protein fragment. In a further embodiment, the sPD-1 fusion protein comprises a Fc domain. In one embodiment, the soluble PD-1 protein is linked to the antigen via a linker sequence. In an alternative embodiment, the PD-1 fusion protein comprises a PD-1 protein fused with a Fc domain, optionally via a linker sequence.

In an embodiment, the sPD-1 fusion protein comprises the wild-type mouse soluble PD-1 protein (mspd), which has an amino acid sequence comprising SEQ ID NO: 1. In an embodiment, the sPD-1 fusion protein comprises the wild-type human sPD-1 protein (hspd1), which has an amino acid sequence comprising SEQ ID NO: 21. In an embodiment, the sPD-1 fusion protein is a variant mouse sPD-1 protein mspd1-14del, which has an amino acid sequence comprising SEQ ID NO: 11. In an embodiment, the sPD-1 fusion protein is a variant mouse sPD-1 protein mspd1-322mu, which has an amino acid sequence comprising SEQ ID NO: 15. In an embodiment, the sPD-1 protein is a variant human sPD-1 protein (hspd1-14del), and has an amino acid sequence comprising SEQ ID NO: 25.

The antigenic protein fragment can be derived from an immunogenic fragment of viral, bacterial, fungal, or other microbial pathogens including, but not limited to, human immunodeficiency virus (HIV), HSV including HSV-1 and HSV-2, KSHV, HPV including HPV-6, HPV-11, HPV-16, and HPV-18, respiratory syncytial virus, rhinovirus, hepatitis viruses including hepatitis A virus, hepatitis B virus, hepatitis C virus, hepatitis D virus, hepatitis E virus, hepatitis F virus, and hepatitis G virus, oncoviruses, human T-lymphotropic virus Type I (HTLV-1), influenza virus, bovine leukemia virus (BLV), Epstein-Barr virus, anpapillomavirus, *pneumococcus, streptococcus, staphylococcus, neisseria, E. coli*, cytomegalovirus (CMV), respiratory syncytial virus, parainfluenza virus, adenovirus, flavivirus, dengue virus, *Mycobacteria tuberculosis*, and *Plasmodium falciparu*; and pathogens causing diseases including, but not limited to, pertussis, polio, measles, mumps, rubella, smallpox, zoster, anthrax, tetanus, rabies, chickenpox, diphtheria, anthrax, plague, encephalitis, pneumonia, typhus, typhoid fever, lyme disease, cholera, *shigella, leishmania*, leprosy, toxoplasmosis, coccidiomycosis, schistosomiasis, and malaria. The antigenic protein fragment can also be derived from tumor or cancer cells.

In one embodiment, the soluble PD-1, its variants, and fusion proteins thereof serve as molecular or protein adjuvants to enhance immune response. Additionally, nucleic acid molecules encoding the soluble PD-1, its variants, and fusion proteins thereof can also be administered to a subject to enhance immune response.

In an embodiment, the antigenic protein fragment is derived from an immunogenic fragment of an HIV protein domain including, but not limited to, p24, gag, pol, nef, tat, rev, gp120, and gp41. In an embodiment, the antigen protein is derived from HIV p24. In a specific embodiment, the antigen protein comprises SEQ ID NO: 3. In a further embodiment, the sPD-1 fusion protein further comprises a Fc domain. In an embodiment, the sPD-1 fusion protein comprises a rabbit Fc domain for protein purification purpose.

The term "Fc domain" encompasses the full length and fragments of native human and animal Fc and Fc variant molecules and sequences, including for example, IgG, IgM, IgD, IgE, IgA and subtypes such as for example IgG1, IgG2, IgG3, IgG4, IgA1, and IgA2. As with Fc variants and native Fc's, the term "Fc domain" includes molecules in monomeric or multimeric form, whether digested from whole antibody or produced by other means.

In an embodiment, the antigenic protein fragment is derived from a tumor antigen.

The term "Fc variant" refers to a molecule or sequence that is modified from a native Fc but still comprises a binding site for the salvage receptor. Fc domains include molecules having two or more polypeptide chains associated covalently, noncovalently, or by both covalent and non-covalent interactions. IgG molecules typically form dimers; IgM, pentamers; IgD, dimers; and IgA, monomers, dimers, trimers, or tetramers. Multimers may be formed by exploiting the sequence and resulting activity of the native Ig source of the Fc or by derivatizing (as defined below) such a native Fc.

The Fc domain within the scope of the invention can be of antibodies of any isotype, including IgG, IgA, IgE, IgD, and IgM. IgG isotype antibodies can be further subdivided into IgG1, IG2, IgG3, and IgG4 subtypes. IgA antibodies can be further subdivided into IgA1 and IgA2 subtypes. In a specific embodiment, the Fc domain is IgG1.

In a further embodiment, the sPD-1 fusion protein of the subject invention comprises a linker sequence that links the soluble PD-1 domain to the antigen. In addition, the Fc domain can also be linked to the fusion protein via a linker sequence. Linker sequence is typically a peptide chain. The length of the peptide may be, for example, 6, 7, 8, 9, 10, 11, 12, 13, 14, 15, 16, 17, 18, 19, 20, 21, 22, 23, 24, 25, 30, 40, 50 or more amino acid residues, but typically is between 5 and 25 residues.

Depending upon the length and side chain composition, a linker may have, but need not have, greater than average flexibility. Flexibility can be calculated using algorithms known in the art. In an embodiment, the linker sequence is SEQ ID NO: 29. Examples of useful linkers include, but are not limited to, 9Gly (SEQ ID NO: 30), 9Glu (SEQ ID NO: 31), 9Ser (SEQ ID NO: 32), 5GlyCys2ProCys (SEQ ID NO: 33), 4Gly3Ser (SEQ ID NO: 34), Ser Cys Val Pro Leu Met Arg Cys Gly Gly Cys Cys Asn (SEQ ID NO: 35), Pro Ser Cys Val Pro Leu Met Arg Cys Gly Gly Cys Cys Asn (SEQ ID NO: 36), Gly Asp Leu Ile Tyr Arg Asn Gln Lys (SEQ ID NO: 37), and 9GlyProSerCysValProLeuMetArg-CysGlyGlyCysCysAsn (SEQ ID NO: 38).

In a specific embodiment, the subject sPD-1 fusion protein comprises SEQ ID NO: 13. In another specific embodiment, the subject sPD-1 fusion protein comprises SEQ ID NO: 17. In another specific embodiment, the subject sPD-1 fusion protein comprises SEQ ID NO: 19. In another specific embodiment, the subject sPD-1 fusion protein comprises SEQ ID NO: 23. In another specific embodiment, the subject sPD-1 fusion protein comprises SEQ ID NO: 27.

In addition, the subject invention provides sPD-1 fusion nucleic acid constructs, comprising a nucleic acid molecule encoding the subject sPD-1 fusion protein. In one embodiment, the sPD-1 fusion construct comprises a nucleic acid molecule encoding a sPD-1 protein fused with a nucleic acid encoding a protein antigen. In a further embodiment, the PD-1 fusion construct comprises a Fc DNA. In one embodiment, the soluble PD-1 DNA is linked to the antigen DNA via a linker sequence. Optionally, the Fc DNA is linked to the sPD-1-antigen DNA via a linker DNA sequence.

The antigenic nucleic acid molecule of the subject invention encodes immunogenic fragments of viral, bacterial, fungal, or other microbial pathogens including, but not limited to, human immunodeficiency virus (HIV), HSV including HSV-1 and HSV-2, KSHV, HPV including HPV-6, HPV-11, HPV-16, and HPV-18, respiratory syncytial virus, rhinovirus, hepatitis viruses including hepatitis A virus, hepatitis B virus, hepatitis C virus, hepatitis D virus, hepatitis E virus, hepatitis F virus, and hepatitis G virus, oncoviruses, human T-lymphotropic virus Type I (HTLV-1), influenza virus, bovine leukemia virus (BLV), Epstein-Barr virus, rotavirus, *meningococcus*, anpapillomavirus, *pneumococcus, streptococcus, staphylococcus, E. coli*, cytomegalovirus (CMV), respiratory syncytial virus, parainfluenza virus, adenovirus, flavivirus, dengue virus, *Mycobacteria tuberculosis*, and *Plasmodium falciparu*; and pathogens causing diseases including, but not limited to, pertussis, polio, measles, mumps, rubella, smallpox, zoster, anthrax, tetanus, rabies, chickenpox, diphtheria, anthrax, plague, encephalitis, pneumonia, typhus, typhoid fever, lyme disease, cholera, *shigella, leishmania*, leprosy, toxoplasmosis, coccidiomycosis, schistosomiasis, and malaria.

In an embodiment, the antigenic nucleic acid molecule encodes a tumor antigen. In an embodiment, the fusion nucleic acid molecule comprises the wild-type mouse PD-1 (mspd1) DNA (SEQ ID NO: 2). In an embodiment, the fusion nucleic acid molecule comprises the wild-type human PD-1 (hspd1) DNA (SEQ ID NO: 22). In an embodiment, the fusion nucleic acid molecule comprises a variant mouse PD-1 DNA that has a sequence of SEQ ID NO: 12 or SEQ ID NO: 16. In an embodiment, the fusion nucleic acid molecule comprises a variant human PD-1 DNA that has a sequence of SEQ ID NO: 26.

In a specific embodiment, the subject PD-1 fusion DNA comprises SEQ ID NO: 14. In another specific embodiment, the subject PD-1 fusion DNA comprises SEQ ID NO: 18. In another specific embodiment, the subject PD-1 fusion DNA comprises SEQ ID NO: 20. In another specific embodiment, the subject PD-1 fusion DNA comprises SEQ ID NO: 24. In another specific embodiment, the subject PD-1 fusion DNA comprises SEQ ID NO: 28. In certain embodiments, the PD-1 protein or nucleic acid of the subject invention is typically substantially free of other components, such as other biological molecules, proteins or peptides, nucleic acids, lipids and carbohydrates. The term "substantially free of," as used herein, encompasses preparations of the subject invention having less than about 20%, 10% and preferably less than 5% (by dry weight) contaminating factors (such as biological molecules, proteins or peptides, nucleic acids, lipids and carbohydrates and other cellular components).

If desired, the subject proteins and nucleic acid molecules can be modified by any suitable process. Strategies for protein optimization are sometimes carried out using random mutagenesis. In these cases positions are chosen randomly, or amino acid changes are made using simplistic rules. For example all residues may be mutated to alanine, referred to as alanine scanning. In addition, substitution of amino acids other than those specifically exemplified or naturally present in a fusion protein of the invention are also within the scope of the subject invention. For example, non-natural amino acids can be substituted for the amino acids of the fusion protein, so long as the fusion protein having the substituted amino acids retains substantially the same functional activity as the fusion protein in which amino acids have not been substituted.

Examples of non-natural amino acids include, but are not limited to, ornithine, citrulline, hydroxyproline, homoserine, phenylglycine, taurine, iodotyrosine, 2,4-diaminobutyric acid, α-amino isobutyric acid, 4-aminobutyric acid, 2-amino butyric acid, γ-amino butyric acid, ε-amino hexanoic acid, 6-amino hexanoic acid, 2-amino isobutyric acid, 3-amino propionic acid, norleucine, norvaline, sarcosine, homocitrulline, cysteic acid, τ-butylglycine, τ-butylalanine, phenylglycine, cyclohexylalanine, β-alanine, fluoro-amino acids, designer amino acids such as β-methyl amino acids, C-methyl amino acids, N-methyl amino acids, and amino acid analogues in general. Non-natural amino acids also include amino acids having derivatized side groups. Furthermore, any of the amino acids in the protein can be of the D (dextrorotary) form or L (levorotary) form.

The subject invention also concerns variants of nucleic acid molecules that encode functional fusion proteins of the invention. Variant sequences include those sequences wherein one or more nucleotides of the sequence have been substituted, deleted, and/or inserted.

The nucleotides that can be substituted for natural nucleotides of DNA have a base moiety that can include, but is not limited to, inosine, 5-fluorouracil, 5-bromouracil, hypoxanthine, 1-methylguanine, 5-methylcytosine, and tritylated bases. The sugar moiety of the nucleotide in a sequence can also be modified and includes, but is not limited to, arabinose, xylulose, and hexose. In addition, the adenine, cytosine, guanine, thymine, and uracil bases of the nucleotides can be modified with acetyl, methyl, and/or thio groups. Sequences containing nucleotide substitutions, deletions, and/or insertions can be prepared and tested using standard techniques known in the art.

Unless otherwise specified, as used herein percent sequence identity and/or similarity of two sequences can be determined using the algorithm of Karlin and Altschul (1990), modified as in Karlin and Altschul (1993). Such an algorithm is incorporated into the NBLAST and XBLAST programs of Altschul et al. (1990). BLAST searches can be performed with the NBLAST program, score=100, wordlength=12, to obtain sequences with the desired percent sequence identity. To obtain gapped alignments for comparison purposes, Gapped BLAST can be used as described in Altschul et al. (1997). When utilizing BLAST and Gapped BLAST programs, the default parameters of the respective programs (NBLAST and XBLAST) can be used. See NCBI/NIH website.

The subject invention also contemplates those nucleic acid molecules having sequences which are sufficiently homologous with the nucleic acid sequences exemplified herein so as to permit hybridization with that sequence under standard stringent conditions and standard methods (Maniatis et al., 1982). As used herein, "stringent" conditions for hybridization refers to conditions wherein hybridization is typically carried out overnight at 20-25 C below the melting temperature (Tm) of the DNA hybrid in 6×SSPE, 5×Denhardt's solution, 0.1% SDS, 0.1 mg/ml denatured DNA. The melting temperature, Tm, is described by the following formula (Beltz et al., 1983):

$$Tm=81.5\ C+16.6\ Log\ [Na+]+0.41(\%\ G+C)-0.61(\%\ formamide)-600/\text{length of duplex in base pairs.}$$

Washes are typically carried out as follows:
(1) Twice at room temperature for 15 minutes in 1×SSPE, 0.1% SDS (low stringency wash).
(2) Once at Tm-20 C for 15 minutes in 0.2×SSPE, 0.1% SDS (moderate stringency wash).

Further, the subject invention provides expression constructs comprising PD-1 nucleic acid molecules or fusion constructs thereof. Expression constructs of the invention generally include regulatory elements that are functional in the intended host cell in which the expression construct is to be expressed. Regulatory elements include promoters, transcription termination sequences, translation termination sequences, enhancers, and polyadenylation elements.

An expression construct of the invention can comprise a promoter sequence operably linked to a nucleic acid sequence encoding a peptide of the invention. Multiple copies of promoters or multiple promoters can be used in an expression construct of the invention. In a preferred embodiment, a promoter can be positioned about the same distance from the transcription start site as it is from the transcription start site in its natural genetic environment. Some variation in this distance is permitted without substantial decrease in promoter activity. A transcription start site is typically included in the expression construct.

For expression in animal cells, an expression construct of the invention can comprise suitable promoters that can drive transcription of the polynucleotide sequence. For mammalian cells, suitable promoters include for example, Pcmv, actin promoter, metallothionein promoter, NF-kappaB promoter, EGR promoter, SRE promoter, IL-2 promoter, NFAT promoter, osteocalcin promoter, SV40 early promoter and SV40 late promoter, Lck promoter, BMP5 promoter, and TRP-1 promoter.

Protection against Pathogenic Infection and Cancer

Another aspect of the subject invention provides methods for the prevention and/or treatment of pathogenic infection and/or cancer. Advantageously, the methods of the subject invention induce antigen-specific humoral and cell-mediated immunity. In one embodiment, the method comprises administering, to a subject in need of such treatment, an effective amount of a fusion protein or fusion nucleic acid molecule of the subject invention.

In an embodiment, the subject invention provides a method of inducing protective immunity against pathogenic infection and/or cancer. In a specific embodiment, the method comprises administering a composition comprising a fusion nucleic acid molecule, wherein the fusion nucleic acid molecule comprises a nucleic acid encoding an antigen of interest; a sPD-1 nucleic acid encoding a wild-type soluble PD1 protein, a nucleic acid encoding a spd1-14 del protein of the invention, or a nucleic acid encoding a spd1-322 del protein of the invention; and, optionally, a nucleic acid encoding Fc domain and a linker nucleic acid sequence that links the sPD-1 nucleic acid and the antigen nucleic acid. In one embodiment, the composition is administered by intramuscular injection via electroporation (EP).

In another specific embodiment, the method comprises administering a composition comprising a fusion protein, wherein the fusion protein comprises an antigen of interest; a soluble PD-1 protein selected from a wild-type soluble PD1 protein, a spd1-14del protein of the invention, or a spd1-322 del protein of the invention; and, optionally, a Fc domain and a linker sequence that links the sPD-1 protein and the antigen protein.

The methods can be used for prevention and/or treatment of infection and other diseases where induction of antigen-specific humoral and cell-mediated immunity is beneficial. In a specific embodiment, the subject invention can be used in the prevention and/or treatment of tumor or cancer.

The term "treatment" or any grammatical variation thereof (e.g., treat, treating, and treatment etc.), as used herein, includes but is not limited to, ameliorating or alleviating a symptom of a disease or condition, reducing, suppressing, inhibiting, lessening, or affecting the progression, severity, and/or scope of a condition.

The term "prevention" or any grammatical variation thereof (e.g., prevent, preventing, and prevention etc.), as used herein, includes but is not limited to, delaying the onset of symptoms, preventing relapse to a disease, decreasing the number or frequency of relapse episodes, increasing latency between symptomatic episodes, or a combination thereof. Prevention, as used herein, does not require complete inhibition or elimination of symptoms.

The term "effective amount," as used herein, refers to an amount that is capable of treating or ameliorating a disease or condition or otherwise capable of producing an intended therapeutic effect.

The term "subject," as used herein, describes an organism, including mammals such as primates, to which treatment with the compositions according to the subject invention can be provided. Mammalian species that can benefit from the disclosed methods of treatment include, but are not limited to, apes, chimpanzees, orangutans, humans, monkeys; and other animals such as dogs, cats, horses, cattle, pigs, sheep, goats, chickens, mice, rats, guinea pigs, and hamsters.

In certain embodiments, in case of prevention of pathogenic infection or cancer, the sPD-1-based composition of the invention is administered to a subject that does not suffer from the pathogenic infection or cancer type to be prevented, or a subject that does not exhibit symptoms of the pathogenic infection or cancer type to be prevented.

In one embodiment, the subject invention can be used in the prevention and/or treatment of infection by viral, bacterial, fungal, or other microbial pathogens including, but not limited to, human immunodeficiency virus (HIV), HSV including HSV-1 and HSV-2, KSHV, HPV including HPV-6, HPV-11, HPV-16, and HPV-18, respiratory syncytial virus, rhinovirus, hepatitis viruses including hepatitis A virus, hepatitis B virus, hepatitis C virus, hepatitis D virus, hepatitis E virus, hepatitis F virus, and hepatitis G virus, oncoviruses, human T-lymphotropic virus Type I (HTLV-1), influenza virus, bovine leukemia virus (BLV), Epstein-Barr virus, rotavirus, *meningococcus*, anpapillomavirus, *pneumococcus, streptococcus, staphylococcus, E. coli*, cytomegalovirus (CMV), respiratory syncytial virus, parainfluenza virus, adenovirus, dengue virus, *Mycobacteria tuberculosis*, and *Plasmodium falciparu*; and pathogens causing diseases including, but not limited to, pertussis, polio, measles, mumps, rubella, smallpox, zoster, anthrax, tetanus, rabies, chickenpox, diphtheria, anthrax, plague, encephalitis, pneumonia, typhus, typhoid fever, lyme disease, cholera, *shigella, leishmania*, leprosy, toxoplasmosis, coccidiomycosis, schistosomiasis, and malaria.

In a specific embodiment, the subject invention can be use to prevent and/or treat HIV infection. In certain embodiments, the method comprises administering to a subject in need of such treatment an effective amount of a fusion protein, comprising an amino acid sequence selected from SEQ ID NOs: 13, 17, 19, 23, and 27. In specific embodiments, the subject method comprises administering to a subject in need of such treatment an effective amount of a fusion DNA, comprising a nucleic acid sequence selected from SEQ ID NOs: 14, 18, 20, 24, and 28.

In addition, the methods can be used in the prevention and/or treatment of diseases where enhanced humoral and cell-mediated immunity is beneficial. In an embodiment, the subject invention can be used in the prevention and/or treatment tumor or cancer.

In one embodiment, the sPD-1 protein useful for the prevention and/or treatment of tumor comprises an antigenic fragment derived from cancer or tumor cells. Soluble PD-1 proteins useful for the prevention and/or treatment of tumor or cancer also include, for example, the wild-type mspd-1 (SEQ ID NO:1), the wild-type hspd1 (SEQ ID NO: 21), mspd1-14del (SEQ ID NO: 11), mspd1-322mu (SEQ ID NO: 15), hspd1-14del (SEQ ID NO: 25), or fusion proteins thereof. Additionally or alternatively, the PD-1 protein useful for the prevention and/or treatment of tumor or cancer comprises an amino acid sequence that is at least 95%, 96%, 97%, 98%, 99%, or 99.5% identical to the wild-type mspd-1 (SEQ ID NO:1), the wild-type hspd1 (SEQ ID NO: 21), mspd1-14del (SEQ ID NO: 11), mspd1-322mu (SEQ ID NO: 15), hspd1-14del (SEQ ID NO: 25), or fusion proteins thereof.

In specific embodiments, sPD-1 nucleic acid molecules useful for the prevention and/or treatment of tumor or cancer include, for example, the wild-type mspd-1 DNA (SEQ ID NO:2), the wild-type hspd1 DNA (SEQ ID NO: 22), mspd1-14del DNA (SEQ ID NO: 12), mspd1-322mu DNA (SEQ ID NO: 16), hspd1-14del DNA (SEQ ID NO: 26), or fusion DNA thereof.

Additionally or alternatively, the sPD-1 nucleic acid molecule useful for the prevention and/or treatment of tumor or cancer comprises a sequence that is at least 90%, 95%, 96%, 97%, 98%, 99%, or 99.5% identical to the wild-type mspd-1 DNA (SEQ ID NO:2), the wild-type hspd1 DNA (SEQ ID NO: 22), mspd1-14del DNA (SEQ ID NO: 12), mspd1-322mu DNA (SEQ ID NO: 16), hspd1-14del DNA (SEQ ID NO: 26), or fusion DNA thereof.

Therapeutic Compositions and Routes of Administration

The subject invention further provides for therapeutic or pharmaceutical compositions. In an embodiment, the composition comprises a therapeutically effective amount of a protein and/or nucleic acid molecule of the subject invention and, optionally, a pharmaceutically acceptable carrier.

In one embodiment, the proteins and/or nucleic acid molecules are formulated into a vaccine composition for administration to subjects having certain risks of pathogenic infection. A vaccine composition is an antigenic preparation that comprises one or more immunogenic antigens used to produce active immunity to a disease. In addition, the compositions of the subject invention can be administered to a subject with existing infection, and provide for customized vaccine schedules and compositions to prevent or minimize worsening of the diseases.

The subject invention contemplates therapeutic compositions useful for practicing the therapeutic methods described herein. The therapeutic composition can be any form of pharmaceutical format, including injectable formulations such as liquid and lyophilized injections.

In a specific embodiment, a therapeutically effective amount of a protein and/or nucleic acid molecule of the subject invention is typically an amount such that when administered in a physiologically tolerable composition is sufficient to achieve a plasma concentration of from about 0.01 microgram (ug) per milliliter (mL) to about 200 ug/mL. Stated differently, the dosage can vary from about 0.1 mg/kg to about 300 mg/kg, preferably from about 0.2 mg/kg to about 200 mg/kg, most preferably from about 0.5 mg/kg to about 20 mg/kg, in one or more dose administrations daily, for one or several days.

Suitable non-toxic pharmaceutically acceptable carriers for use with the agent will be apparent to those skilled in the art of pharmaceutical formulation. See, for example, *Remington's Pharmaceutical Sciences*, seventeenth edition, ed. Alfonso R. Gennaro, Mack Publishing Company, Easton, Pa. (1985). Suitable carriers include ethanol, dimethyl sulfoxide, glycerol, silica, alumina, starch, sorbitol, inosital, xylitol, D-xylose, mannitol, powdered cellulose, microcrystalline cellulose, talc, colloidal silicon dioxide, calcium carbonate, magnesium cabonate, calcium phosphate, calcium aluminum silicate, aluminum hydroxide, sodium starch phosphate, lecithin, and equivalent carriers and diluents. Saline solutions and aqueous dextrose and glycerol solutions can also be employed as liquid carriers, particularly for injectable solutions.

Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene glycol, water, ethanol, and the like. The therapeutic composition, if desired, can also contain minor amounts of wetting or emulsifying agents, or pH buffering agents. In addition, if desired, the composition can contain minor amounts of auxiliary substances such as wetting or emulsifying agents, pH buffering agents and the like which enhance the effectiveness of the active ingredient.

The amount of active ingredient that may be combined with the carrier materials to produce a single dosage form will vary, depending on the type of the condition and the subject to be treated. In general, a therapeutic composition contains from about 5% to about 95% active ingredient (w/w). More specifically, a therapeutic composition contains from about 20% (w/w) to about 80%, or about 30% to about 70%, active ingredient (w/w).

The preparation of a pharmacological composition that contains active ingredients dissolved or dispersed therein is well understood in the art and need not be limited based on formulation. Typically such compositions are prepared as injectables either as liquid solutions or suspensions; however, solid forms suitable for solution, or suspensions, in liquid prior to use also can be prepared. The preparation also can be emulsified.

The therapeutic composition of the subject invention can include pharmaceutically acceptable salts of the components therein. Pharmaceutically acceptable salts include the acid addition salts (formed with the free amino groups of a polypeptide) that are formed with inorganic acids such as, for example, hydrochloric or phosphoric acids, or such organic acids as acetic, tartaric, mandelic and the like. Salts formed with the free carboxyl groups also can be derived from inorganic bases such as, for example, sodium, potassium, ammonium, calcium or ferric hydroxides, and such organic bases as isopropylamine, trimethylamine, 2-ethylamino ethanol, histidine, procaine and the like.

As used herein, the terms "pharmaceutically acceptable", "physiologically tolerable" and grammatical variations thereof, as they refer to compositions, carriers, diluents and reagents, are used interchangeably and represent that the materials are capable of administration to or upon a mammal.

The invention also provides a pharmaceutical pack or kit comprising one or more containers filled with one or more of the ingredients, e.g., compound, carrier suitable for administration.

The compositions of the subject invention can be administered to the subject being treated by standard routes, including oral, inhalation, or parenteral administration including intravenous, subcutaneous, topical, transdermal, intradermal, transmucosal, intraperitoneal, intramuscular, intracapsular, intraorbital, intracardiac, transtracheal, subcutaneous, subcuticular, intraarticular, subcapsular, subarachnoid, intraspinal, epidural and intrasternal injection, infusion, and electroporation, as well as co-administration as a component of any medical device or object to be inserted (temporarily or permanently) into a subject.

In a preferred embodiment, the microparticles of the subject invention can be formulated for parenteral administration. The preparation of an aqueous composition that contains one or more agents, such as a protein or nucleic acid molecule of the subject invention, will be known to those of skill in the art in light of the present disclosure. Typically, such compositions can be prepared as injectables, either as liquid solutions or suspensions; solid forms suitable for using to prepare solutions or suspensions upon the addition of a liquid prior to injection can also be prepared; and the preparations can also be emulsified.

The pharmaceutical forms suitable for injectable use include sterile aqueous solutions or dispersions; formulations including sesame oil, peanut oil or aqueous propylene glycol; and sterile powders for the extemporaneous preparation of sterile injectable solutions or dispersions. In all cases the form must be sterile and must be fluid to the extent that easy syringability exists. It must be stable under the conditions of manufacture and storage and must be preserved against the contaminating action of microorganisms, such as bacteria and fungi.

Sterile injectable solutions are prepared by incorporating the active ingredients in the required amount in the appropriate solvent followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum drying and freeze-drying techniques, which yield a powder of the active ingredient, plus any additional desired ingredient from a previously sterile-filtered solution thereof.

In addition, the nucleic acid molecules and compositions of the subject invention can be delivered in vivo into a host cell by methods known in the art. In one embodiment, the nucleic acid molecules and compositions of the subject invention can be introduced in vivo via a viral vector such as adeno-associated virus (AAV), herpes simplex virus (HSV), retrovirus, papillomavirus, adenovirus, and Epstein-Barr virus (EBV). In addition, the nucleic acid molecules and compositions of the subject invention can also be introduced in vivo via lipofection (DNA transfection via liposomes prepared from synthetic cationic lipids) (Felgner et al., 1987). Synthetic cationic lipids (LIPOFECTIN, Invitrogen Corp., La Jolla, Calif.) can be used to prepare liposomes to encapsulate the nucleic acid molecules of the invention. The nucleic acid molecules of the subject invention can also be introduced in vivo as naked DNA using methods known in the art, such as transfection, microinjection, electroporation, calcium phosphate precipitation, and by biolistic methods.

EXAMPLES

Following are examples that illustrate embodiments for practicing the invention. These examples should not be construed as limiting. All percentages are by weight and all solvent mixture proportions are by volume unless otherwise noted.

Example 1

Construction of Mouse sPD-1 Vaccine Candidates

This Example illustrates the construction of mouse sPD-1-p24 fusion constructs. To construct mouse sPD-1-p24-Fc construct, PVAX vector that carries the wild-type msPD-1 gene and p24 gene was fused with rabbit Fc DNA. The vector and the p24-Fc DNA were linked by a linker encoding GGGSGGG (SEQ ID NO: 29). The transcription is under the control of promoter Pcmv.

Mouse sPD1 protein variant mspd1-IgVΔ was obtained by deleting amino acids 89-90 of the mouse PD-1 protein, which forms the C"D loop of the IgV domain and is essential for PD-1 and PD-L1/L2 interaction. PVAX vector carrying mspd1-IgVΔ was linked with p24-rabbit Fc DNA via a linker encoding GGGSGGG (SEQ ID NO: 29) linker sequence. In addition, p24-Fc fusion construct was obtained by linking the PVAX vector carrying p24 with rabbit Fc DNA. The transcription is under the control of promoter Pcmv.

FIG. 1A shows alignment of amino acid sequences of msPd1-p24-Fc, mspd1-IgVΔ-p24-Fc, and p24-fc fusion proteins. FIG. 1B shows Western blot results of various fusion constructs useful according to the subject invention. Briefly, 293T cells were transfected with various fusion constructs using polyethylenimine (PEI) and the supernatants were collected 72 hours post transfection. Proteins were detected by anti-rabbit Fc antibody. FIG. 1B shows that msPd1-p24-Fc and mspd1-IgVΔ-p24-Fc are about 72KD in size, while p24-Fc is about 50KD in size. The results also show that msPd1-p24-Fc, mspd1-IgVΔ-p24-Fc, and p24-Fc fusion proteins are soluble.

Example 2

Binding Ability of Mouse sPD-1 Fusion Protein to sPD-1 Ligands

This Example shows the binding ability of msPD-1 fusion proteins to mouse sPD-1 ligands. Briefly, 293T cells were transfected with PD-L (PD-L1 and PD-L2). The binding of sPD-1 proteins to PD-1 ligands was detected by FITC-anti rabbit Fc antibody using flow cytometer, and the results were analyzed by flowJo.

Figure 2A:
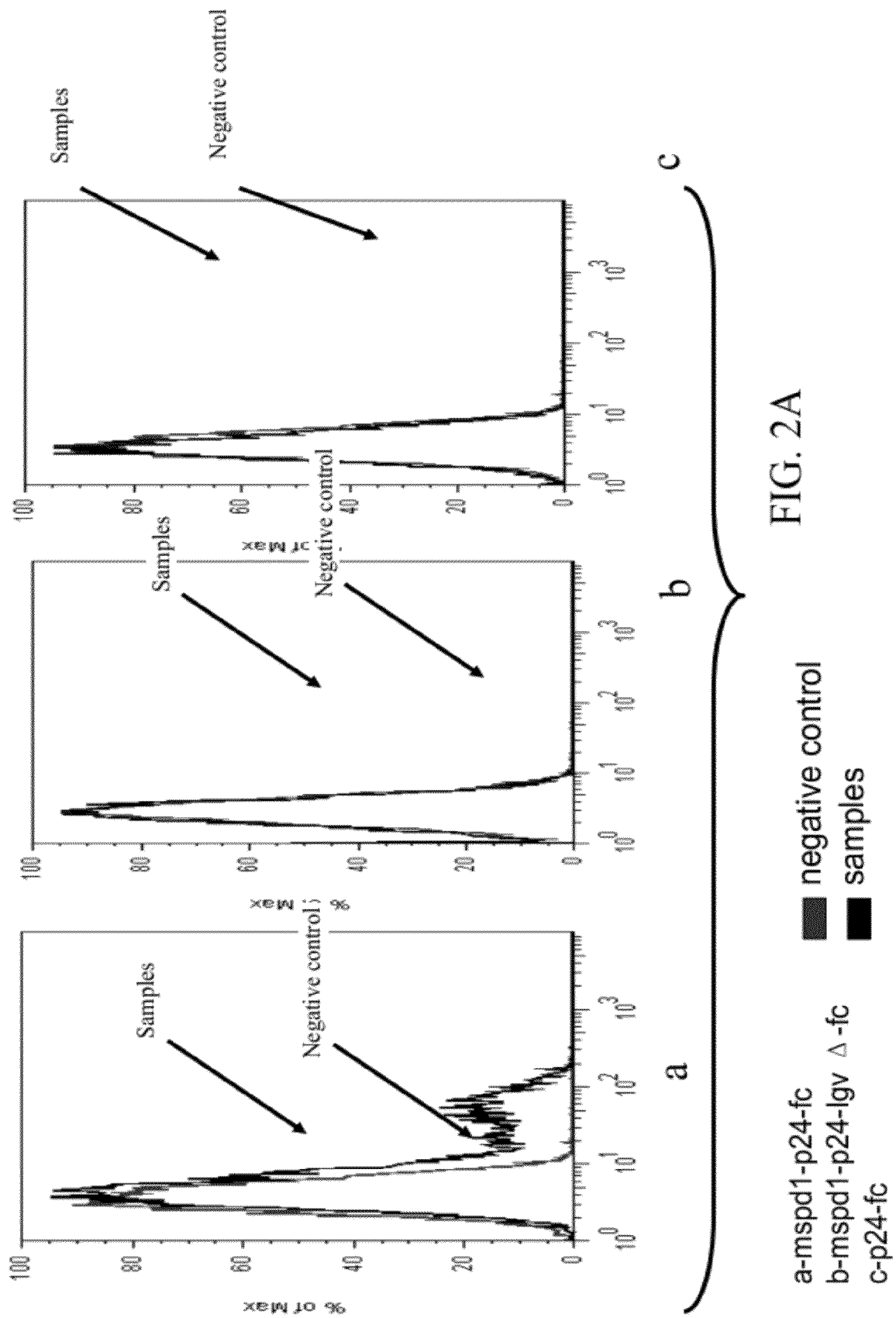
FIG. 2 shows the binding ability of msPD1-p24-Fc fusion proteins to sPD-1 ligands. (A) shows the binding ability of mspd1-p24-Fc, mspd1-IgVΔ-p24-Fc and p24-Fc to mouse PD-L1, respectively. (B) shows the binding ability of mspd1-p24-Fc, mspd1-IgVΔ-p24-Fc and p24-Fc to mouse PD-L2, respectively.
Figure 2B:
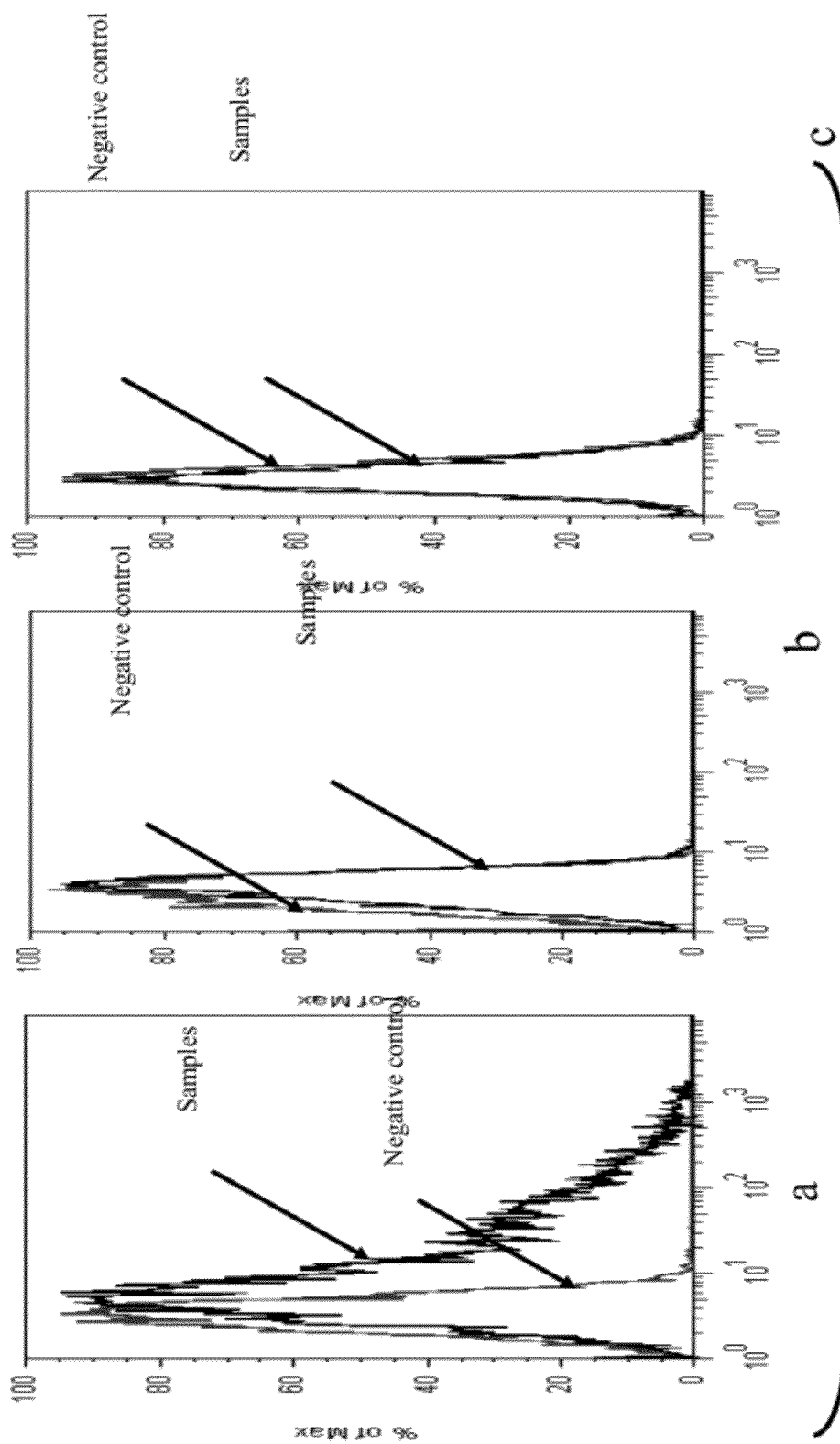
Figure 3A:
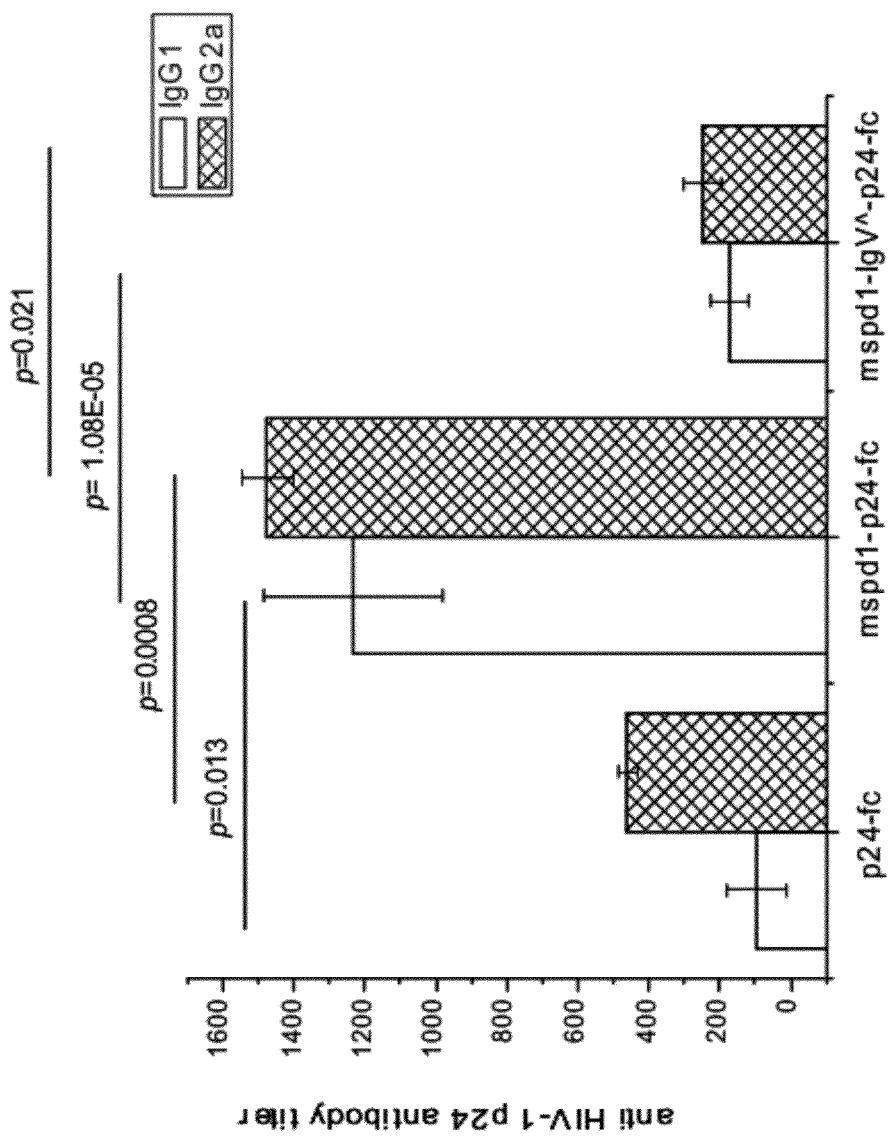
FIG. 3 shows that wild-type sPD 1 DNA elicits humoral and cell-mediated immune responses against HIV p24. (A) shows serum levels of anti-p24 IgG1 and IgG2a antibodies in mice immunized with p24-Fc, mspd1-p24-Fc and mspd1-IgVΔ-p24-Fc fusion DNA, respectively. Bars represent the average values of three samples (±standard deviations). (B) shows the number of IFN-γ-secreting splenocytes specific for p24 epitope gagAI (AMQMLKDTI) (SEQ ID NO: 39) for CD8 T cells. Bars represent the average values of three samples (+ standard deviations). (C) shows images of splenocytes isolated from immunized mice. To analyze p24-specific immune response, splenocytes were stained with H2d-Kd gagAI-PE tetramer for CD8 T cell population analysis. (D) shows the number of IFN-γ-secreting splenocytes specific for p24 epitope gag26 (TSNPPIPVGDIYKRWIILGL) (SEQ ID NO: 40)—for CD4 T cells. Bars represent the average values of three samples (±standard deviations). Data represent three experiments on the same batch of immunized mice.
Figure 3B:
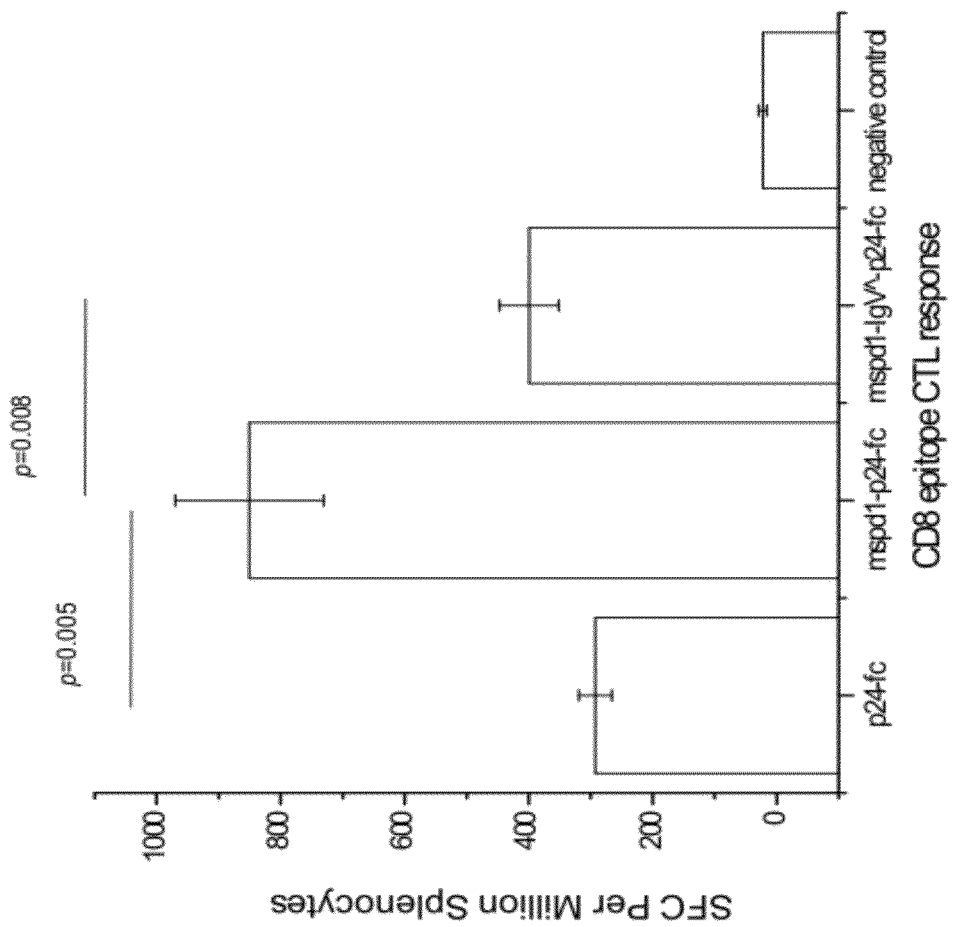
Figure 3C:
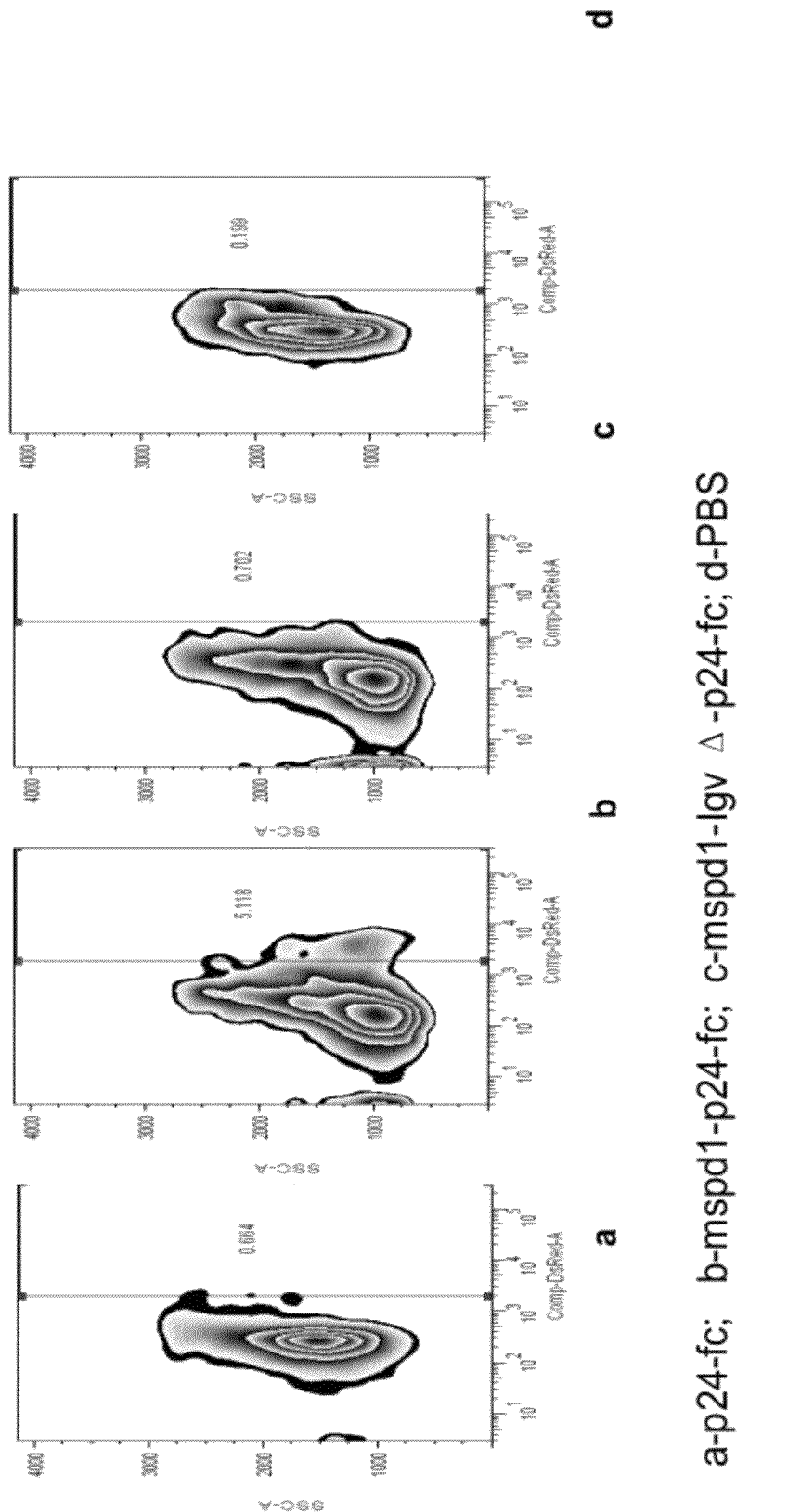
Figure 3D:
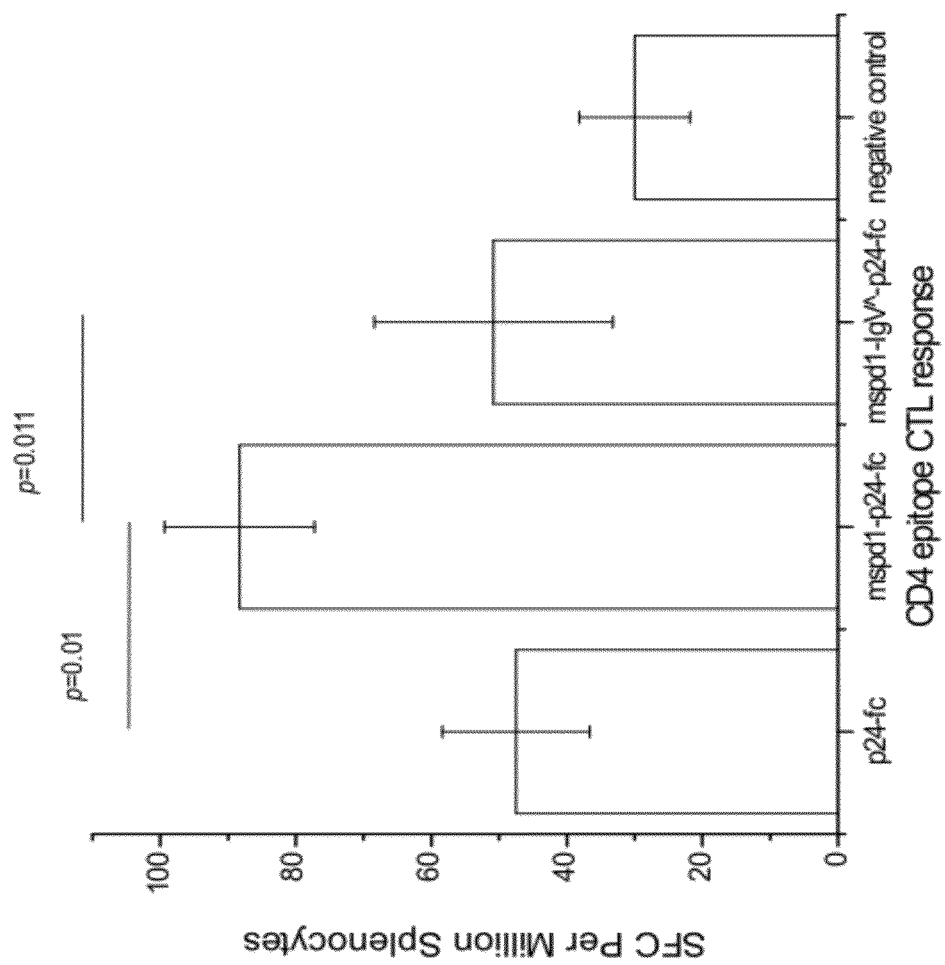

The results, as shown in FIGS. 2A-B, reveal that mspd1-p24-Fc binds to mouse PD-1 ligands PD-L1 and PD-L2. In contrast, the variant mspd1-IgVΔ fusion protein does not bind to mouse PD-1 ligands. In addition, p24-Fc does not affect the interaction between PD-1 and PD-L1/L2.

Example 3

Induction of Humoral and Cell-Mediated Immune Responses by Wild-Type Mouse sPD1 Vaccine This Example shows that the wild-type msPD1-p24-Fc potently induces humoral and cell-mediated immune responses. Briefly, Balb/c mice were primed at week 0 and boosted at week 3 and week 6 with 20 µg mouse DNA vectors encoding msPd1-p24-Fc, mspd1-IgVΔ-p24-Fc, or p24-Fc via intramuscular electroporation. Mice that received PBS served as controls.

Two weeks after the last immunization, mice sera were collected and contacted with HIV-1 p24 viral proteins. The levels of anti-p24 IgG1 and IgG2a antibodies were measured by ELISA. The level of anti-p24 antibody in control samples is not shown because the absorbance readouts of these samples fell below the cutoff values for determining antibody titers. The anti-p24 antibody endpoint titer is defined as the reciprocal of the highest dilution of a test sample that produces a reading of at least two-fold greater than that of the control sample with the same dilution. The results show that mice immunized with mspd1-p24-Fc had high IgG1 and IgG2a titers, when compared to mice immunized with p24-Fc or mspd1-IgVΔ-p24-Fc.

To examine p24-specific immune responses, the number of IFN-γ-secreting splenocytes specific for p24 epitope gagAI (AMQMLKDTI) (SEQ ID NO: 39) for CD8 T cells and the number of splenocytes specific for p24 epitope gag26 (TSN-PPIPVGDIYKRWIILGL) (SEQ ID NO: 40) for CD4 T cells was determined using ELIspot assay. In addition, splenocytes isolated from immunized vaccinated mice were subject to H2d-Kd-gagAI-PE tetramer staining, and CD8 T cell and CD4 T cell population was analyzed.

The results show that mice immunized with mspd1-p24-Fc had high anti-p24 antibody titers (FIG. 3A) and high number of IFN-γ-secreting splenocytes (FIGS. 3B and 3D), when compared to mice immunized with p24-Fc or mspd1-IgVΔ-p24-Fc. Splenocytes isolated from mice immunized with mspd1-p24-Fc contained about five-fold higher H2d-Kd gagAI tetramer-positive cells (FIG. 3C), when compared to mice immunized with p24-Fc or mspd1-IgVΔ-p24-Fc.

Example 4

Figure 4:
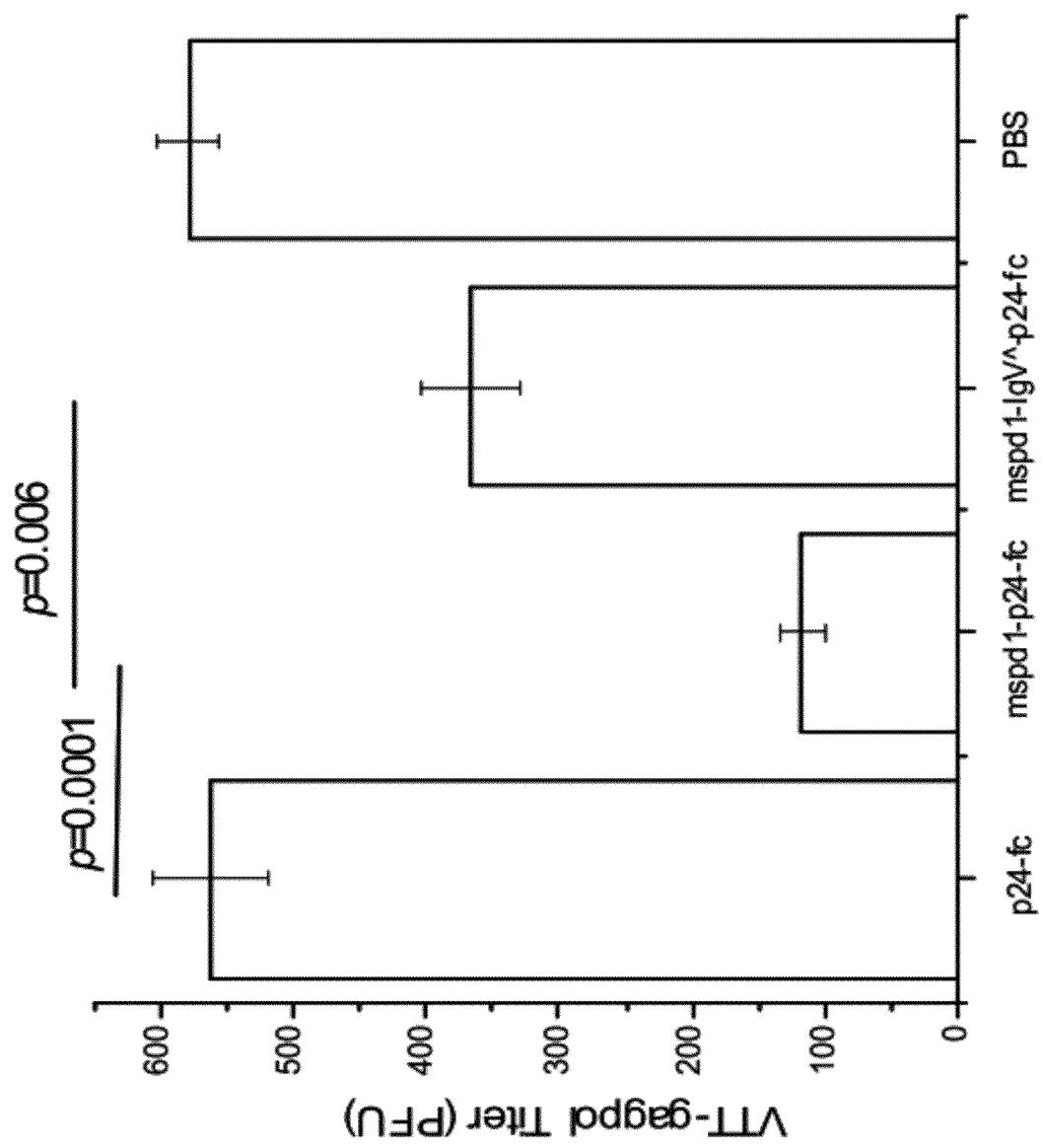
FIG. 4 shows that immunization with wild-type msPD 1 fusion DNA protects mice against viral infection. Balb/c mice immunized with p24-Fc, mspd1-p24-Fc or mspd1-IgVΔ-p24-Fc were challenged with $4 \times 10^7$ PFU of vaccinia VTT-HIV-gagpol intranasally three weeks after the last immunization. The mice were sacrificed 3 days after viral challenge. Viral titers in lungs were evaluated by plaque-forming assay in Vero cells. Bars represent the average values of five samples (±standard deviations).

Reduction of VTT-HIV-Gagpol Titers in Mice Immunized with Wild-Type Mouse sPD1 Fusion Protein This Example shows that immunization with the wide-type msPD1 fusion protein protects against viral infection. Briefly, Balb/c mice were primed at week 0 and boosted at week 3 and week 6 with 20 µg mouse DNA encoding msPd1-p24-Fc, mspd1-IgVΔ-p24-Fc, or p24-Fc via intramuscular electroporation. Mice that received PBS served as controls. Three weeks after immunization, mice were challenged with 4×10⁷PFU vaccinia VTT-HIV-gagpol intranasally. The mice were sacrificed 3 days after viral challenge and viral titers in the lungs were evaluated by plaque assay. The results show that mice immunized with mspd1-p24-Fc exhibited significantly reduced VTT-HIV-gagpol titers upon viral challenge (FIG. 4).

Figures 5A, 5B:
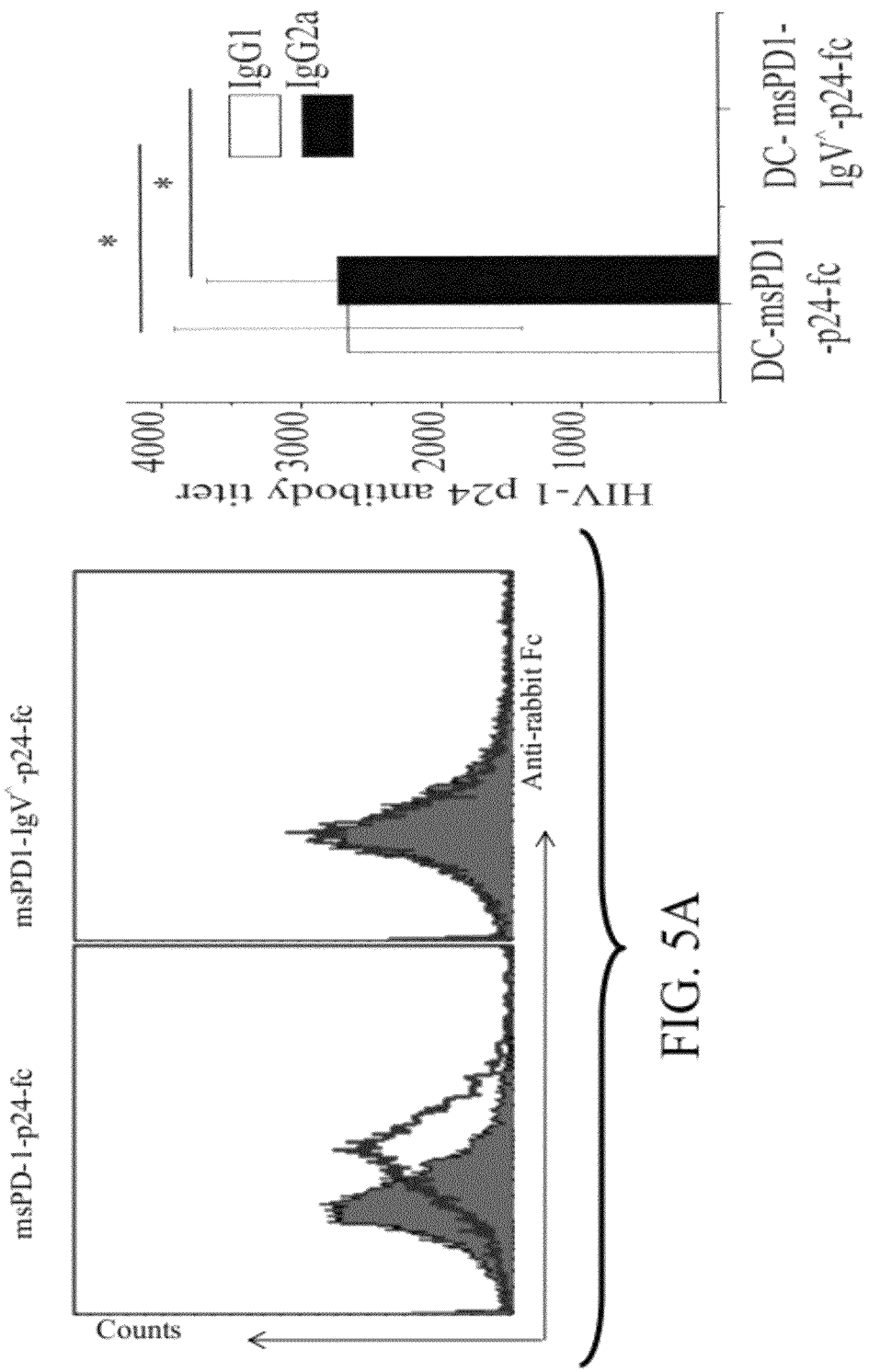
FIG. 5 shows that targeting DCs using sPD-1-p24-fc induces enhanced p24-specific antibody and T cell responses. (A) Expression of PD-L1 and PD-L2 on purified CD11c+ BM-DCs isolated from Balb/c mice were confirmed by flow cytometric analysis using anti-mouse PD-L1 or L2 antibodies (solid line, not shaded). Cells stained with isotype antibody control are shown as shaded histogram. (B) BM-DCs treated with purified msPD-1-p24-fc and msPD1-IgVΔ-p24-fc proteins to examine binding. Proteins bound to DCs were detected by flow cytometry using an anti-rabbit Fc-FITC antibody (solid line, not shaded) in parallel to DCs without treatment of proteins as negative control (shaded). $2 \times 10^6$ DCs treated with 20 μg of msPD-1-p24-fc or msPD1-IgVΔ-p24-fc proteins were introduced to Balb/c mouse by tail vein injection once every three weeks for a total experimental duration of six weeks. Mice that received untreated CD11c$^+$ DCs served as control. (C) Mice sera were collected and analyzed for the presence of IgG1 and IgG2a antibodies specific against HIV-1 p24 by ELISA. (D) IFN-γ producing CD8$^+$ and CD4$^+$ cells were measured by ELISpot assay in mice splenocytes stimulated using specific peptides gagAI and gag26, respectively. H2-Kd-gagAI-PE tetramer staining was performed on isolated splenocytes and analyzed by flow cytometry as a column graph of data from groups of immunized mice. Bars represent the mean values of two replicate mice with standard error depicted by error bars. Data are representative of two independent immunization experiments. *P<0.05.

FIG. 5 shows that targeting dendritic cells using sPD-1-p24-fc induces enhanced p24-specific antibody and T cell responses.

Example 5

Induction of Humoral and Cell-Mediated Immune Responses by Wild-Type Human sPD1 Vaccine Human sPD-1-p24-Fc was constructed by fusing PVAX vector carrying hsPD-1-p24 with rabbit Fc DNA. The vector and the p24-Fc DNA were linked by a linker encoding GGGSGGG (SEQ ID NO: 29). The transcription is under the control of promoter Pcmv.

To analyze the binding ability of hsPD-1-p24-Fc to sPD-1 ligands, 293T cells were transfected with mouse PD-L1 and PD-L2, respectively. The binding of sPD-1 proteins to PD-1 ligands was detected by mouse sPD-1-Fc proteins and FITC-anti rabbit Fc antibody using flow cytometer, and the results were analyzed by flowJo. The results, as shown in FIGS. 6A and 6B, reveal that hspd1-p24-Fc fusion protein binds to PD-1 ligands.

To examine the induction of immune responses by hsPD-1-p24-Fc, Balb/c mice were primed at week 0 and boosted at week 3 and week 6 with 20 µg mouse DNA encoding hsPD1-p24-Fc or p24-Fc via intramuscular electroporation. Mice that received PBS served as controls.

Figure 6D:
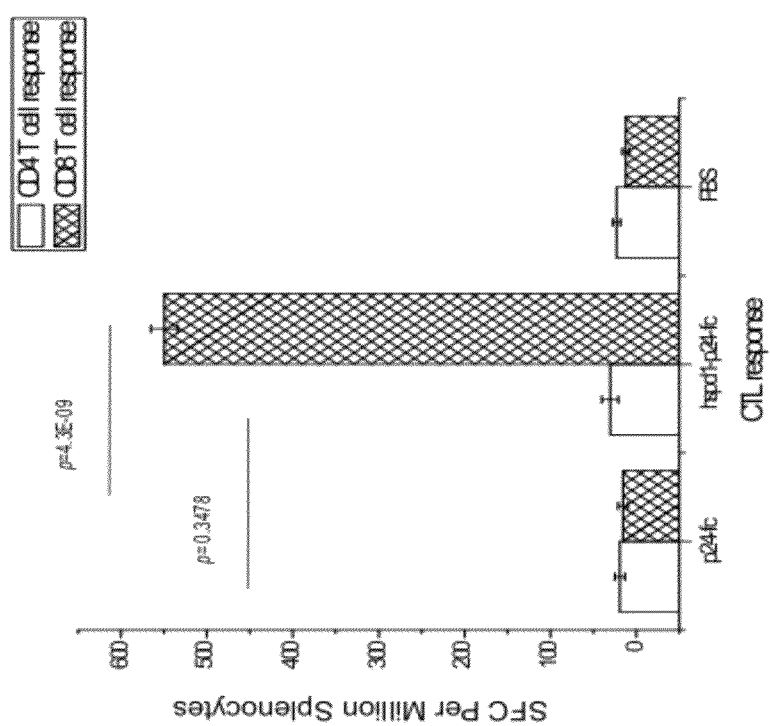
FIG. 6 shows that hspd1-p24-Fc elicits humoral and cell-mediated immune responses against HIV-1 p24. (A) shows that hsPD-1-p24-Fc binds to mouse PD-L1. (B) shows that hsPD-1-p24-Fc binds to mouse PD-L2. (C) shows high sera levels of anti-p24 IgG1 and IgG2a antibodies in mice immunized with hspd1-p24-Fc, when compared to mice immunized with p24-Fc. (D) shows the numbers of IFN-γ-secreting splenocytes specific for p24 epitope gagAI (AMQMLKDTI) (SEQ ID NO: 39) for CD8 T cells and the numbers of IFN-γ-secreting splenocytes specific for p24 epitope gag26 (TSNPPIPVGDIYKRWIILGL) (SEQ ID NO: 40) for CD4 T cells. Bars represent the average values of three samples (±standard deviations).
Figure 6C:
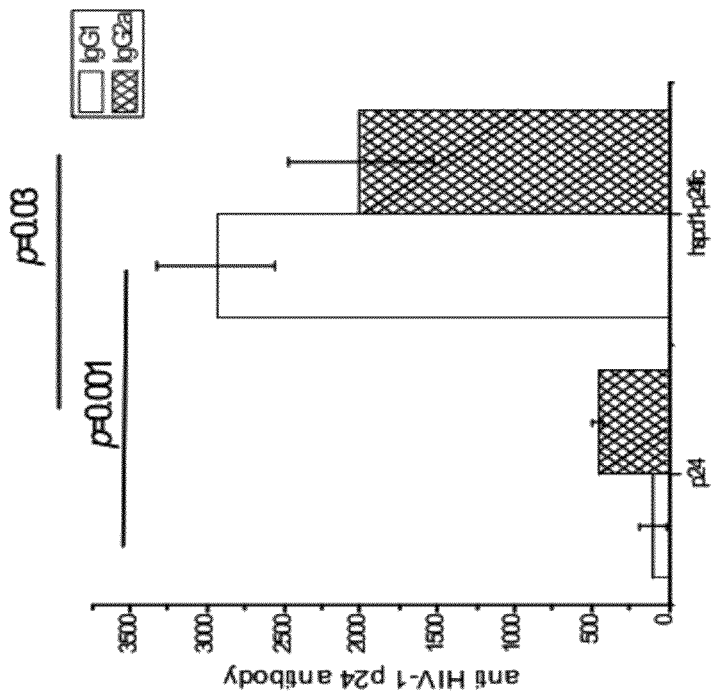

Two weeks after the last immunization, mice sera were collected. The levels of anti-p24 IgG1 and IgG2a antibodies were measured by ELISA. The levels of anti-p24 antibody in control samples is not shown because the absorbance readouts of these samples fell below the cutoff values for determining antibody titers. The anti-p24 antibody endpoint titer is defined as the reciprocal of the highest dilution of a test sample that produces a reading of at least two-fold greater than that of the control sample with the same dilution. The results, as shown in FIG. 6C, reveal that mice immunized with hspd1-p24-Fc had high IgG1 and IgG2a titers, when compared to mice immunized with p24-Fc.

To examine p24-specific immune response, the number of IFN-γ-secreting splenocytes specific for p24 epitope gagAI (AMQMLKDTI) (SEQ ID NO: 39) for CD8 T cells and the number of IFN-γ-secreting splenocytes specific for p24 epitope gag26 (TSNPPIPVGDIYKRWIILGL) (SEQ ID NO: 40) for CD4 T cells was determined by ELIspot assay. Bars represent the average values of three samples (±standard deviations). The results, as shown in FIG. 6D, reveal that wild-type hsPD1 (hspd1-p24-Fc) binds to mouse PD-L1 and PD-L2, and potently elicits humoral and cell-mediated immune responses.

Example 6

Construction of Mouse sPD-1 Variant Vaccine Candidates

This Example illustrates the construction of variant msPD-1 vaccine candidates. Mouse sPD1 variants, mspd1-

14del and mspd1-322mu, were constructed (FIG. 7A). The mspd1-14del variant is obtained by deleting amino acids 26-39 of the wild-type mspd1 (encoded by the first part of the second exon of the wild-type mouse PD-1 gene). The mspd1-322mu variant is obtained by changing amino acid residue 108 of the wild-type mouse PD-1 protein from Met to Val.

Mouse sPD-1 fusion constructs were obtained by fusing PVAX vector carrying mspd1 variant-p24 with rabbit Fc DNA. The PVAX vector and the p24-Fc DNA were linked by a linker encoding GGGSGGG (SEQ ID NO: 29). The transcription is under the control of promoter Pcmv.

Figure 7B:
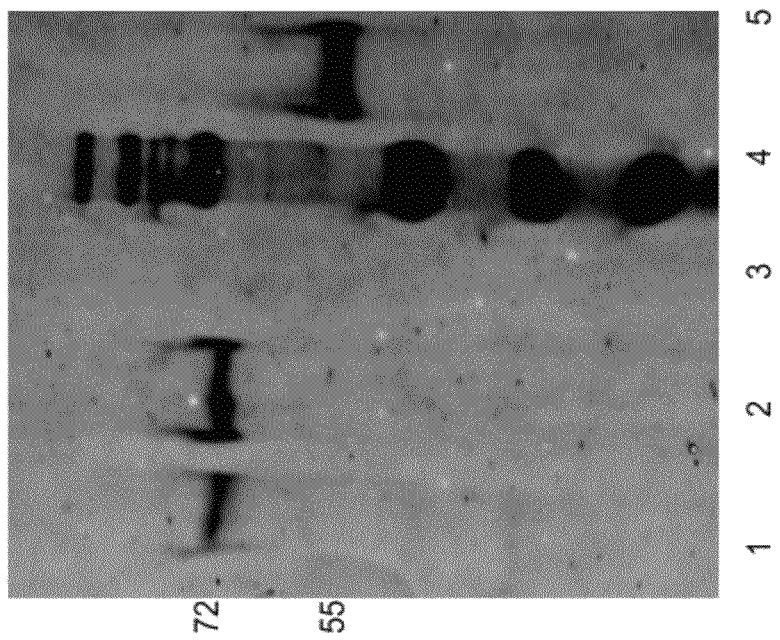
FIG. 7B shows Western blot analysis of mspd1-14del-p24-Fc, mspd1-322mu-p24-Fc, and p24-Fc. Proteins are detected by anti-rabbit Fc antibody.

FIG. 7A shows alignment of amino acid sequences of msPd1-p24-Fc, mspd1-14del-p24-Fc, mspd1-322mu-p24-Fc, and p24-Fc fusion proteins. FIG. 7B shows Western blot results of various fusion proteins useful according to the subject invention. Briefly, 293T cells were transfected with various fusion constructs using polyethylenimine (PEI) and the supernatants were collected 72 hours post transfection. Proteins were detected by anti-rabbit Fc antibody. FIG. 7B shows that mspd1-14del-p24-Fc, and mspd1-322mu-p24-Fc are about 72 KD in size, while p24-Fc is about 50 KD in size. The results also show that mspd1-14del-p24-Fc, and mspd1-322mu-p24-Fc fusion proteins are soluble.

Example 7

Binding Ability of Mouse sPD-1 Variant Fusion Proteins to sPD-1 Ligands

This Example shows that msPD-1 variant fusion proteins, mspd1-14del-p24-Fc and mspd1-322mu-p24-Fc, do not bind to mouse sPD-1 ligands PD-L1 and PD-L2 (FIG. 8). Briefly, 293T cells were transfected with PD-L (PD-L1 and PD-L2). The binding of sPD-1 proteins to PD-1 ligands was detected by mouse sPD-1-p24-Fc proteins and FITC-anti rabbit Fc antibody using flow cytometer, and the results were analyzed by flowJo.

Example 8

Induction of Humoral and Cell-Mediated Immune Responses by Variant sPD 1 Vaccines This Example shows that msPD 1 variants potently elicit humoral and cell-mediated immune responses. Briefly, Balb/c mice were primed at week 0 and boosted at week 3 and week 6 with 20 μg mouse DNA vectors encoding mspd1-14del-p24-Fc, mspd1-322mu-p24-Fc, or p24-Fc via intramuscular electroporation. Mice that received PBS served as controls.

Two weeks after the last immunization, mice sera were collected. The levels of anti-p24 IgG1 and IgG2a antibodies were measured by ELISA. The level of anti-p24 antibody in control samples is not shown because the absorbance readouts of these samples fell below the cutoff values for determining antibody titers. The anti-p24 antibody endpoint titer is defined as the reciprocal of the highest dilution of a test sample that produces a reading of at least two-fold greater than that of the control sample with the same dilution. The results show that mice immunized with mspd1-14del-p24-Fc or mspd1-322mu-p24-Fc had high IgG1 and IgG2a titers, when compared to mice immunized with p24-Fc.

To examine p24-specific immune response, the number of IFN-γ-secreting splenocytes specific for p24 epitope gagAI (AMQMLKDTI) (SEQ ID NO: 39) for CD8 T cells and the number of IFN-γ-secreting splenocytes specific for p24 epitope gag26 (TSNPPIPVGDIYKRWIILGL) (SEQ ID NO: 40) for CD4 T cells was determined by ELIspot assay.

Figure 9A:
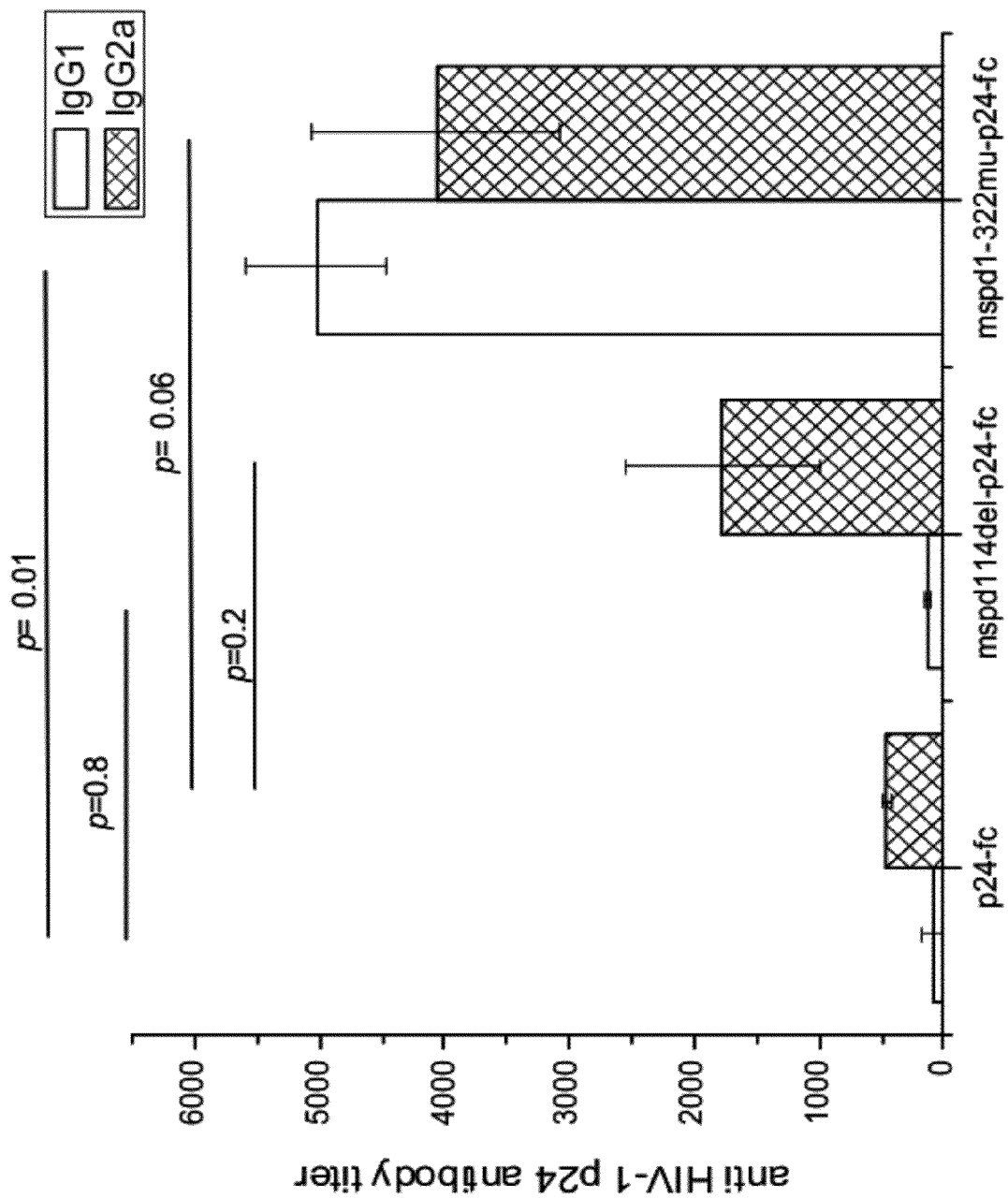
FIG. 9 shows that variant sPD1 DNA elicits humoral and cell-mediated immune responses against HIV p24. (A) shows serum levels of anti-p24 IgG1 and IgG2a antibodies in mice immunized with mspd1-14del-p24-Fc, mspd1-322mu-p24-Fc, and p24-Fc fusion DNA, respectively. Bars represent the average values of three samples (±standard deviations). (B) shows the number of IFN-γ-secreting splenocytes specific for p24 epitope gagAI (AMQMLKDTI) (SEQ ID NO: 39) for CD8 T cells. Bars represent the average values of three samples (±standard deviations). (C) shows images of splenocytes isolated from immunized mice. To analyze p24-specific immune response, splenocytes were stained with H2d-Kd-gagAI-PE tetramer for CD8 T cell population analysis. (D) shows the number of IFN-γ-secreting splenocytes specific for p24 epitope gag26 (TSNPPIPVGDIYKRWIILGL) (SEQ ID NO: 40) for CD4 T cells. Bars represent the average values of three samples (±standard deviations). Data represent three experiments on the same batch of immunized mice.
Figure 9B:
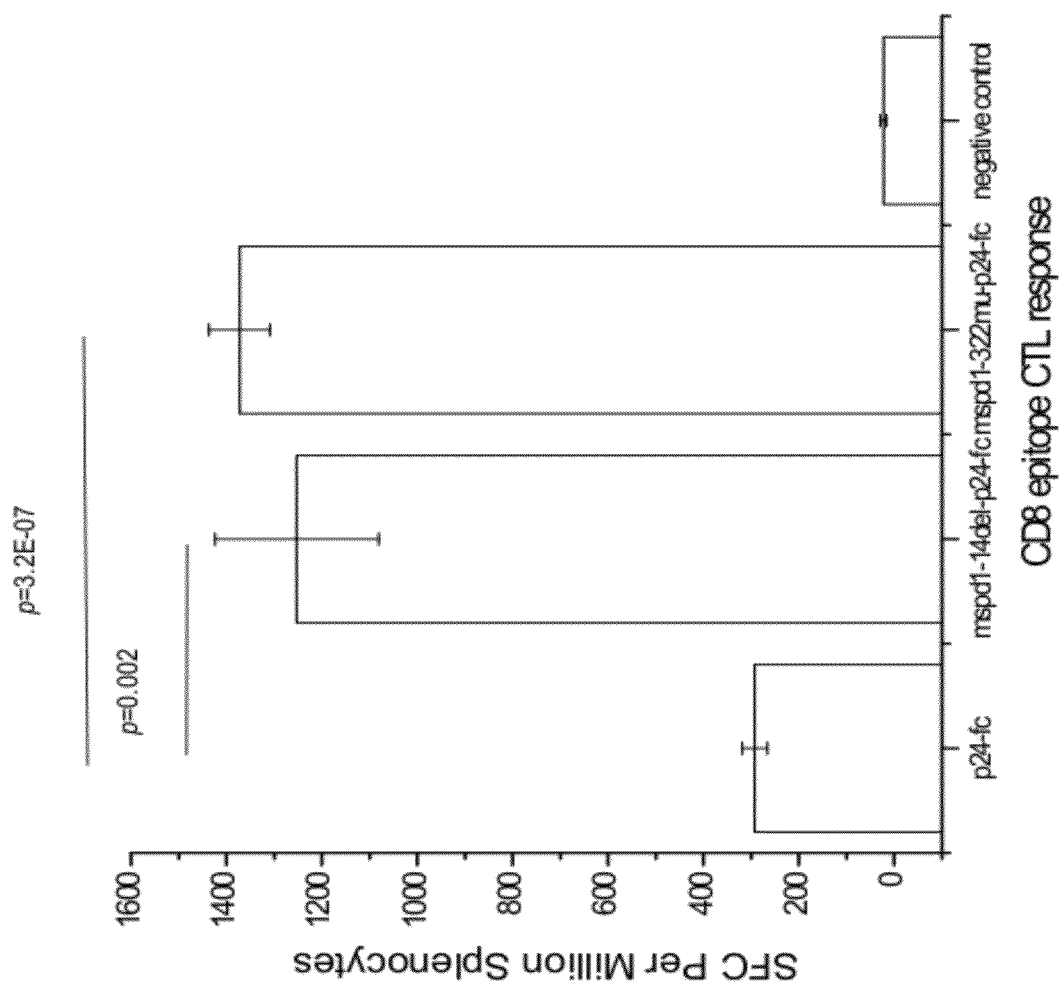
Figure 9C:
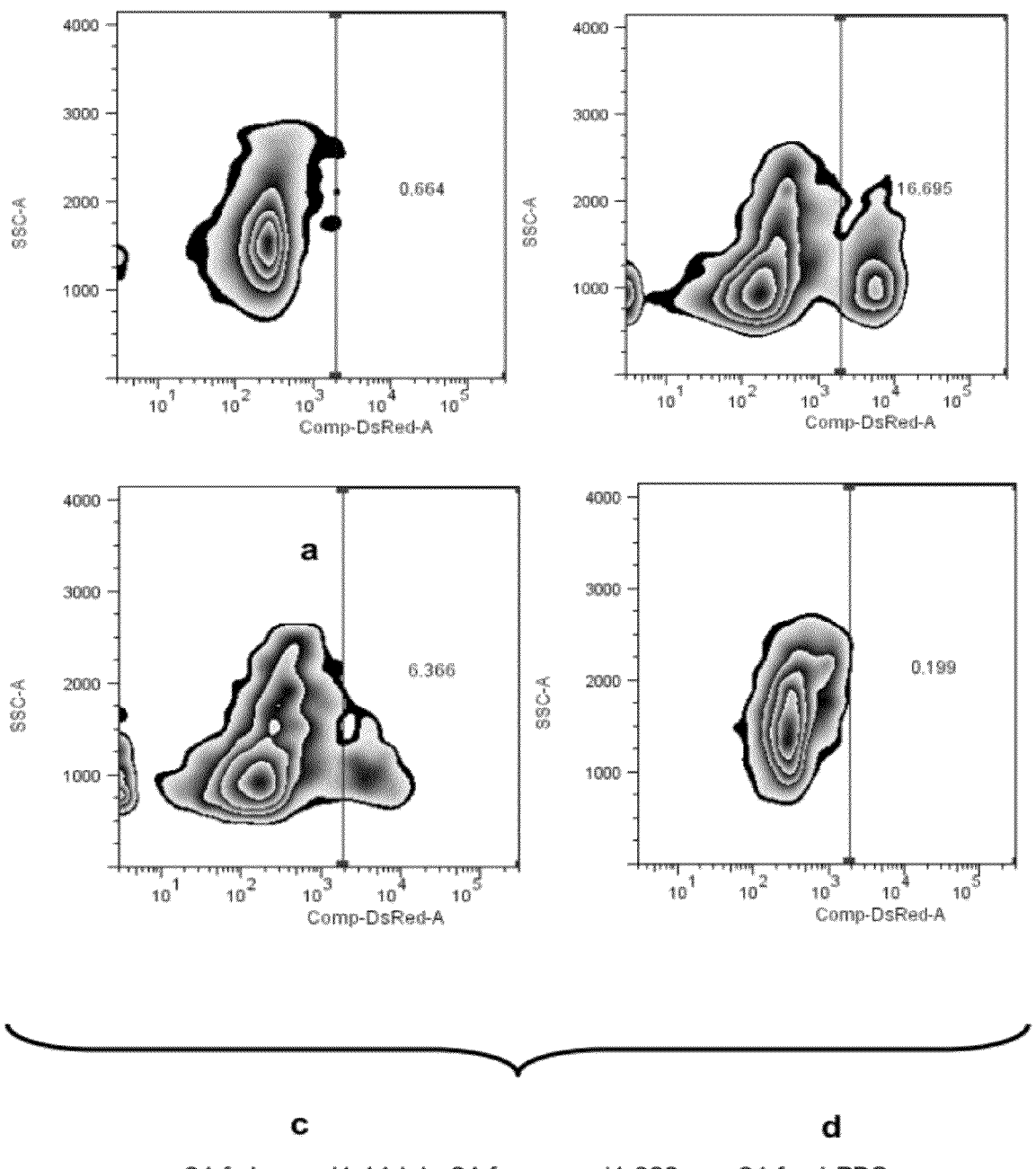
Figure 9D:
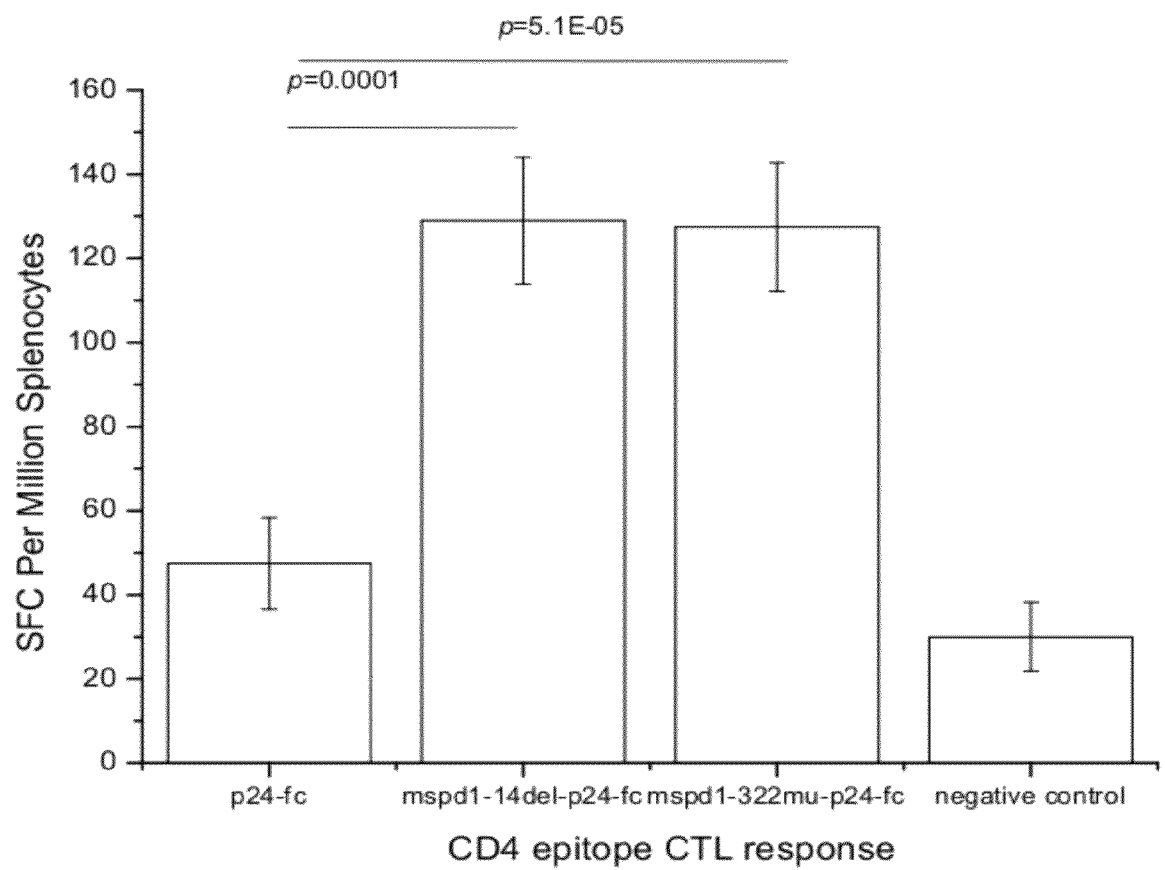
Figure 10:
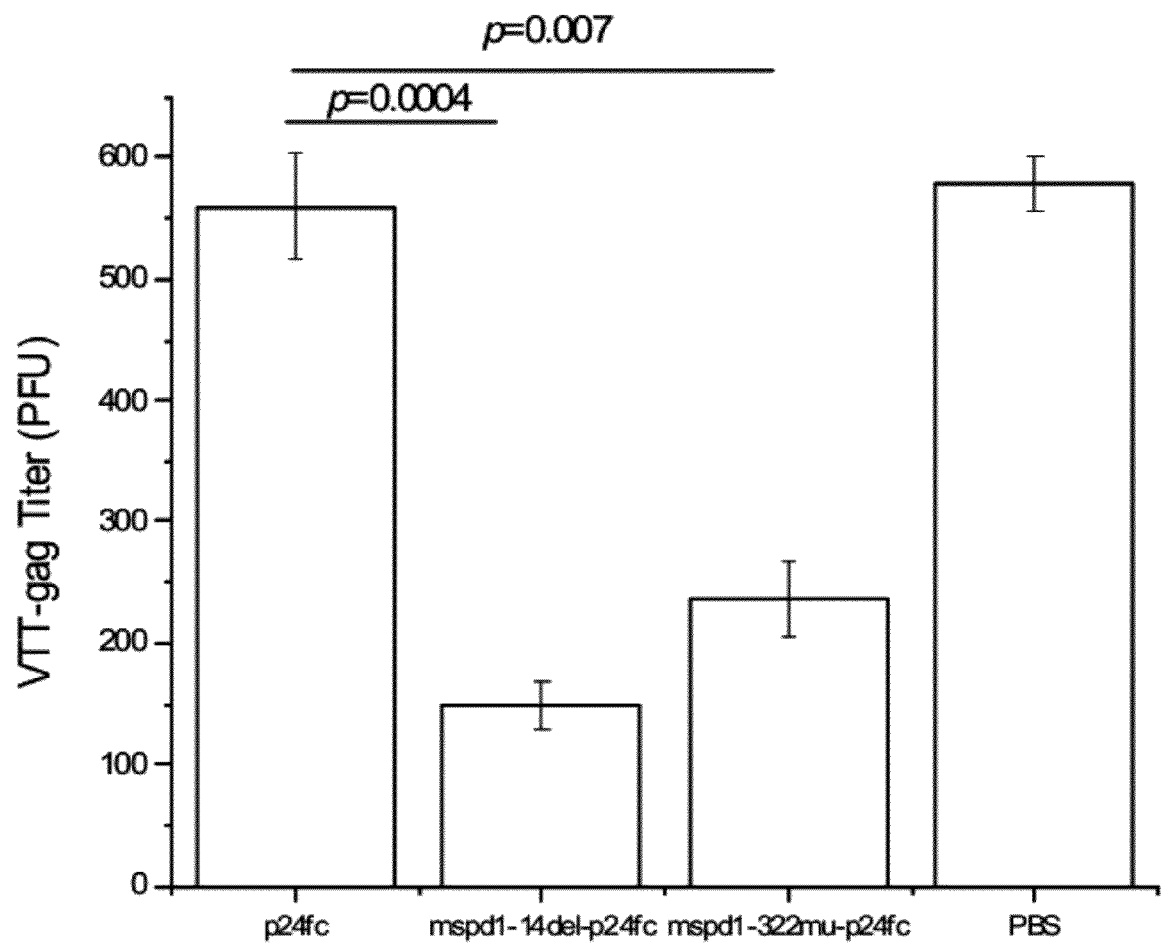
FIG. 10 shows that immunization with variant msPD1 fusion DNA protects mice against viral infection. Balb/c mice immunized with mspd1-14del-p24-Fc, mspd1-322mu-p24-Fc, and p24-Fc fusion DNA were challenged with $4 \times 10^7$ PFU of vaccinia VTT-HIV-gagpol intranasally three weeks after the last immunization. The mice were sacrificed 3 days after viral challenge. Viral titers in lungs were evaluated by plaque-forming assay in Vero cells. Bars represent the average values of five samples (±standard deviations).

The results show that mice immunized with mspd1-14del-p24-Fc or mspd1-322mu-p24-Fc had high anti-p24 antibody titers (FIG. 9A) and high number of IFN-γ-secreting splenocytes (FIGS. 9B and 9D). Splenocytes isolated from mice immunized with mspd1-14del-p24-Fc or mspd1-322mu-p24-Fc contained higher H2d-Kd gagAI tetramer-positive cells (FIG. 9C), when compared to mice immunized with p24-Fc.

Example 9

Figure 11A:
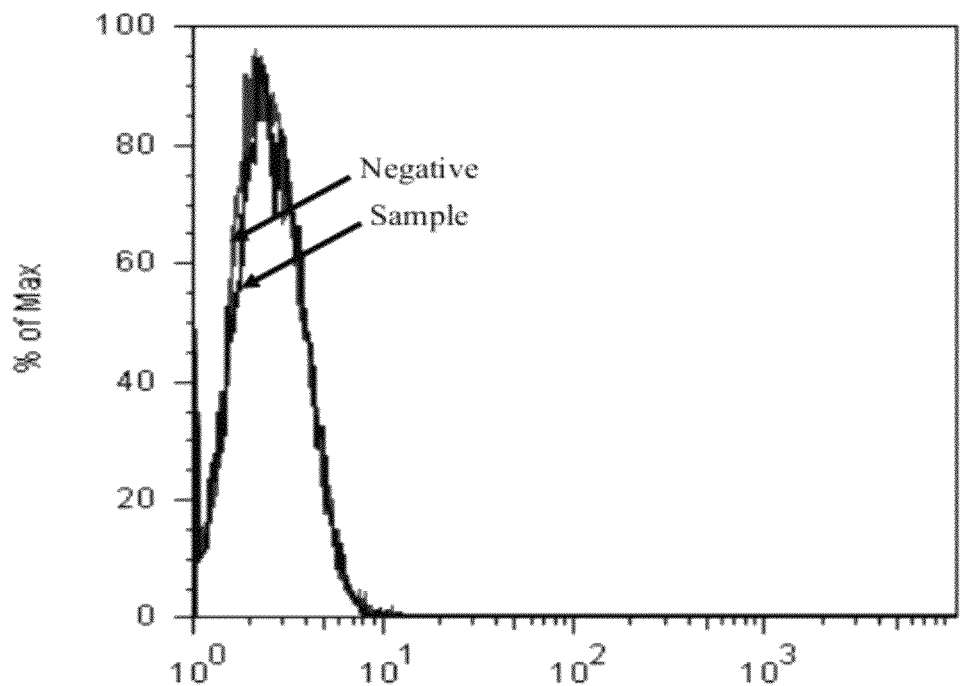
FIG. 11 shows that hspd1-14del-p24-Fc elicits humoral and cell-mediated immune responses against HIV-1 p24. (A) shows that hspd1-14del-p24-Fc does not bind to mouse PD-L1. (B) shows that hspd1-14del-p24-Fc does not bind to mouse PD-L2. (C) shows high sera levels of anti-p24 IgG1 and IgG2a antibodies in mice immunized with hspd1-14del-p24-Fc, when compared to mice immunized with p24-Fc. (D) shows the numbers of IFN-γ-secreting splenocytes specific for p24 epitope gagAI (AMQMLKDTI) (SEQ ID NO: 39) for CD8 T cells and the numbers of IFN-γ-secreting splenocytes specific for p24 epitope gag26 (TSNPPIPVGDIYKRWIILGL) (SEQ ID NO: 40) for CD4 T cells. Bars represent the average values of three samples (±standard deviations).
Figure 11B:
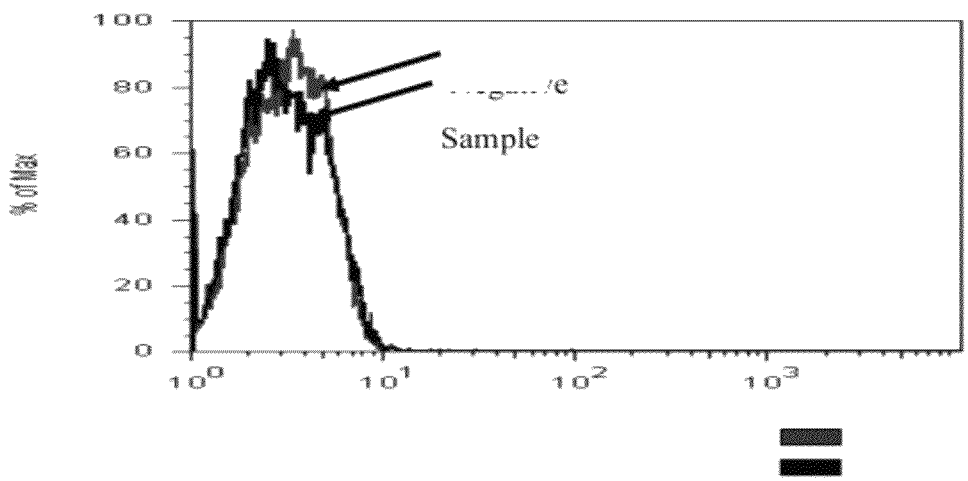
Figure 11C:
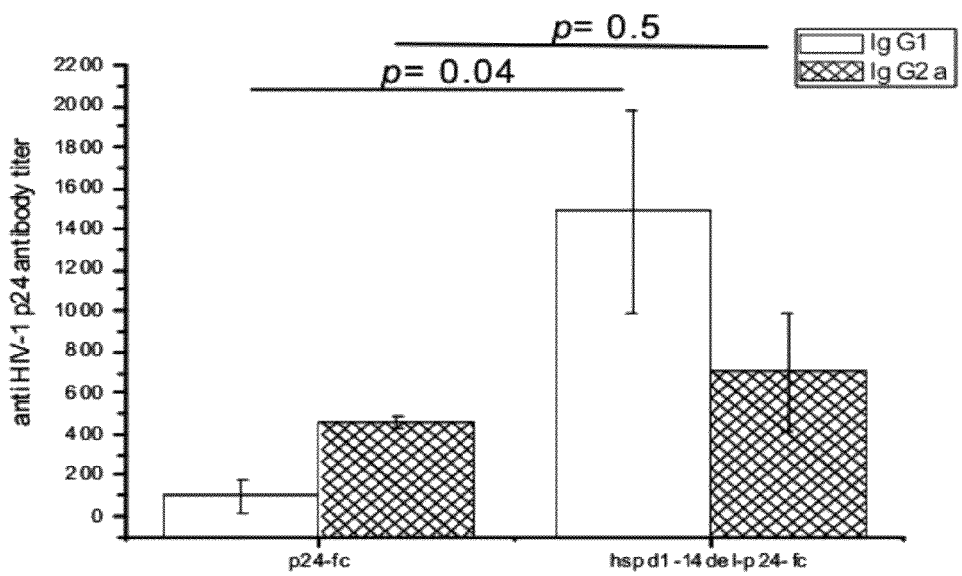
Figure 11D:
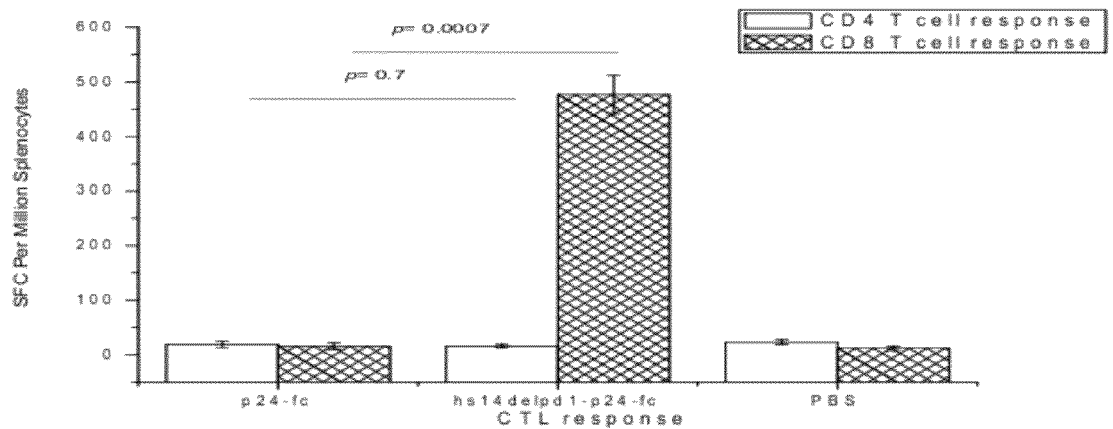
Figure 12:
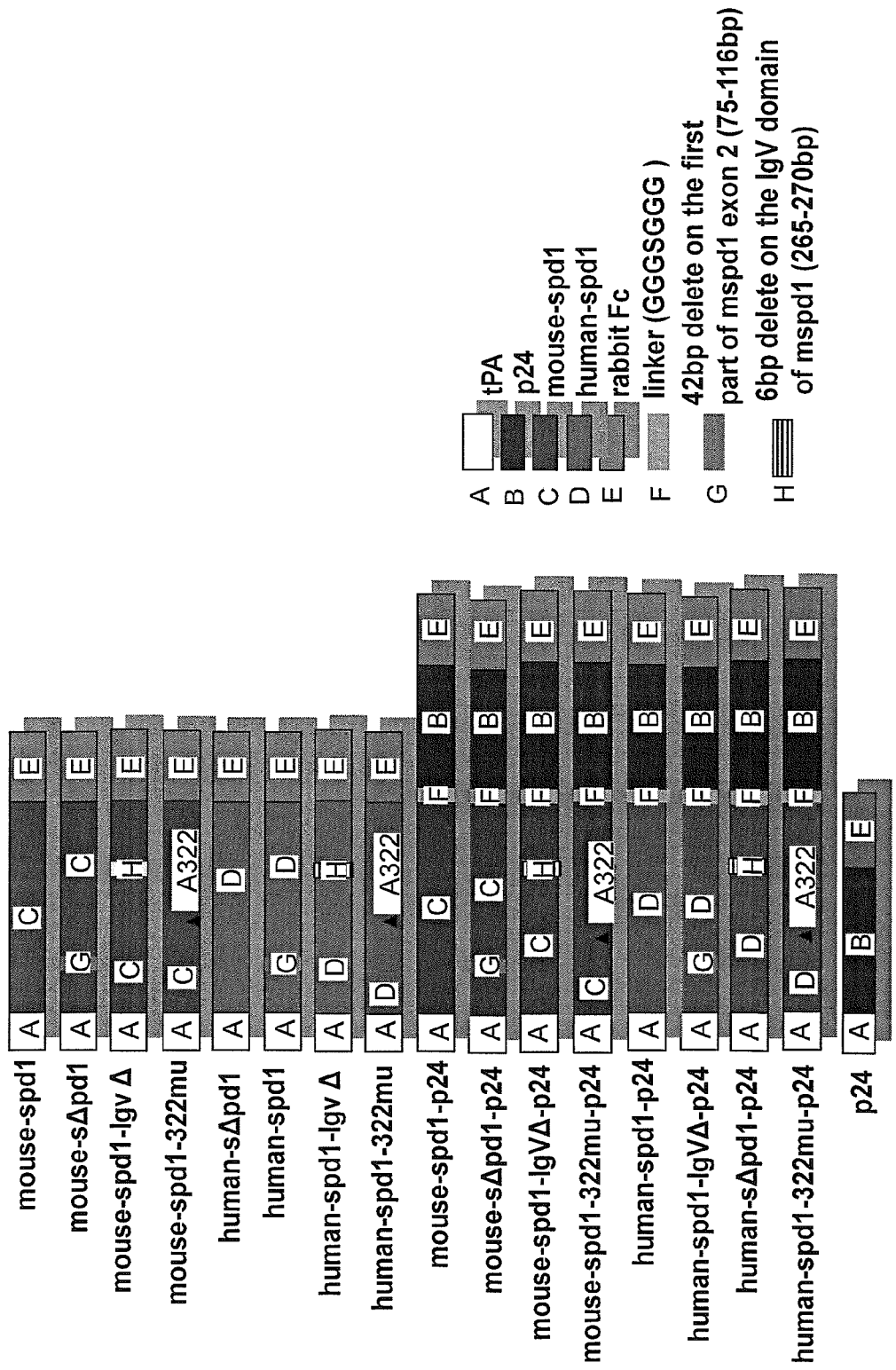
FIG. 12 shows the structures of various clones useful according to the subject invention.

Reduction of VTT-HIV-Gagpol Titers in Mice Immunized with Variant Mouse sPD 1 Fusion Proteins This Example shows that immunization with variant mspd1-14del-p24-Fc or mspd1-322mu-p24-Fc protects against HIV infection. Briefly, Balb/c mice were primed at week 0 and boosted at week 3 and week 6 with 20 μg mouse DNA encoding mspd1-14del-p24-fc or mspd1-322mu-p24-Fc via intramuscular electroporation. Three weeks after immunization, mice were challenged with $4\times10^7$PFU of VTT-HIV-gagpol intranasally. Mice that received PBS served as controls.

The mice were sacrificed 3 days after viral challenge and viral titers in lungs were evaluated by plaque assay. The results show that mice immunized with mspd1-14del-p24-Fc or mspd1-322mu-p24-Fc exhibited significantly reduced VTT-HIV-gagpol titers upon viral challenge (FIG. 10).

Example 10

Induction of Humoral and Cell-Mediated Immune Responses by Variant Human sPD1 Vaccine In this Example, variant hsPD1 construct, hsPD1-14del-p24-Fc, was constructed. To analyze the binding ability of hsPD1-14del-p24-Fc protein to mouse PD-L1 and PD-L2, 293T cells were transfected with PD-L1 and PD-L2, respectively. The binding of hsPD1-14del-p24-Fc protein to PD-1 were detected by FITC-anti rabbit Fc antibody using flow cytometer, and the results were analyzed by flowJo. The results, as shown in FIGS. 11A and 11B, reveal that hspd1-p24-Fc fusion protein binds to PD-1 ligands.

To examine the induction of immune responses by hsPD1-14del-p24-Fc, Balb/c mice were primed at week 0 and boosted at week 3 and week 6 with 20 μm/mice DNA encoding hsPD1-14del-p24-Fc or p24-Fc via intramuscular electroporation. Mice that received PBS served as controls.

Two weeks after the last immunization, mice sera were collected. The levels of anti-p24 IgG1 and IgG2a antibodies were determined by ELISA. The levels of anti-p24 antibody in control samples are not shown because the absorbance readouts of these samples fell below the cutoff values for determining antibody titers. The anti-p24 antibody endpoint titer is defined as the reciprocal of the highest dilution of a test sample that produces a reading of at least two-fold greater than that of the control sample with the same dilution.

To examine p24-specific immune response, the number of IFN-γ-secreting splenocytes specific for p24 epitope gagAI (AMQMLKDTI) (SEQ ID NO: 39) for CD8 T cells and the number of IFN-γ-secreting splenocytes specific for p24 epitope gag26 (TSNPPIPVGDIYKRWIILGL) (SEQ ID NO: 40) for CD4 T cells was determined by ELIspot assay. Although hspd1-14del-p24-Fc protein does not bind to PD-1, the results show that hspd1-14del-p24-Fc significantly enhanced humoral and cell-mediated immune responses upon HIV viral challenge (FIGS. 11C and 11D).

Example 11

Antigen Targeting to Dendritic Cells by sPD-1-Based Vaccine Amplifies CD8+ T Cell Immunity This Example shows that sPD-1-based vaccine improves CD8+ T cell immunity by targeting vaccine antigens to dendritic cells (DCs), while blocking the negative effects of the PD-1/PD-L pathway on T cell function simultaneously.

Figure 16A:
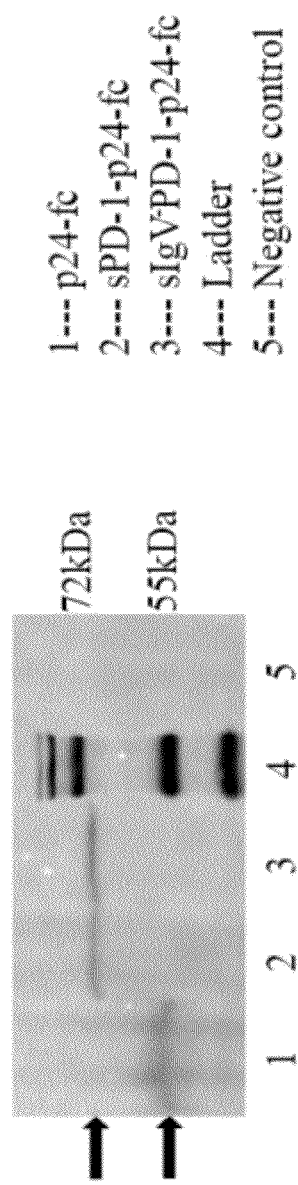
FIG. 16 shows expression and binding characteristics of DNA vaccine constructs. (A) DNA vaccines encoding sPD-1, the mutated form sIgV-PD-1, p24 and fc were tested for protein expression by Western blotting. Lower sized band represents p24-fc, while the higher sized band represents sPD-1-p24-fc or sIgV-PD-1-p24-fc. (B) 293T cells were transiently transfected with PD-L1 or PD-L2 expression vectors, and the binding profiles of recombinant proteins were examined. Flow cytometric signals were obtained by treating the cells with purified proteins from the constructs followed by detection using anti-rabbit Fc-FITC antibody. Controls included transfected 293T cells stained with anti-rabbit Fc-FITC antibody (negative, shaded) or anti-mouse PD-L1 or L2 antibodies (positive, solid line, not shaded).

HIV-1 Gag p24 was chosen as a test antigen because it has been commonly used in other DC targeting strategies as a model immunogen[7,8]. Three DNA vaccines, p24-fc, sPD-1-p24-fc, and sIgV-PD-1-p24-fc, were designed (FIGS. 13a and 16a). sIgV-PD-1-p24-fc differs from sPD-1-p24-fc by two essential amino acids in the functional IgV domain of sPD-1, rendering it unable to bind PD-1 ligands14.

Figure 16B:
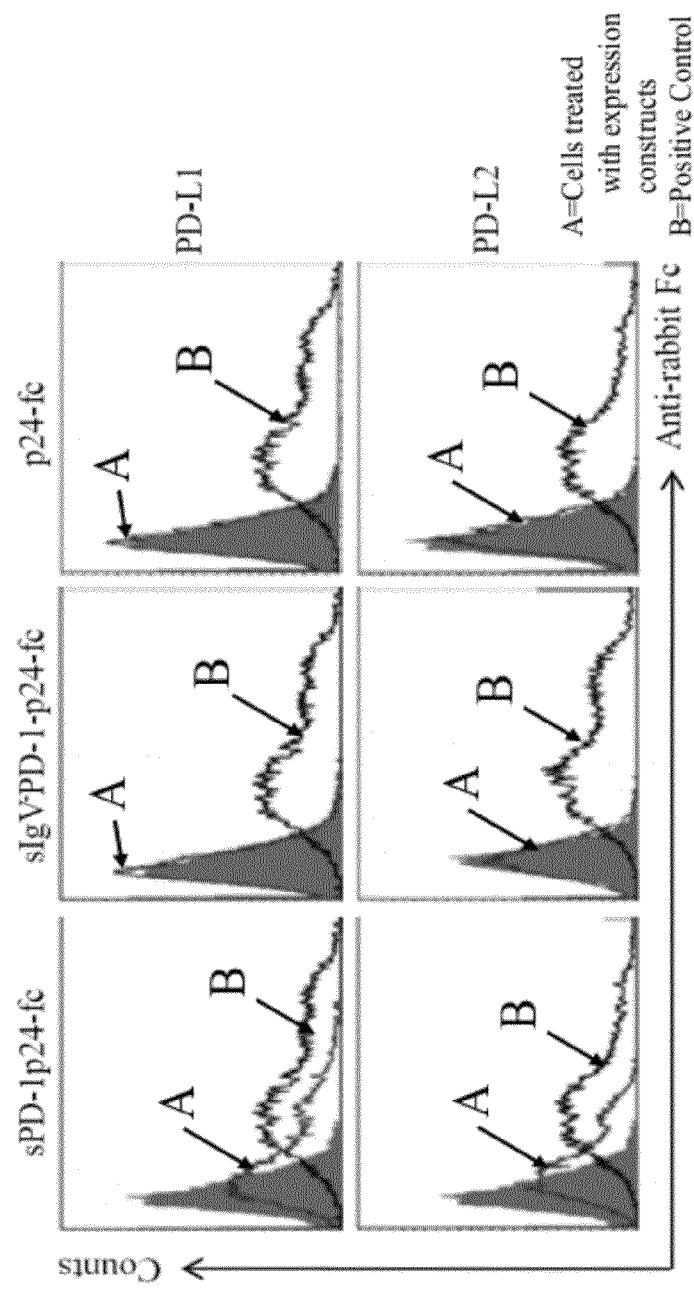

The results show that PD-L1 and PD-L2 interact with recombinant sPD-1-p24-fc protein, but do not interact with sIgV-PD-1-p24-fc or p24-fc proteins (FIG. 16b).

Figure 17A:
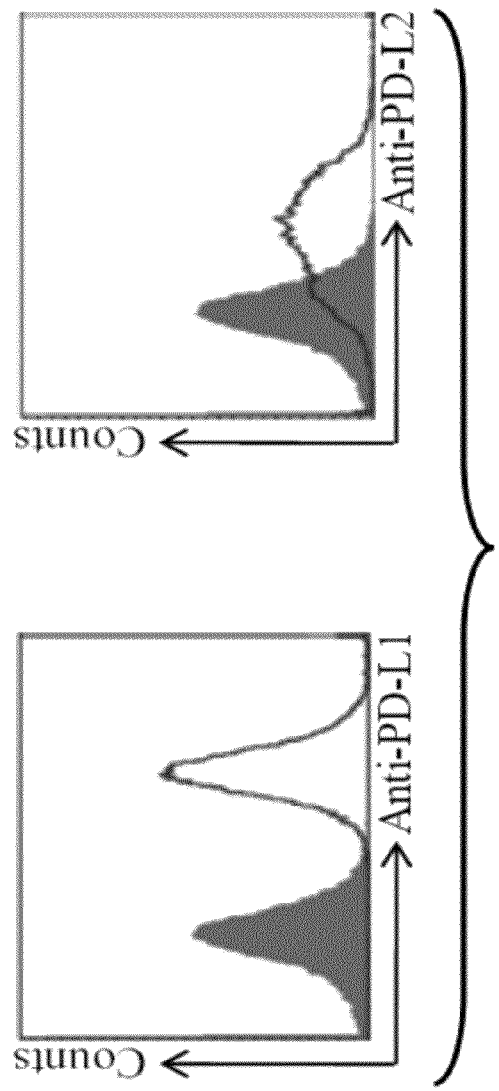
FIG. 17 shows that targeting dendritic cells (DCs) using sPD-1-p24-fc induces enhanced p24-specific antibody and T cell responses. (A) Expression of PD-L1 and PD-L2 on purified CD11c+BM-DCs isolated from Balb/c mice was confirmed by flow cytometric analysis using anti-mouse PD-L1 or L2 antibodies (solid line, not shaded). Cells stained with isotype antibody control are shown as shaded histogram. (B) BM-DCs treated with purified sPD-1-p24-fc and sIgV-PD-1-p24-fc proteins to examine binding. Proteins bound to DCs were detected by flow cytometry using an anti-rabbit Fc-FITC antibody (solid line, not shaded) in parallel to DCs without treatment of proteins as negative control (shaded). 2×10⁶ DCs treated with 20 μg of sPD-1-p24-fc or sIgV-PD-1-p24-fc proteins were introduced to Balb/c mouse by tail vein injection once every three weeks for a total experimental duration of six weeks. Mice that received untreated CD11c⁺ DCs served as control. (C) Mice sera were collected and analyzed for the presence of IgG1 and IgG2a antibodies specific against HIV-1 p24 by ELISA. (D) IFN-γ producing CD8⁺ and CD4⁺ cells were measured by ELISpot assay in mice splenocytes stimulated using specific peptides gagAI and gag26, respectively. H2-Kd gagAI-PE tetramer staining was performed on isolated splenocytes and analyzed by flow cytometry as a column graph of data from groups of immunized mice (F). Bars represent the mean values of two replicate mice with standard error depicted by error bars. Data are representative of two independent immunization experiments. *P<0.05.
Figure 17B:
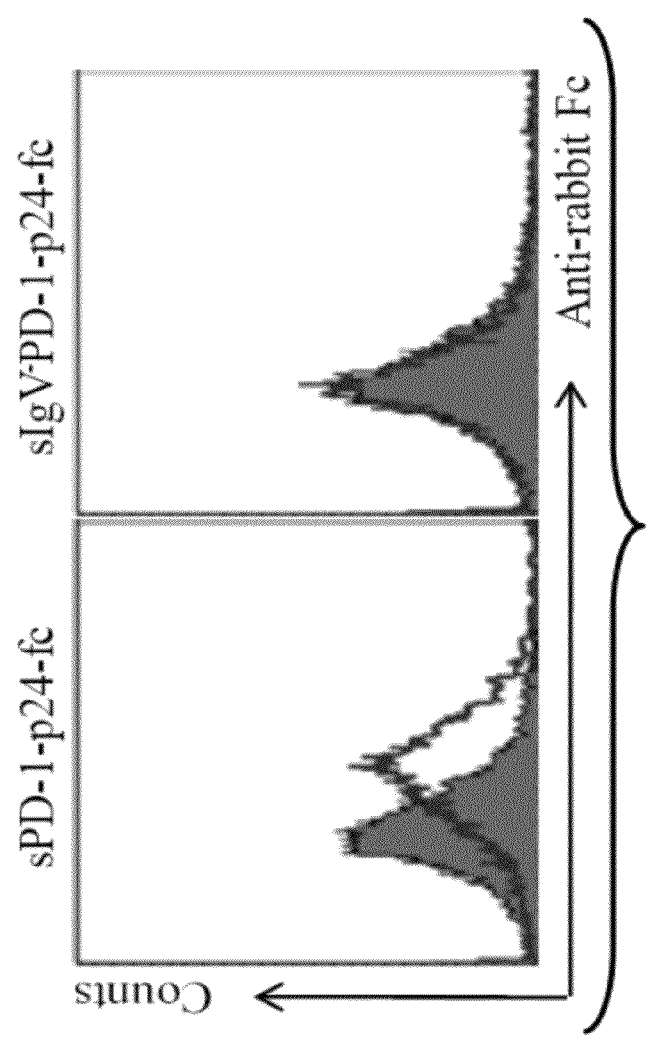

In addition, Balb/c mice bone marrow (BM) derived CD11c+DCs that expresses PD-L1 and PD-L2 (FIG. 17a) binds to sPD-1-p24-fc, but does not bind to sIgV-PD-1-p24-fc (FIG. 17b).

Figures 13A, 13B:
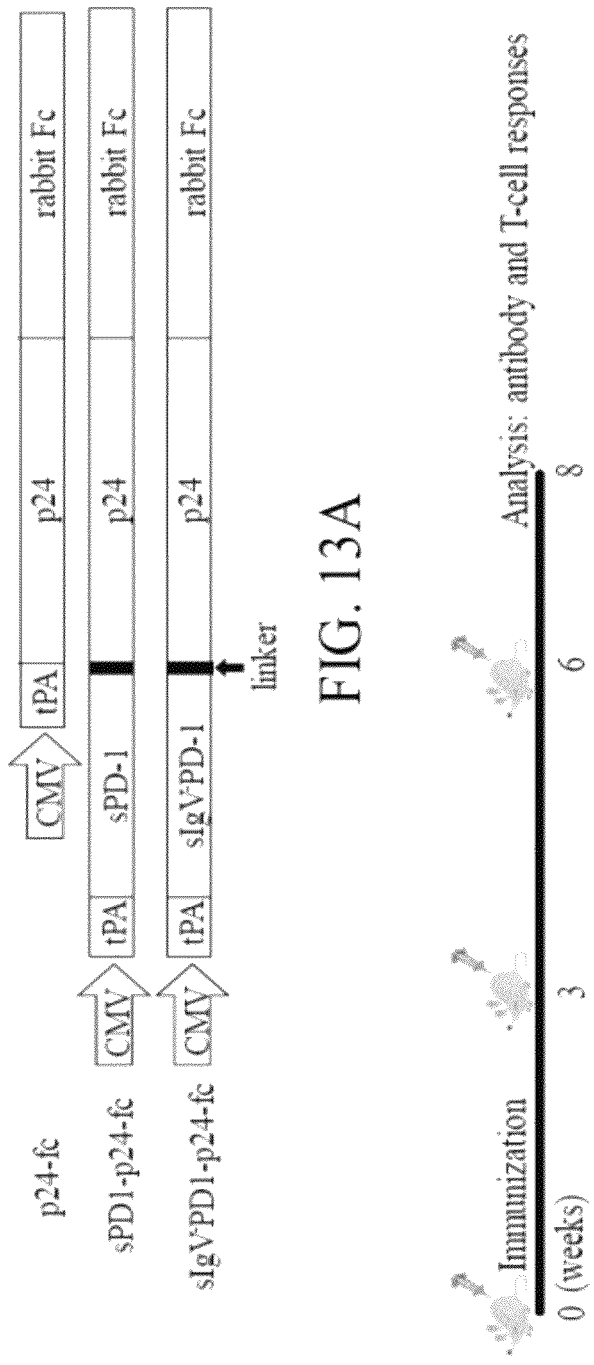
FIG. 13 shows the induction of potent p24-specific immune responses by sPD-1-p24-fc vaccination. (A) Schematic representation of constructs encompassing the soluble form of PD-1 or with two amino acid deletions essential for binding with PD-L1/L2 (sIgV-PD-1), p24 and rabbit Fc under the CMV promoter. Rabbit Fc was used as a tag for purification purposes. (B) Mouse immunization schedule is depicted. Balb/c mice were immunized with sPD1-p24-fc, sIgV-PD-1-p24-fc and p24-fc at week 0, 3 and 6 at a low dose of 20 μg or a high dose of 100 μg i.m. with EP. Mice that received PBS only served as a negative control. Mice sera and splenocytes were collected two weeks after the final immunization for analysis of antibody and T cell responses, respectively. (C) Detection of specific IgG1 and IgG2a antibodies against HIV-1 Gag p24 by ELISA two weeks post immunization. (D) Number of IFN-γ-secreting CD8$^+$ and (E) CD4$^+$ T cells measured by ELISpot in specific response to HIV-1 Gag p24 epitopes gagAI and gag26, respectively. (F) IFN-γ$^+$ secreting cells in response to stimulation using three different peptide pools derived from 59 peptides that spans the whole HIV-1 Gag p24. (G) Representative H2-Kd gagAI-PE tetramer staining of CD8$^+$ T cell population is shown in flow cytometric plots or data amalgamated into a column graph (H). Data are representative of three independent immunization experiments. *P<0.05, P<0.01, *P<0.001.

$2 \times 10^6$ BM-DCs were pulsed with 20 µg sPD-1-p24-fc or control proteins, and infused back into Balb/c mice via the tail vein in accordance to a standard immunization schedule[15,16] (FIG. 13b). Compared to sIgV-PD-1-p24-fc, sPD-1-p24-fc-pulsed BM-DCs elicited higher levels of anti-p24 IgG1 (Th2) and IgG2a (Th1) antibody responses (p<0.05; FIG. 17c). Increased levels of p24-specific CD8+ T cell immunity was also evident as determined by IFN-γ ELISpot (FIG. 17d) and H2-Kd gagAI tetramer assays[17,18] (FIG. 17e). The results show that the sPD-1-based protein vaccine induced p24 specific CD8+ T cell immunity by targeting dendritic cells.

The results also show that sPD-1-p24-fc can be used as a DNA vaccine against infection. The present inventions have previously shown that intramuscular (i.m.)/EP enhances the immunogenicity of DNA vaccines consistently[13,19,20].

Figures 13C, 13D:
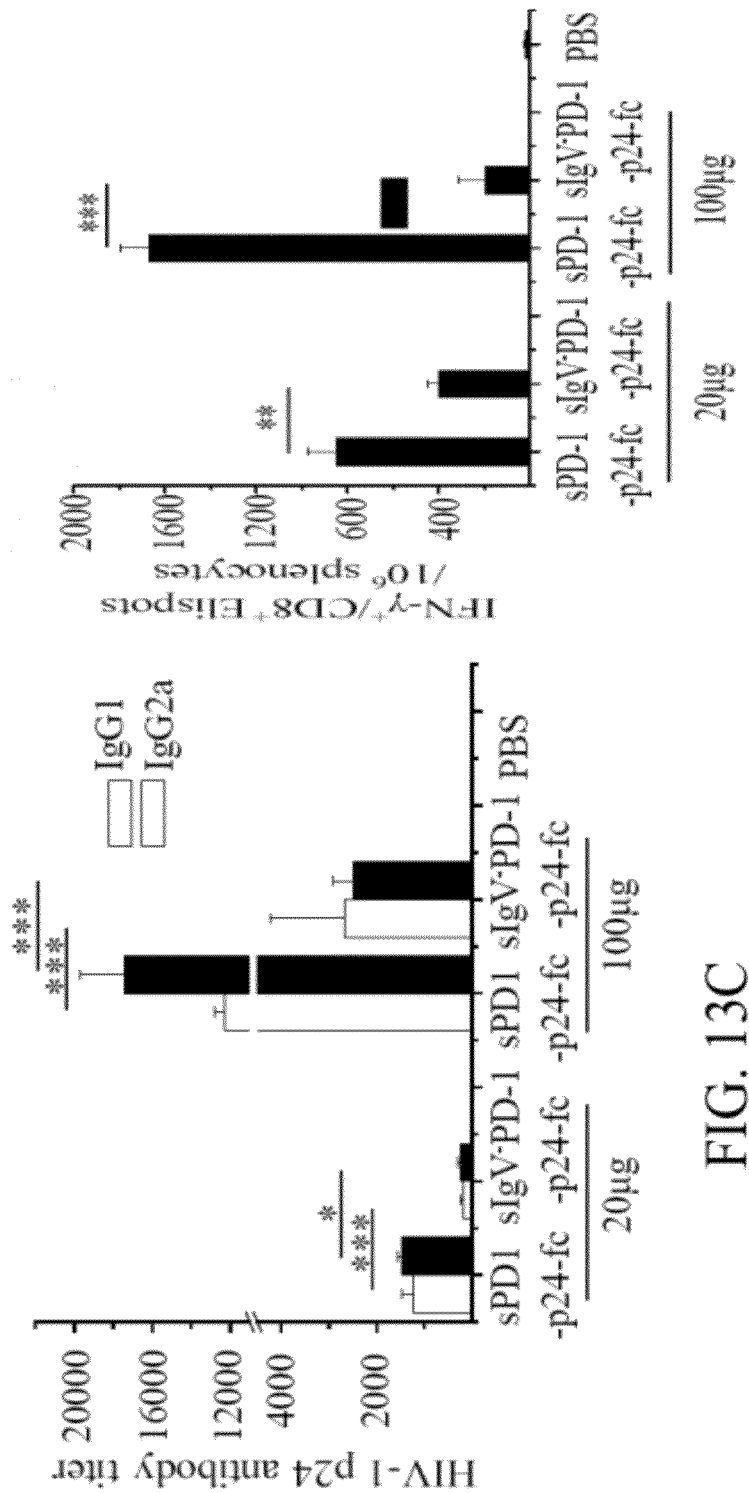
Figures 13E, 13F:
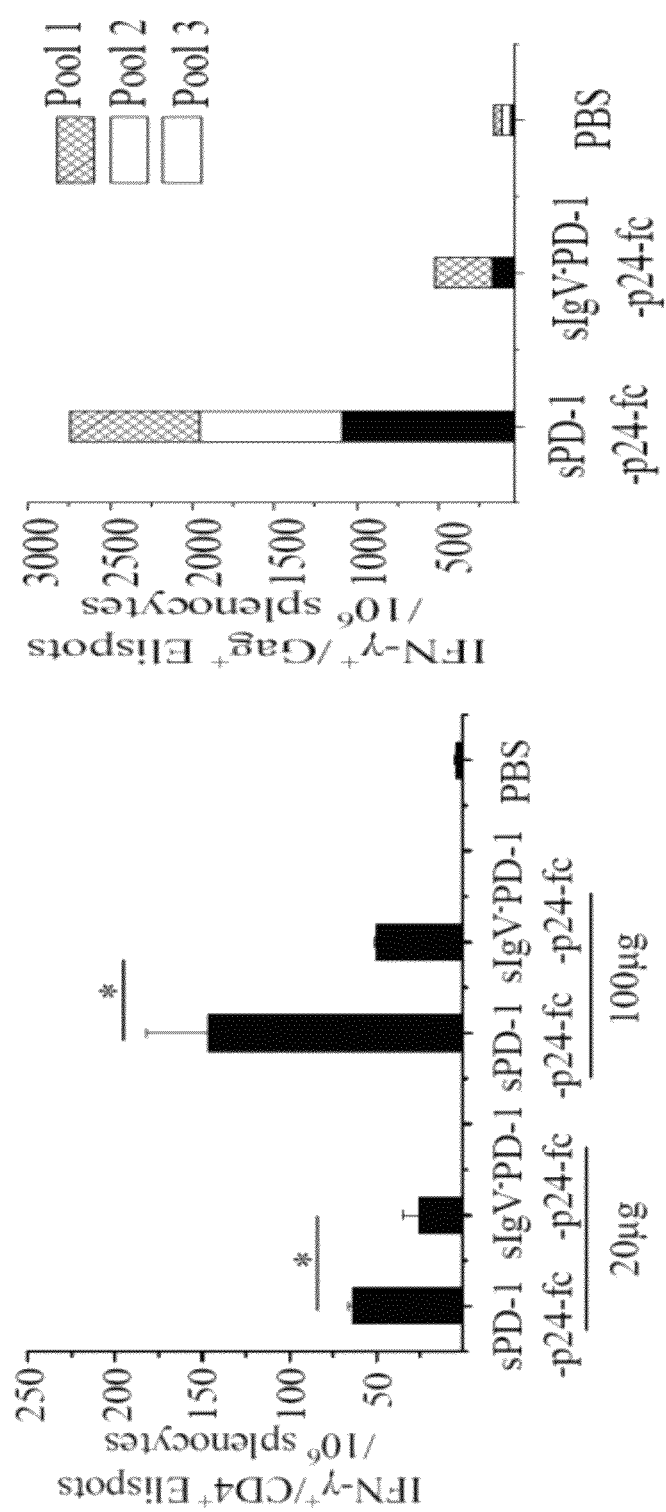

In this Example, i.m. sPD-1-p24-fc/EP vaccination was conducted, using a vaccine dose of 20 µg or 100 µg (FIG. 13b). The results show that sPD-1-p24-fc/EP elicited significantly higher levels of IgG1 (4-fold; p<0.01) and IgG2a (8-fold; p<0.01) antibody responses, when compared to the sIgV-PD-1-p24-fc/EP control (FIG. 13c), in addition to potent and dose-dependent anti-Gag CD8+ (p<0.001) and CD4+ (p<0.05)T cell responses as determined by IFN-γ+ ELISpots (FIGS. 13d and 13e). Specifically, approximately 700 and 1600 ELISpots/$10^6$ splenocytes were found against the CD8−-specific Gag-AI epitope at the doses 20 µg and 100 µg, respectively. This greatly contrasts with the 200-300 ELISpots/$10^6$ splenocytes against the same epitope elicited by 1 mg/i.m. ADVAX (a codon-optimized HIV DNA vaccine) or $10^6$ TCID50/i.m. ADMVA (a vaccinia MVA-vectored HIV-1 vaccine) as previously described by the present inventors[15,16].

The p24-specific T cell immunity was not confined to the single Gag-AI epitope. Approximately 800-1000 ELISpots/106 splenocytes was reactive to each of the three non-overlapping peptide pools spanning the entire p24 protein, indicating a broad breadth in anti-Gag Gag T cell responses following vaccination with sPD-1-p24-fc/EP (FIG. 13F). Additionally, over 12.7% and 22% of CD8+ T cells were positive for H2-Kd-Gag-AI tetramer binding in the 20 µg and 100 µg sPD-1-p24-fc/EP dose groups respectively, which is significantly higher than that of the sIgV-PD-1-p24-fc/EP group (p<0.05, FIGS. 3g and 13h), and is comparable to those observed in Balb/c mice using a heterologous prime-boost protocol with two live vectors, L. monocytogenes and Ad5[18].

Figure 14A:
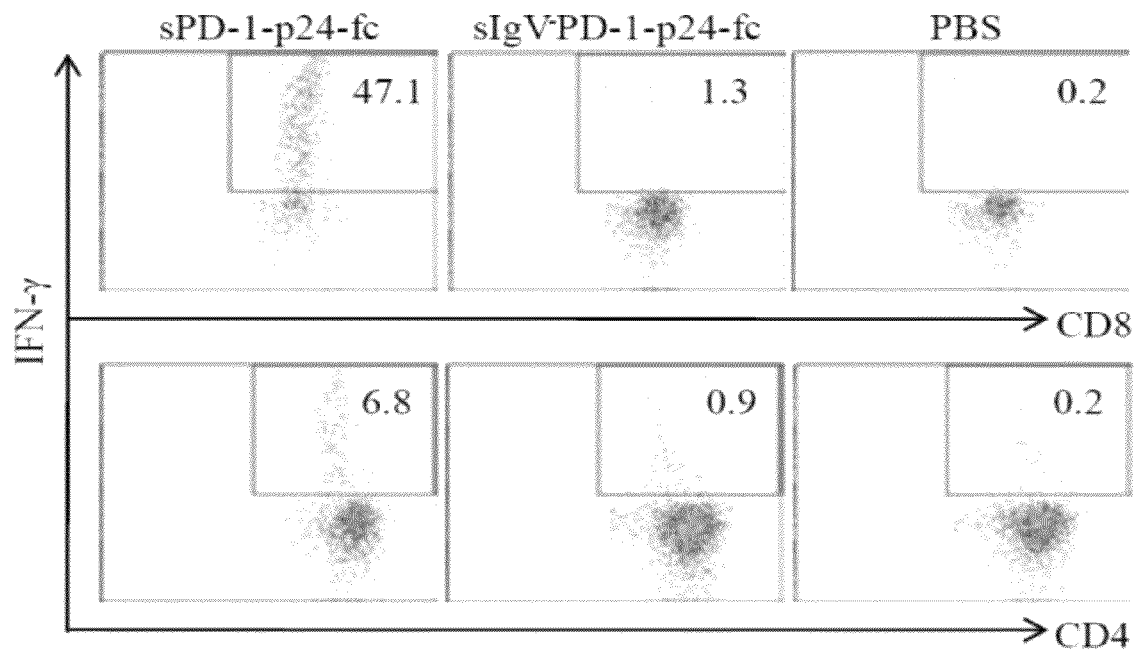
FIG. 14 shows polyfunctionality of sPD1-p24-fc induced T cells. Balb/c mice were immunized with sPD1-p24-fc and sIgV-PD1-p24-fc at a dose of 100 μg i.m./EP. Mice that received PBS alone served as control. Splenocytes were collected and analyzed by flow cytometry following intracellular staining using antibodies against IFN-γ$^+$, TNF-α, and IL-2. (A) Scatter plots indicating CD8$^+$ or CD4$^+$ T cells positive for IFN-γ⁺ and (B) TNF-α. (C) Column graphs depicting single, double or triple positive CD8⁺ or (D) CD4⁺ T cells for the cytokines IFN-γ⁺, TNF-α, and IL-2. (E) Pie chart analysis representing subpopulations of total cytokine secreting CD8⁺ or CD4⁺ T cells positive for combinations of IFN-γ, TNF-α, and IL-2. Columns represent the mean values of three replicate mice with standard error as error bars. Data are representative of two independent immunization experiments. *P<0.05, **P<0.01.
Figure 14B:
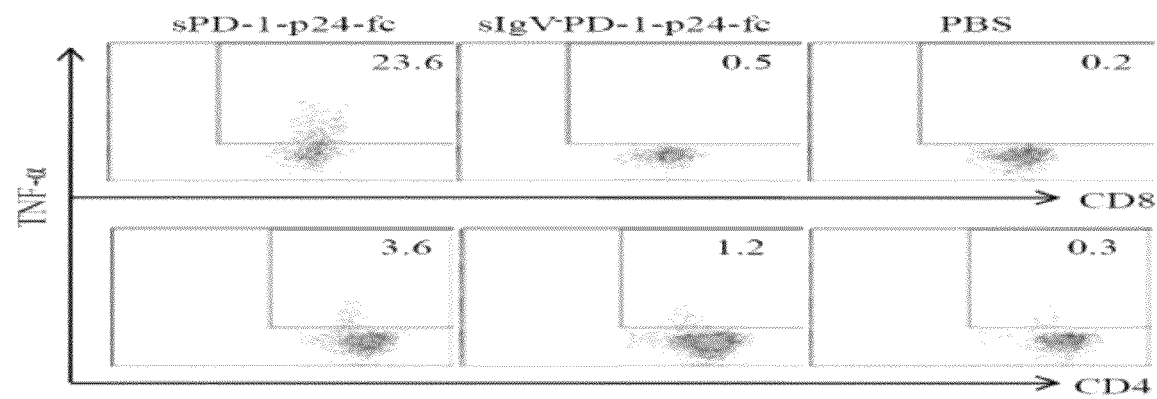
Figure 14C:
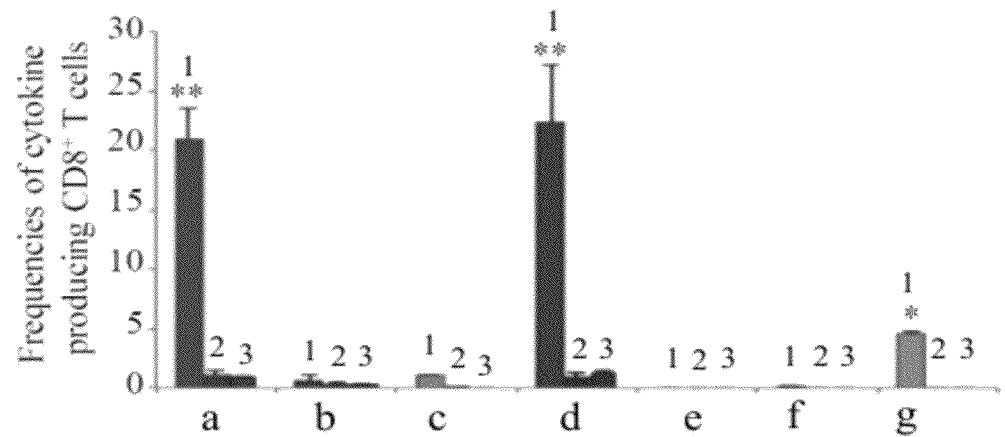
Figure 14D:
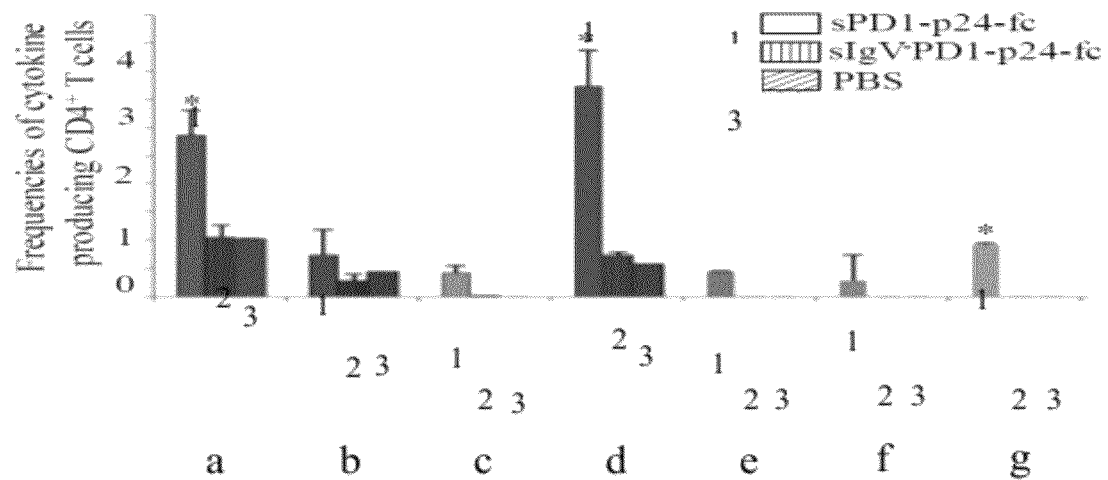
Figure 14E:
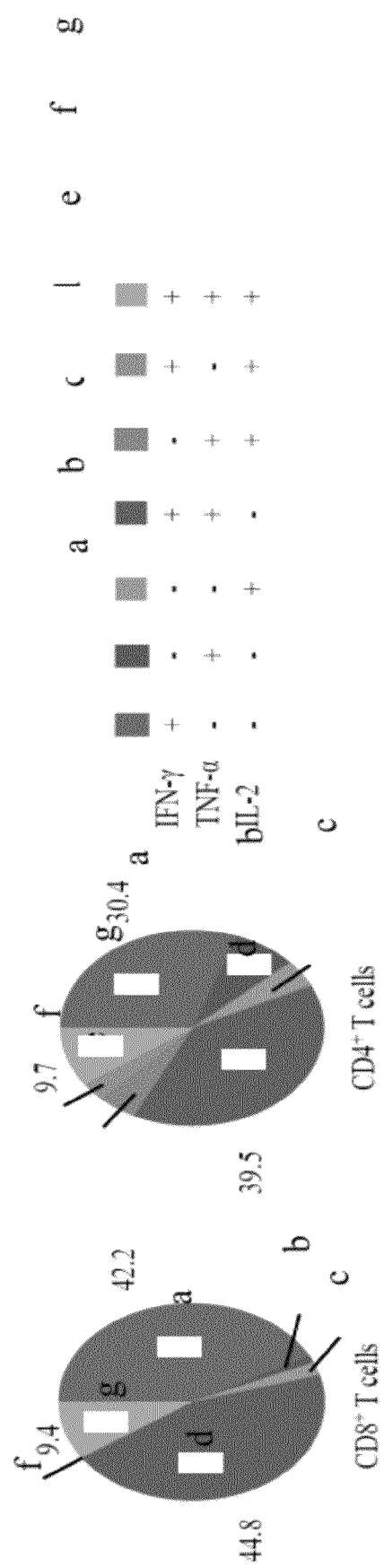

In addition, this Example investigates the ability of p24-specific T cell populations to secrete IFN-γ, TNF-α and IL-2 in response to antigen stimulation. Compared to sIgV-PD-1-p24-fc/EP, sPD-1-p24-fc/EP elicited substantially higher frequencies of p24-specific CD8+ T cells producing IFN-γ (47.1%) and TNF-α (23.6%), and elevated frequencies of p24-specific CD4+ T cells producing IFN-γ (6.8%) and TNF-α (3.6%) (FIGS. 14a and 14b). The results show that the proportion of effector-producing CD8+ and CD4+ T cell populations was similar in the order of IFN-γ+/TNF-α+>IFN-γ+>IFN-γ+/TNF-α+/IL-2+ (FIGS. 14c and 14d). Upon analyzing total cytokine-producing p24-specific CD8+ T cells, high frequency of cells secreting IFN-γ (42.2%), IFN-γ/TNF-α (44.8%) and IFN-γ/TNF-α/IL-2 (9.4%) are indicative of enhanced vaccine potency (FIG. 14e).

To characterize sPD-1-p24-fc/EP vaccination and investigate its underlying mechanism(s) of immune induction, additional experiments were performed. Specifically, this Example compared sPD-1-p24-fc DNA vaccination with or without EP at the 20 µg dose. Without EP, sPD-1-p24-fc induced 10-fold less IFN-γ+-secreting CD8+ T cells than sPD-1-p24-fc/EP (FIGS. 18a and 13d), likely due to the omission of EP's effective recruitment of DCs to the site[3]. In addition, the lack of statistical difference between sPD-1-p24-fc and sIgV-PD-1-p24-fc induced CD8+ T cells when delivered without EP (FIG. 18a) indicates that sPD-1 alone does not have a strong adjuvant effect.

In another experiment, mice were co-immunized with a mixture of 20 µg of sPD-1-fc and p24-fc by i.m./EP, and no statistical difference between these two groups in their IFN-γ+/CD8+ T cell response was found (FIG. 18b), indicating that de novo synthesis of sPD-1-fc alone was insufficient to potentiate immunogenicity. This shows the importance of DC-targeting via fusion of the antigen to sPD-1.

To exclude a role of rabbit-Fc in enhancing p24-specific immunity, the rabbit Fc fragment was removed from sPD-1-p24-fc and p24-fc to generate sPD-1-p24 and p24 DNA vaccines for immunization. In corroboration to sPD-1-p24-fc/EP, sPD-1-p24/EP induced significantly higher levels of IFN-γ+/CD8+ T cell response than p24/EP (FIG. 18c). Also, there was no statistical difference between sPD-1-p24-fc/EP and sPD-1-p24/EP in their ability to induce p24-specific IFN-γ+/CD8+ T cell responses (FIGS. 13b and 18c).

In another experiment, a human (hu-)sPD-1-p24-fc vaccine was used for comparative study, as it is known that hu-sPD-1 cross-reacts with murine PD-L1 and PD-L223 (FIG. 19a). The results show that hu-sPD-1-p24-fc/EP induced significantly greater levels of p24-specific IFN-γ+/CD8+ T cell and antibody responses, when compared to p24-fc/EP in Balb/c mice (FIGS. 19b and 19c). Anti-human PD-1 responses were also induced due to the sequence divergence from murine PD-1, which may account for the difference between murine sPD-1-p24-fc/EP and hu-sPD-1-p24-fc/EP in the observed immunogenicity profile (i.e. p24-specific CD4+ T cell response was weak in mice immunized with hu-sPD-1-p24-fc/EP) (FIG. 13e and FIG. 19c).

To determine whether sPD-1-p24-fc/EP elicited long-lived p24-specific memory T cell responses, groups of mice 7.5 months were sacrificed after the third immunization with 20 µg DNA vaccine. Besides persistent anti-p24 IgG1 and IgG2a antibody responses (FIG. 15a), p24-specific CD8+ (p<0.05)

and CD4+ (p<0.05) memory T cell responses were sustained in mice immunized with sPD-1-p24-fc/EP compared with controls (FIGS. 15b and 15c).

To investigate if cellular immunity elicited by sPD-1-p24-fc/EP leads to protection, Balb/c mice immunized with DNA vaccines at a dose of 100 μg (FIG. 13b) were challenged intranasally with $2×10^5$ PFUs of a virulent strain of vaccinia modified to express HIV-1 gag and pol (WRgagpol). Eight days post-challenge, a significant reduction in virus titers in the lungs was observed in mice vaccinated with sPD-1-p24-fc/EP compared to controls (p<0.01; FIG. 15d). Mice immunized with the placebo or sIgV-PD-1-p24-fc/EP showed >25% body weight loss within eight days after virus inoculation in contrast to mice immunized with sPD-1-p24-fc/EP that survived the challenge with <7% body weight loss (FIG. 15e). Since there were no anti-vaccinia neutralizing antibodies involved, the results indicated that p24-specific T cell immunity induced by sPD-1-p24-fc/EP provided significant protection against mucosal challenge by a virulent virus.

To summarize, this Example demonstrates that targeting of HIV-1 p24 to DCs via sPD-1 as a DNA vaccine enhanced the magnitude, breadth and polyfunctionality of specific $CD8^+$ T cell immunity. The sPD-1-based DNA vaccine can be used for inducing protective and long-lasting CD8+ T cell immunity against pathogenic infections including HIV-1, tuberculosis, and malaria.

Material and Methods

Construction of sPD-1-Based Vaccine and Controls

Three DNA vaccines, sPD-1-p24-fc, sIgV-PD-1-p24-fc, and p24-fc, were constructed in the background of pVAX1 (FIG. 13*a*). The coding sequence for the extracellular domain of murine PD-1 (sPD-1) was obtained by nested PCR from mouse cDNA 10,26, and the HIV-1 p24 fragment was amplified from a primary isolate HIV-102HNsq4 of a Chinese patient without codon-optimization[27]. To increase the flexibility of the fusion protein, a linker was applied between the sPD-1 and HIV-1 p24 gene.

A mutant form of sPD-1 (sIgV-PD-1) was also cloned following the same strategy as wild type PD-1. sIgV-PD1 does not react with PD-1 ligands[4,28] due to a two essential amino acid (position 89-90) in-frame deletion in the IgV domain. Plasmid expressing HIV-1 p24 alone served as a control.

All of the plasmids contained a rabbit Fc tag to facilitate protein purification and characterization. DNA transfection into (HEK-)293T cell was performed using Polyethylenimine (PEI), and protein expression was detected by Western blotting assay using anti-rabbit Fc antibody.

Recombinant proteins were purified from the transfected cell supernatants by affinity chromatography using Protein G Sepharose (Invitrogen), and protein concentration was measured by Micro BCA Protein Assay Kit (Thermo Scientific).

Binding Characteristics of sPD-1 Fusion Proteins $10^6$ 293T cells transiently expressing PD-L1 and PD-L2 were incubated with 2 μg of purified sPD-1-p24-fc, sIgV-PD-1-p24-fc or p24-fc fusion protein. Goat anti-rabbit IgG (H+L)-FITC (Invitrogen) was used to capture the positive cells. Transfected 293T cells stained by FITC-rat anti-mouse PD-L1 or PD-L2 antibodies (eBioscience) and FITC-rat IgG1 isotype served as positive and negative controls, respectively. Data was acquired on FACSCalibur instrument (BD Biosciences) and analyzed using BD CellQuest software.

Mouse Immunization

All animal experiments were approved by the Committee on the Use of Live Animals in Teaching and Research of the University of Hong Kong. 5-8 weeks old female Balb/c mice were bred under standard pathogen-free conditions in the Laboratory Animal Unit, University of Hong Kong. Mice were housed in cages under standard conditions with regulated temperature and humidity, fed with pelted food and tap water, and cared for according to the criteria outlined in the Guide for the Care and Use of Laboratory Animal.

The immunization procedure was similar to the previous protocols described in[15,16] (FIG. 13*b*). Mice received three DNA immunizations by intramuscular (i.m.) injection with or without EP given every three weeks at a dose of 20 μg or 100 μg per mouse. Two weeks after the final immunization, mice were sacrificed, and sera and spleen cells (splenocytes) were collected for immune response analysis.

Enzyme-Linked Immunosorbent Assay (ELISA)

Specific antibody responses were assessed by ELISA as previously described[15,16]. Briefly, high affinity, protein-binding ELISA plates (BD Bioscieces) were coated with HIV-1 p24 protein (Abcam). Serial diluted sera were then added and antibodies detected by goat-radish peroxidase (HRP)-labeled anti-mouse IgG1 or IgG2a antibody (Sigma). Relative antibody titer was expressed as the reciprocal highest dilution of samples producing at least two-fold greater optical density readout over that of the control serum sample at the same dilution.

Evaluation of HIV-1 Gag p24-Specific T Cell Responses

IFN-γ-producing T cells were evaluated by an ELISpot assay (Millipore) as previously described[15,16]. 2 μg/ml of HIV-1 p24 peptide or peptide pools (at a final concentration of 2 μg/ml for each peptide, donated by NIH) were used to stimulate splenocytes in vitro. Peptide pool consisting of 59-members of Gag p24 libraries were divided into 3 pools of 19-20 peptides that span from amino acids 1-87 (pool 1), 77-167 (pool 2) and 157-231 (pool 3). Peptide gagAI (AMQMLKDTI) (SEQ ID NO: 39) is specific for $CD8^+$ T cells, whereas peptide gag26 (TSNPPIPVGDIYKRWIILGL) (SEQ ID NO: 40) is specific for $CD4^+$ T cells[15,16].

Cells stimulated by 500 ng/ml PMA plus 1 μg/ml calcium ionocycin or left in media only served as positive and negative controls, respectively. Cells were stimulated at 37° C., 5% CO2, and 100% humidity for 20 h. Spots were identified by an immunospot reader and image analyzer (Thermo Scientific).

For intracellular cytokine staining (ICS), splenocytes were stimulated with HIV-1 p24 peptide pool (2 μg/ml for each peptide) in the presence of co-stimulatory anti-CD28 antibody (2 μg/ml, eBioscience) for 20-24 h at 37° C. 10 μg/ml Brefeldin A (BFA; Sigma) was added for the last 5 h to accumulate intracellular cytokines. Cells were washed and incubated with 2.4G2 mAb for 15 min at 4° C. to block Fcγ. After surface staining with anti-mouse CD3-APC/cy7, CD4-PE/cy5, CD8-Percp/cy5.5 antibodies (eBioscience), cells were permeabilized in 100 μl Fixation/Permeabilization solution (BD Biosciences) for 20 min at 4° C., washed with Perm/Wash™ buffer (BD), and then stained intracellularly with anti-IFN-γ-PE, anti-IL-2-PE/cy7, anti-TNF-α-FITC (eBioscience). Tetramer positive $CD8^+$ T cell population was evaluated using phycoerythrin (PE)-conjugated major histocompatibility complex (MHC) class I tetramer H2d-Kd gagAI (Beckman Coulter). Flow cytometric data were acquired and analyzed on a BD Arial III flow cytometer (BD Biosciences).

Mouse Immunization of Antigen Pulsed-Dendritic Cells

Bone marrow DCs (BM-DCs) from Balb/c mice were enriched by Dynabeads Mouse DC Enrichment Kit (Invitrogen). Two million CD11c+ BM-DCs were co-cultured with 20 μg of purified sPD-1-p24-fc or sIgV-PD-1-p24-fc proteins for 1 h at 4° C. Cells were then washed extensively with PBS and transduced into mice via tail vein injection. Untreated DCs alone served as control. Immunization procedure and immune responses analysis were the same as described above.

Vaccinia Viral Challenges

Immunized mice were challenged intranasally with 2×10⁵ PFUs vaccinia strain Western Reserve (WR) virus modified to express HIV-1 gag and pol genes. Animal body weight was monitored daily. Groups of animals were also sacrificed 8 days post challenge to measure viral titers in their lungs. Lung homogenates were prepared by physical disruption, and virus titers in the lungs were determined by a plaque-forming assay on monolayer Vero cells and monitored for cytopathic effect.

Statistical Analysis

All statistical analyses were performed using the paired one-tailed Student's t test. P values less than 0.05 were considered statistically significant. Data were presented as mean values±the standard error of at least three independent experiments.

All references, including publications, patent applications and patents, cited herein are hereby incorporated by reference to the same extent as if each reference was individually and specifically indicated to be incorporated by reference and was set forth in its entirety herein.

The terms "a" and "an" and "the" and similar referents as used in the context of describing the invention are to be construed to cover both the singular and the plural, unless otherwise indicated herein or clearly contradicted by context.

Recitation of ranges of values herein are merely intended to serve as a shorthand method of referring individually to each separate value falling within the range, unless otherwise indicated herein, and each separate value is incorporated into the specification as if it were individually recited herein. Unless otherwise stated, all exact values provided herein are representative of corresponding approximate values (e.g., all exact exemplary values provided with respect to a particular factor or measurement can be considered to also provide a corresponding approximate measurement, modified by "about," where appropriate).

The use of any and all examples, or exemplary language (e.g., "such as") provided herein, is intended merely to better illuminate the invention and does not pose a limitation on the scope of the invention unless otherwise indicated. No language in the specification should be construed as indicating any element is essential to the practice of the invention unless as much is explicitly stated.

The description herein of any aspect or embodiment of the invention using terms such as "comprising", "having", "including" or "containing" with reference to an element or elements is intended to provide support for a similar aspect or embodiment of the invention that "consists of", "consists essentially of", or "substantially comprises" that particular element or elements, unless otherwise stated or clearly contradicted by context (e.g., a composition described herein as comprising a particular element should be understood as also describing a composition consisting of that element, unless otherwise stated or clearly contradicted by context).

It should be understood that the examples and embodiments described herein are for illustrative purposes only and that various modifications or changes in light thereof will be suggested to persons skilled in the art and are to be included within the spirit and purview of this application.

REFERENCES

1. Gurunathan, S., Klinman, D. M. & Seder, R. A. DNA vaccines: immunology, application, and optimization*. *Annu Rev Immunol* 18, 927-974 (2000).
2. Yang, Z. Y. et al. A DNA vaccine induces SARS coronavirus neutralization and protective immunity in mice. *Nature* 428, 561-564 (2004).
3. Liu, J., Kjeken, R., Mathiesen, I. & Barouch, D. H. Recruitment of antigen-presenting cells to the site of inoculation and augmentation of human immunodeficiency virus type 1 DNA vaccine immunogenicity by in vivo electroporation. *J Virol* 82, 5643-5649 (2008).
4. Latchman, Y. et al. PD-L2 is a second ligand for PD-1 and inhibits T cell activation. *Nat Immunol* 2, 261-268 (2001).
5. Freeman, G. J. et al. Engagement of the PD-1 immunoinhibitory receptor by a novel B7 family member leads to negative regulation of lymphocyte activation. *J Exp Med* 192, 1027-1034 (2000).
6. Kasprowicz, V. et al. High level of PD-1 expression on hepatitis C virus (HCV)-specific CD8+ and CD4+ T cells during acute HCV infection, irrespective of clinical outcome. *J Virol* 82, 3154-3160 (2008).
7. Day, C. L. et al. PD-1 expression on HIV-specific T cells is associated with T-cell exhaustion and disease progression. *Nature* 443, 350-354 (2006).
8. Trautmann, L. et al. Programmed death 1: a critical regulator of T-cell function and a strong target for immunotherapies for chronic viral infections. *Curr Opin HIV AIDS* 2, 219-227 (2007).
9. Onlamoon, N. et al. Soluble PD-1 rescues the proliferative response of simian immunodeficiency virus-specific CD4 and CD8 T cells during chronic infection. *Immunology* 124, 277-293 (2008).
10. He, L. et al. Blockade of B7-H1 with sPD-1 improves immunity against murine hepatocarcinoma. *Anticancer Res* 25, 3309-3313 (2005).
11. Sharpe, A. H., Wherry, E. J., Ahmed, R. & Freeman, G. J. The function of programmed cell death 1 and its ligands in regulating autoimmunity and infection. *Nat Immunol* 8, 239-245 (2007).
12. Idoyaga, J. et al. Comparable T helper 1 (Th1) and CD8 T-cell immunity by targeting HIV gag p24 to CD8 dendritic cells within antibodies to Langerin, DEC205, and Clec9A. *Proc Natl Acad Sci USA* 108, 2384-2389 (2011).
13. Nchinda, G. et al. The efficacy of DNA vaccination is enhanced in mice by targeting the encoded protein to dendritic cells. *J Clin Invest* 118, 1427-1436 (2008).
14. Lazar-Molnar, E. et al. Crystal structure of the complex between programmed death-1 (PD-1) and its ligand PD-L2. *Proc Natl Acad Sci USA* 105, 10483-10488 (2008).
15. Chen, Z. et al. Design, construction, and characterization of a multigenic modified vaccinia Ankara candidate vaccine against human immunodeficiency virus type 1 subtype C/B'. *J Acquir Immune Defic Syndr* 47, 412-421 (2008).
16. Huang, Y. et al. Design, construction, and characterization of a dual-promoter multigenic DNA vaccine directed against an HIV-1 subtype C/B' recombinant. *J Acquir Immune Defic Syndr* 47, 403-411 (2008).
17. Dai, B. et al. HIV-1 Gag-specific immunity induced by a lentivector-based vaccine directed to dendritic cells. *Proc Natl Acad Sci USA* 106, 20382-20387 (2009).
18. Li, Z. et al. Novel vaccination protocol with two live mucosal vectors elicits strong cell-mediated immunity in the vagina and protects against vaginal virus challenge. *J Immunol* 180, 2504-2513 (2008).
19. Liu, L. et al. Natural mutations in the receptor binding domain of spike glycoprotein determine the reactivity of cross-neutralization between palm civet coronavirus and severe acute respiratory syndrome coronavirus. *J Virol* 81, 4694-4700 (2007).

20. Aihara, H. & Miyazaki, J. Gene transfer into muscle by electroporation in vivo. *Nat Biotechnol* 16, 867-870 (1998).
21. Liu, J. et al. Immune control of an SIV challenge by a T-cell-based vaccine in rhesus monkeys. *Nature* 457, 87-91 (2009).
22. Ferrari, G. et al. Relationship between functional profile of HIV-1 specific CD8 T cells and epitope variability with the selection of escape mutants in acute HIV-1 infection. *PLoS Pathog* 7, e1001273 (2011).
23. Lin, D. Y. et al. The PD-1/PD-L1 complex resembles the antigen-binding Fv domains of antibodies and T cell receptors. *Proc Natl Acad Sci USA* 105, 3011-3016 (2008).
24. Deliyannis, G., Boyle, J. S., Brady, J. L., Brown, L. E. & Lew, A. M. A fusion DNA vaccine that targets antigen-presenting cells increases protection from viral challenge. *Proc Natl Acad Sci USA* 97, 6676-6680 (2000).
25. Zhang, W., Chen, Z., Huang, Y., Song, Y. & Ho, D. D. CTLA4-mediated APC-targeting enhanced the humoral and cellular immune responses of an SIV DNA vaccine in mice. in 10*th Conf Retrovir Oppor Infect* (2003).
26. Kuipers, H. et al. Contribution of the PD-1 ligands/PD-1 signaling pathway to dendritic cell-mediated CD4+ T cell activation. *Eur J Immunol* 36, 2472-2482 (2006).
27. Su, B. et al. HIV-1 subtype B' dictates the AIDS epidemic among paid blood donors in the Henan and Hubei provinces of China. *AIDS* 17, 2515-2520 (2003).
28. Wang, S. et al. Molecular modeling and functional mapping of B7-H1 and B7-DC uncouple costimulatory function from PD-1 interaction. *J Exp Med* 197, 1083-1091 (2003).

We claim:

1. A PD-1 DNA molecule encoding a soluble PD-1 protein comprising an amino acid sequence selected from the group consisting of SEQ ID NO: 11, SEQ ID NO: 15, and SEQ ID NO: 25.

2. A sPD-1 fusion nucleic acid molecule encoding a PD-1 fusion protein, the fusion protein comprising a soluble PD-1 protein fragment and an antigenic protein fragment, wherein the soluble PD-1 protein fragment comprises an amino acid sequence selected from the group consisting of SEQ ID NO: 1, SEQ ID NO: 21, SEQ ID NO: 11, SEQ ID NO: 15, and SEQ ID NO: 25.

3. The sPD-1 fusion nucleic acid molecule of claim 2, wherein the nucleic acid molecule comprises a sequence of SEQ ID NO: 24.

4. A vaccine composition comprising the sPD-1 fusion nucleic acid molecule of claim 2.

* * * * *

UNITED STATES PATENT AND TRADEMARK OFFICE
CERTIFICATE OF CORRECTION

PATENT NO. : 9,029,315 B2  
APPLICATION NO. : 13/294306  
DATED : May 12, 2015  
INVENTOR(S) : Zhiwei Chen and Jingying Zhou Page 1 of 1

It is certified that error appears in the above-identified patent and that said Letters Patent is hereby corrected as shown below:

In the specification

Column 2,  
Line 56, "+standard deviations" should read --±standard deviations--.

Column 9,  
Line 58, "mspd" should read --mspd1--.

Column 10,  
Line 14, "Epstein-Barr virus, anpapillomavirus," should read --Epstein-Barr virus, meningococcus, anpapillomavirus,--.

Column 12,  
Line 43, "☐-amino" should read --ε-amino--.

Column 22,  
Line 49, "20μm" should read --20μg--.

Column 23,  
Line 54, "CD8" should read --CD8$^+$--.

Column 24,  
Line 4, "FIGS. 3g" should read --Figure 13g--.

Column 26,  
Line 45, "20-24" should read --20~24--.

Signed and Sealed this  
Third Day of May, 2016

Michelle K. Lee  
*Director of the United States Patent and Trademark Office*

SEQUENCE LISTING

```
<160> NUMBER OF SEQ ID NOS: 40

<210> SEQ ID NO 1
<211> LENGTH: 178
<212> TYPE: PRT
<213> ORGANISM: mouse
<220> FEATURE:
<223> OTHER INFORMATION: wild-type mouse spd1

<400> SEQUENCE: 1

Met Trp Val Arg Gln Val Pro Trp Ser Phe Thr Trp Ala Val Leu Gln
1               5                   10                  15

Leu Ser Trp Gln Ser Gly Trp Leu Leu Glu Val Pro Asn Gly Pro Trp
            20                  25                  30

Arg Ser Leu Thr Phe Tyr Pro Ala Trp Leu Thr Val Ser Glu Gly Ala
        35                  40                  45

Asn Ala Thr Phe Thr Cys Ser Leu Ser Asn Trp Ser Glu Asp Leu Met
    50                  55                  60

Leu Asn Trp Asn Arg Leu Ser Pro Ser Asn Gln Thr Glu Lys Gln Ala
65                  70                  75                  80

Ala Phe Cys Asn Gly Leu Ser Gln Pro Val Gln Asp Ala Arg Phe Gln
                85                  90                  95

Ile Ile Gln Leu Pro Asn Arg His Asp Phe His Met Asn Ile Leu Asp
            100                 105                 110

Thr Arg Arg Asn Asp Ser Gly Ile Tyr Leu Cys Gly Ala Ile Ser Leu
        115                 120                 125

His Pro Lys Ala Lys Ile Glu Glu Ser Pro Gly Ala Glu Leu Val Val
    130                 135                 140

Thr Glu Arg Ile Leu Glu Thr Ser Thr Arg Tyr Pro Ser Pro Ser Pro
145                 150                 155                 160

Lys Pro Glu Gly Arg Phe Gln Pro Glu Phe Arg Gly Gly Gly Ser Gly
                165                 170                 175

Gly Gly

<210> SEQ ID NO 2
<211> LENGTH: 537
<212> TYPE: DNA
<213> ORGANISM: mouse
<220> FEATURE:
<223> OTHER INFORMATION: wild-type mouse spd1

<400> SEQUENCE: 2
atgtgggtcc ggcaggtacc ctggtcattc acttgggctg tgctgcagtt gagctggcaa       60
```

```
tcagggtggc ttctagaggt ccccaatggg ccctggaggt ccctcacctt ctacccagcc    120
tggctcacag tgtcagaggg agcaaatgcc accttcacct gcagcttgtc caactggtcg    180
gaggatctta tgctgaactg gaaccgcctg agtcccagca accagactga aaaacaggcc    240
gccttctgta atggtttgag ccaacccgtc caggatgccc gcttccagat catacagctg    300
cccaacaggc atgacttcca catgaacatc cttgacacac ggcgcaatga cagtggcatc    360
tacctctgtg gggccatctc cctgcacccc aaggcaaaaa tcgaggagag ccctggagca    420
gagctcgtgg taacagagag aatcctggag acctcaacaa gatatcccag ccctcgccc     480 aaaccagaag gccggtttca accggaattc cggggtggtg gtggttcagg aggagga       537
```

<210> SEQ ID NO 3
<211> LENGTH: 231
<212> TYPE: PRT
<213> ORGANISM: HIV
<220> FEATURE:
<223> OTHER INFORMATION: HIV p24

<400> SEQUENCE: 3

```
Pro Ile Val Gln Asn Leu Gln Gly Gln Met Val His Gln Pro Ile Ser
1               5                   10                  15

Pro Arg Thr Leu Asn Ala Trp Val Lys Val Ile Glu Glu Lys Ala Phe
            20                  25                  30

Ser Pro Glu Val Ile Pro Met Phe Ser Ala Leu Ser Glu Gly Ala Thr
        35                  40                  45

Pro Gln Asp Leu Asn Thr Met Leu Asn Thr Val Gly Gly His Gln Ala
    50                  55                  60

Ala Met Gln Met Leu Lys Glu Thr Ile Asn Glu Glu Ala Ala Glu Trp
65                  70                  75                  80

Asp Arg Leu His Pro Val Gln Ala Gly Pro Val Ala Pro Gly Gln Met
                85                  90                  95

Arg Glu Pro Arg Gly Ser Asp Ile Ala Gly Thr Thr Ser Asn Leu Gln
            100                 105                 110

Glu Gln Ile Gly Trp Met Thr Asn Asn Pro Pro Ile Pro Val Gly Glu
        115                 120                 125

Ile Tyr Lys Arg Trp Ile Ile Leu Gly Leu Asn Lys Ile Val Arg Met
    130                 135                 140

Tyr Ser Pro Thr Ser Ile Leu Asp Ile Arg Gln Gly Pro Lys Glu Pro
145                 150                 155                 160

Phe Arg Asp Tyr Val Asp Arg Phe Tyr Lys Thr Leu Arg Ala Glu Gln
                165                 170                 175

Ala Ser Gln Glu Val Lys Asn Trp Met Thr Glu Thr Leu Leu Val Gln
            180                 185                 190

Asn Ser Asn Pro Asp Cys Lys Thr Ile Leu Lys Ala Leu Gly Pro Ala
        195                 200                 205

Ala Thr Leu Glu Glu Met Met Thr Ala Cys Gln Gly Val Gly Gly Pro
    210                 215                 220

Gly His Lys Ala Arg Val Leu
225                 230
```

<210> SEQ ID NO 4
<211> LENGTH: 693
<212> TYPE: DNA
<213> ORGANISM: HIV
<220> FEATURE:
<223> OTHER INFORMATION: HIV p24

<400> SEQUENCE: 4

```
cctatagtgc aaaacctcca ggggcaaatg gtacatcagc ccatatcacc tagaacttta      60
aatgcatggg taaaagtaat agaagagaag gcttttagtc cagaagtaat acccatgttt     120
tcagcattat cagaaggagc cacccccacaa gatttaaaca ccatgctaaa cacagtgggg    180
ggacatcaag cagccatgca aatgttaaaa gaaaccatca atgaggaagc tgcagaatgg    240
gatagattgc atccagtgca ggcagggcca gttgcaccag ccagatgag agaaccaagg     300
ggaagtgaca tagcaggaac tactagtaat cttcaggagc aaataggatg gatgacaaat    360
aatccaccta tcccagtagg agaaatctat aaaagatgga taatcctggg gttaaataaa    420
atagtaagaa tgtatagccc taccagcatt ctggacataa gacaaggacc aaaggaaccc    480
tttagagact atgtagaccg gttctataaa actctaagag ccgagcaagc ttcacaagag    540
gtaaaaaatt ggatgacaga aaccttgttg gtccaaaatt cgaacccaga ttgtaagact    600
atttttaaaag cattgggacc agcagctaca ctagaagaaa tgatgacagc atgtcaggga    660
gtgggggggac ctggccataa agcaagagtt ttg                                 693
```

<210> SEQ ID NO 5
<211> LENGTH: 288
<212> TYPE: PRT
<213> ORGANISM: rabbit
<220> FEATURE:
<223> OTHER INFORMATION: rabbit Fc domain

<400> SEQUENCE: 5

```
Met Gln Tyr Ile Lys Ala Asn Ser Lys Phe Ile Gly Ile Thr Glu Leu
1               5                   10                  15

Lys Lys Leu Gly Gly Ser Asn Asp Ile Phe Asn Asn Phe Thr Val Ser
            20                  25                  30

Phe Trp Leu Arg Val Pro Lys Val Ser Ala Ser His Leu Glu Gln Tyr
        35                  40                  45

Leu Glu Ala Thr Asn Thr Lys Val Asp Lys Thr Val Ala Pro Ser Thr
    50                  55                  60

Cys Ser Lys Pro Met Cys Pro Pro Pro Glu Leu Leu Gly Gly Pro Ser
65                  70                  75                  80

Val Phe Ile Phe Pro Pro Lys Pro Lys Asp Thr Leu Met Ile Ser Arg
                85                  90                  95

Thr Pro Glu Val Thr Cys Val Val Val Asp Val Ser Gln Asp Asp Pro
            100                 105                 110

Glu Val Gln Phe Thr Trp Tyr Ile Asn Asn Glu Gln Val Arg Thr Ala
        115                 120                 125

Arg Pro Pro Leu Arg Glu Gln Gln Phe Asn Ser Thr Ile Arg Val Val
    130                 135                 140

Ser Thr Leu Pro Ile Ala His Gln Asp Trp Leu Arg Gly Lys Glu Phe
145                 150                 155                 160

Lys Cys Lys Val His Asn Lys Ala Leu Pro Ala Pro Ile Glu Lys Thr
                165                 170                 175

Ile Ser Lys Ala Arg Gly Gln Pro Leu Glu Pro Lys Val Tyr Thr Met
            180                 185                 190

Gly Pro Pro Arg Glu Glu Leu Ser Ser Arg Ser Val Ser Leu Thr Cys
        195                 200                 205

Met Ile Asn Gly Phe Tyr Pro Ser Asp Ile Ser Val Glu Trp Glu Lys
    210                 215                 220
```

```
Asn Gly Lys Ala Glu Asp Asn Tyr Lys Thr Thr Pro Thr Val Leu Asp
225                 230                 235                 240

Ser Asp Gly Ser Tyr Phe Leu Tyr Ser Lys Leu Ser Val Pro Thr Ser
            245                 250                 255

Glu Trp Gln Arg Gly Asp Val Phe Thr Cys Ser Val Met His Glu Ala
        260                 265                 270

Leu His Asn His Tyr Thr Gln Lys Ser Ile Ser His Ser Pro Gly Lys
    275                 280                 285
```

<210> SEQ ID NO 6
<211> LENGTH: 880
<212> TYPE: DNA
<213> ORGANISM: rabbit
<220> FEATURE:
<223> OTHER INFORMATION: rabbit Fc domain

<400> SEQUENCE: 6

```
atcctgatgc agtacatcaa ggccaacagt aagttcatcg gaatcaccga gcttaagaag    60
ctgggaggct caaacgacat attcaacaac ttcacagtgt ccttctggtt gcgggttccc   120
aaggtctctg ctagccacct cgaacaatac ctggaggcca ccaacaccaa agtggacaag   180
accgttgcgc cctcgacatg cagcaagccc atgtgcccac cccctgaact cctgggggga   240
ccgtctgtct tcatcttccc cccaaaaccc aaggacaccc tcatgatctc acgcaccccc   300
gaggtcacat gcgtggtggt ggacgtgagc caggatgacc ccgaggtgca gttcacatgg   360
tacataaaca acgagcaggt gcgcaccgcc cggccgccgc tacgggagca gcagttcaac   420
agcacgatcc gcgtggtcag caccctcccc atcgcgcacc aggactggct gaggggcaag   480
gagttcaagt gcaaagtcca acaaggca ctcccggccc ccatcgagaa aaccatctcc   540
aaagccagag gcagcccct ggagccgaag gtctacacca tgggccctcc ccggggaggag   600
ctgagcagca ggtcggtcag cctgacctgc atgatcaacg gcttctaccc ttccgacatc   660
tcggtggagt gggagaagaa cgggaaggca gaggacaact acaagaccac gccgaccgtg   720
ctggacagcg acggctccta cttcctctac agcaagctct cagtgcccac gagtgagtgg   780
cagcggggcg acgtcttcac ctgctccgtg atgcacgagg ccttgcacaa ccactacacg   840
cagaagtcca tctcccactc tcctggtaaa taatctagag                         880
```

<210> SEQ ID NO 7
<211> LENGTH: 176
<212> TYPE: PRT
<213> ORGANISM: Artificial Sequence
<220> FEATURE:
<223> OTHER INFORMATION: mspd1-IgV

<400> SEQUENCE: 7

```
Met Trp Val Arg Gln Val Pro Trp Ser Phe Thr Trp Ala Val Leu Gln
1               5                   10                  15

Leu Ser Trp Gln Ser Gly Trp Leu Leu Glu Val Pro Asn Gly Pro Trp
            20                  25                  30

Arg Ser Leu Thr Phe Tyr Pro Ala Trp Leu Thr Val Ser Glu Gly Ala
        35                  40                  45

Asn Ala Thr Phe Thr Cys Ser Leu Ser Asn Trp Ser Glu Asp Leu Met
    50                  55                  60

Leu Asn Trp Asn Arg Leu Ser Pro Ser Asn Gln Thr Glu Lys Gln Ala
65                  70                  75                  80

Ala Phe Cys Asn Gly Leu Ser Gln Gln Asp Ala Arg Phe Gln Ile Ile
            85                  90                  95
```

```
Gln Leu Pro Asn Arg His Asp Phe His Met Asn Ile Leu Asp Thr Arg
                100                 105                 110

Arg Asn Asp Ser Gly Ile Tyr Leu Cys Gly Ala Ile Ser Leu His Pro
            115                 120                 125

Lys Ala Lys Ile Glu Glu Ser Pro Gly Ala Glu Leu Val Val Thr Glu
        130                 135                 140

Arg Ile Leu Glu Thr Ser Thr Arg Tyr Pro Ser Pro Ser Pro Lys Pro
145                 150                 155                 160

Glu Gly Arg Phe Gln Pro Glu Phe Arg Gly Gly Ser Gly Gly Gly
                165                 170                 175

<210> SEQ ID NO 8
<211> LENGTH: 531
<212> TYPE: DNA
<213> ORGANISM: Artificial Sequence
<220> FEATURE:
<223> OTHER INFORMATION: mspd1-IgV

<400> SEQUENCE: 8
atgtgggtcc ggcaggtacc ctggtcattc acttgggctg tgctgcagtt gagctggcaa      60
tcagggtggc ttctagaggt ccccaatggg ccctggaggt ccctcacctt ctacccagcc     120
tggctcacag tgtcagaggg agcaaatgcc accttcacct gcagcttgtc caactggtcg     180
gaggatctta tgctgaactg gaaccgcctg agtcccagca accagactga aaaacaggcc     240
gccttctgta atggtttgag ccaacaggat gcccgcttcc agatcataca gctgcccaac     300
aggcatgact ccacatgaa catccttgac acacggcgca atgacagtgg catctacctc     360 tgtgggcca tctccctgca ccccaaggca aaatcgagg agagccctgg agcagagctc     420
gtggtaacag agagaatcct ggagacctca acaagatatc ccagcccctc gcccaaacca     480
gaaggccggt tcaaccgga attccggggt ggtggtggtt caggaggagg a              531

<210> SEQ ID NO 9
<211> LENGTH: 695
<212> TYPE: PRT
<213> ORGANISM: Artificial Sequence
<220> FEATURE:
<223> OTHER INFORMATION: mspd1-IgV-p24-Fc fusion protein

<400> SEQUENCE: 9

Met Trp Val Arg Gln Val Pro Trp Ser Phe Thr Trp Ala Val Leu Gln
1               5                   10                  15

Leu Ser Trp Gln Ser Gly Trp Leu Leu Glu Val Pro Asn Gly Pro Trp
            20                  25                  30

Arg Ser Leu Thr Phe Tyr Pro Ala Trp Leu Thr Val Ser Glu Gly Ala
        35                  40                  45

Asn Ala Thr Phe Thr Cys Ser Leu Ser Asn Trp Ser Glu Asp Leu Met
    50                  55                  60

Leu Asn Trp Asn Arg Leu Ser Pro Ser Asn Gln Thr Glu Lys Gln Ala
65                  70                  75                  80

Ala Phe Cys Asn Gly Leu Ser Gln Gln Asp Ala Arg Phe Gln Ile Ile
                85                  90                  95

Gln Leu Pro Asn Arg His Asp Phe His Met Asn Ile Leu Asp Thr Arg
                100                 105                 110

Arg Asn Asp Ser Gly Ile Tyr Leu Cys Gly Ala Ile Ser Leu His Pro
            115                 120                 125

Lys Ala Lys Ile Glu Glu Ser Pro Gly Ala Glu Leu Val Val Thr Glu
```

```
            130                 135                 140
Arg Ile Leu Glu Thr Ser Thr Arg Tyr Pro Ser Pro Ser Pro Lys Pro
145                 150                 155                 160

Glu Gly Arg Phe Gln Pro Glu Phe Arg Gly Gly Ser Gly Gly Gly
                165                 170                 175

Pro Ile Val Gln Asn Leu Gln Gly Gln Met Val His Gln Pro Ile Ser
                180                 185                 190

Pro Arg Thr Leu Asn Ala Trp Val Lys Val Ile Glu Glu Lys Ala Phe
                195                 200                 205

Ser Pro Glu Val Ile Pro Met Phe Ser Ala Leu Ser Glu Gly Ala Thr
            210                 215                 220

Pro Gln Asp Leu Asn Thr Met Leu Asn Thr Val Gly Gly His Gln Ala
225                 230                 235                 240

Ala Met Gln Met Leu Lys Glu Thr Ile Asn Glu Glu Ala Ala Glu Trp
                245                 250                 255

Asp Arg Leu His Pro Val Gln Ala Gly Pro Val Ala Pro Gly Gln Met
                260                 265                 270

Arg Glu Pro Arg Gly Ser Asp Ile Ala Gly Thr Thr Ser Asn Leu Gln
            275                 280                 285

Glu Gln Ile Gly Trp Met Thr Asn Asn Pro Pro Ile Pro Val Gly Glu
290                 295                 300

Ile Tyr Lys Arg Trp Ile Ile Leu Gly Leu Asn Lys Ile Val Arg Met
305                 310                 315                 320

Tyr Ser Pro Thr Ser Ile Leu Asp Ile Arg Gln Gly Pro Lys Glu Pro
                325                 330                 335

Phe Arg Asp Tyr Val Asp Arg Phe Tyr Lys Thr Leu Arg Ala Glu Gln
                340                 345                 350

Ala Ser Gln Glu Val Lys Asn Trp Met Thr Glu Thr Leu Leu Val Gln
            355                 360                 365

Asn Ser Asn Pro Asp Cys Lys Thr Ile Leu Lys Ala Leu Gly Pro Ala
370                 375                 380

Ala Thr Leu Glu Glu Met Met Thr Ala Cys Gln Gly Val Gly Gly Pro
385                 390                 395                 400

Gly His Lys Ala Arg Val Leu Met Gln Tyr Ile Lys Ala Asn Ser Lys
                405                 410                 415

Phe Ile Gly Ile Thr Glu Leu Lys Lys Leu Gly Gly Ser Asn Asp Ile
                420                 425                 430

Phe Asn Asn Phe Thr Val Ser Phe Trp Leu Arg Val Pro Lys Val Ser
            435                 440                 445

Ala Ser His Leu Glu Gln Tyr Leu Glu Ala Thr Asn Thr Lys Val Asp
            450                 455                 460

Lys Thr Val Ala Pro Ser Thr Cys Ser Lys Pro Met Cys Pro Pro Pro
465                 470                 475                 480

Glu Leu Leu Gly Gly Pro Ser Val Phe Ile Phe Pro Lys Pro Lys
                485                 490                 495

Asp Thr Leu Met Ile Ser Arg Thr Pro Glu Val Thr Cys Val Val Val
                500                 505                 510

Asp Val Ser Gln Asp Asp Pro Glu Val Gln Phe Thr Trp Tyr Ile Asn
            515                 520                 525

Asn Glu Gln Val Arg Thr Ala Arg Pro Pro Leu Arg Glu Gln Gln Phe
            530                 535                 540

Asn Ser Thr Ile Arg Val Val Ser Thr Leu Pro Ile Ala His Gln Asp
545                 550                 555                 560
```

```
Trp Leu Arg Gly Lys Glu Phe Lys Cys Lys Val His Asn Lys Ala Leu
            565                 570                 575
Pro Ala Pro Ile Glu Lys Thr Ile Ser Lys Ala Arg Gly Gln Pro Leu
        580                 585                 590
Glu Pro Lys Val Tyr Thr Met Gly Pro Pro Arg Glu Glu Leu Ser Ser
    595                 600                 605
Arg Ser Val Ser Leu Thr Cys Met Ile Asn Gly Phe Tyr Pro Ser Asp
610                 615                 620
Ile Ser Val Glu Trp Glu Lys Asn Gly Lys Ala Glu Asp Asn Tyr Lys
625                 630                 635                 640
Thr Thr Pro Thr Val Leu Asp Ser Asp Gly Ser Tyr Phe Leu Tyr Ser
                645                 650                 655
Lys Leu Ser Val Pro Thr Ser Glu Trp Gln Arg Gly Asp Val Phe Thr
            660                 665                 670
Cys Ser Val Met His Glu Ala Leu His Asn His Tyr Thr Gln Lys Ser
        675                 680                 685
Ile Ser His Ser Pro Gly Lys
    690                 695

<210> SEQ ID NO 10
<211> LENGTH: 2104
<212> TYPE: DNA
<213> ORGANISM: Artificial Sequence
<220> FEATURE:
<223> OTHER INFORMATION: mspd1-IgV-p24-Fc

<400> SEQUENCE: 10
atgtgggtcc ggcaggtacc ctggtcattc acttgggctg tgctgcagtt gagctggcaa       60
tcagggtggc ttctagaggt ccccaatggg ccctggaggt ccctcacctt ctacccagcc      120
tggctcacag tgtcagaggg agcaaatgcc accttcacct gcagcttgtc caactggtcg      180
gaggatctta tgctgaactg gaaccgcctg agtcccagca accagactga aaaacaggcc      240
gccttctgta atggtttgag ccaacaggat gcccgcttcc agatcataca gctgcccaac      300
aggcatgact ccacatgaa catccttgac acacggcgca atgacagtgg catctacctc      360 tgtgggcca tctccctgca ccccaaggca aaatcgagg agagccctgg agcagagctc      420
gtggtaacag agagaatcct ggagacctca acaagatatc ccagccctc gcccaaacca      480 gaaggccggt ttcaaccgga attccggggt ggtggtggtt caggaggagg acctatagtg      540
caaaacctcc aggggcaaat ggtacatcag cccatatcac ctagaacttt aaatgcatgg      600
gtaaaagtaa tagaagagaa ggcttttagt ccagaagtaa tacccatgtt ttcagcatta      660
tcagaaggag ccaccccaca agatttaaac accatgctaa acacagtggg gggacatcaa      720
gcagccatgc aaatgttaaa agaaaccatc aatgaggaag ctgcagaatg ggatagattg      780
catccagtgc aggcagggcc agttgcacca ggccagatga gaaccaag gggaagtgac      840 atagcaggaa ctactagtaa tcttcaggag caaataggat ggatgacaaa taatccacct      900
atcccagtag gagaaatcta taaagatgg ataatcctgg ggttaaataa aatagtaaga      960
atgtatagcc ctaccagcat tctggacata agacaaggac caaaggaacc ctttagagac     1020
tatgtagacc ggttctataa aactctaaga gccgagcaag cttcacaaga ggtaaaaaat     1080
tggatgacag aaaccttgtt ggtccaaaat tcgaacccag attgtaagac tattttaaaa     1140
gcattgggac cagcagctac actagaagaa atgatgacag catgtcaggg agtgggggga     1200
cctggccata agcaagagt tttgatcctg atgcagtaca tcaaggccaa cagtaagttc     1260
```

-continued

```
atcggaatca ccgagcttaa gaagctggga ggctcaaacg acatattcaa caacttcaca      1320
gtgtccttct ggttgcgggt tcccaaggtc tctgctagcc acctcgaaca ataccctggag     1380
gccaccaaca ccaaagtgga caagaccgtt gcgccctcga catgcagcaa gcccatgtgc      1440
ccacccctg aactcctggg gggaccgtct gtcttcatct ccccccaaa acccaaggac       1500
accctcatga tctcacgcac ccccgaggtc acatgcgtgg tggtggacgt gagccaggat      1560
gaccccgagg tgcagttcac atggtacata aacaacgagc aggtgcgcac cgcccggccg      1620
ccgctacggg agcagcagtt caacagcacg atccgcgtgg tcagcaccct cccatcgcg      1680
caccaggact ggctgagggg caaggagttc aagtgcaaag tccacaacaa ggcactcccg      1740
gcccccatcg agaaaaccat ctccaaagcc agagggcagc cctggagcc gaaggtctac      1800
accatgggcc ctccccggga ggagctgagc agcaggtcgg tcagcctgac ctgcatgatc      1860
aacggcttct acccttccga catctcggtg gagtgggaga gaacgggaa ggcagaggac      1920
aactacaaga ccacgccgac cgtgctggac agcgacggct cctacttcct ctacagcaag      1980
ctctcagtgc ccacgagtga gtggcagcgg ggcgacgtct tcacctgctc cgtgatgcac      2040
gaggccttgc acaaccacta cacgcagaag tccatctccc actctcctgg taaataatct      2100
agag                                                                   2104
```

<210> SEQ ID NO 11
<211> LENGTH: 164
<212> TYPE: PRT
<213> ORGANISM: Artificial Sequence
<220> FEATURE:
<223> OTHER INFORMATION: mspd1-14del

<400> SEQUENCE: 11

```
Met Trp Val Arg Gln Val Pro Trp Ser Phe Thr Trp Ala Val Leu Gln
  1               5                  10                  15

Leu Ser Trp Gln Ser Gly Trp Leu Leu Ala Trp Leu Thr Val Ser Glu
             20                  25                  30

Gly Ala Asn Ala Thr Phe Thr Cys Ser Leu Ser Asn Trp Ser Glu Asp
         35                  40                  45

Leu Met Leu Asn Trp Asn Arg Leu Ser Pro Ser Asn Gln Thr Glu Lys
     50                  55                  60

Gln Ala Ala Phe Cys Asn Gly Leu Ser Gln Pro Val Gln Asp Ala Arg
 65                  70                  75                  80

Phe Gln Ile Ile Gln Leu Pro Asn Arg His Asp Phe His Met Asn Ile
                 85                  90                  95

Leu Asp Thr Arg Arg Asn Asp Ser Gly Ile Tyr Leu Cys Gly Ala Ile
            100                 105                 110

Ser Leu His Pro Lys Ala Lys Ile Glu Glu Ser Pro Gly Ala Glu Leu
        115                 120                 125

Val Val Thr Glu Arg Ile Leu Glu Thr Ser Thr Arg Tyr Pro Ser Pro
    130                 135                 140

Ser Pro Lys Pro Glu Gly Arg Phe Gln Pro Glu Phe Arg Gly Gly Gly
145                 150                 155                 160

Ser Gly Gly Gly
```

<210> SEQ ID NO 12
<211> LENGTH: 495
<212> TYPE: DNA
<213> ORGANISM: Artificial Sequence
<220> FEATURE:

<223> OTHER INFORMATION: mspd1-14del

<400> SEQUENCE: 12

```
atgtgggtcc ggcaggtacc ctggtcattc acttgggctg tgctgcagtt gagctggcaa    60
tcagggtggc ttctagcctg gctcacagtg tcagagggag caaatgccac cttcacctgc   120
agcttgtcca actggtcgga ggatcttatg ctgaactgga accgcctgag tccagcaac    180
cagactgaaa aacaggccgc cttctgtaat ggtttgagcc aacccgtcca ggatgcccgc   240
ttccagatca tacagctgcc aacaggcat gacttccaca tgaacatcct tgacacacgg   300
cgcaatgaca gtggcatcta cctctgtggg gccatctccc tgcacccaa ggcaaaaatc   360
gaggagagcc ctggagcaga gctcgtggta acagagagaa tcctggagac ctcaacaaga   420
tatcccagcc cctcgcccaa accagaaggc cggtttcaac cggaattccg ggtggtggt    480
ggttcaggag gagga                                                    495
```

<210> SEQ ID NO 13
<211> LENGTH: 683
<212> TYPE: PRT
<213> ORGANISM: Artificial Sequence
<220> FEATURE:
<223> OTHER INFORMATION: mspd1-14del-p24-Fc

<400> SEQUENCE: 13

```
Met Trp Val Arg Gln Val Pro Trp Ser Phe Thr Trp Ala Val Leu Gln
  1               5                  10                  15

Leu Ser Trp Gln Ser Gly Trp Leu Leu Ala Trp Leu Thr Val Ser Glu
             20                  25                  30

Gly Ala Asn Ala Thr Phe Thr Cys Ser Leu Ser Asn Trp Ser Glu Asp
         35                  40                  45

Leu Met Leu Asn Trp Asn Arg Leu Ser Pro Ser Asn Gln Thr Glu Lys
     50                  55                  60

Gln Ala Ala Phe Cys Asn Gly Leu Ser Gln Pro Val Gln Asp Ala Arg
 65                  70                  75                  80

Phe Gln Ile Ile Gln Leu Pro Asn Arg His Asp Phe His Met Asn Ile
                 85                  90                  95

Leu Asp Thr Arg Arg Asn Asp Ser Gly Ile Tyr Leu Cys Gly Ala Ile
            100                 105                 110

Ser Leu His Pro Lys Ala Lys Ile Glu Glu Ser Pro Gly Ala Glu Leu
        115                 120                 125

Val Val Thr Glu Arg Ile Leu Glu Thr Ser Thr Arg Tyr Pro Ser Pro
    130                 135                 140

Ser Pro Lys Pro Glu Gly Arg Phe Gln Pro Glu Phe Arg Gly Gly Gly
145                 150                 155                 160

Ser Gly Gly Gly Pro Ile Val Gln Asn Leu Gln Gly Gln Met Val His
                165                 170                 175

Gln Pro Ile Ser Pro Arg Thr Leu Asn Ala Trp Val Lys Val Ile Glu
            180                 185                 190

Glu Lys Ala Phe Ser Pro Glu Val Ile Pro Met Phe Ser Ala Leu Ser
        195                 200                 205

Glu Gly Ala Thr Pro Gln Asp Leu Asn Thr Met Leu Asn Thr Val Gly
    210                 215                 220

Gly His Gln Ala Ala Met Gln Met Leu Lys Glu Thr Ile Asn Glu Glu
225                 230                 235                 240

Ala Ala Glu Trp Asp Arg Leu His Pro Val Gln Ala Gly Pro Val Ala
                245                 250                 255
```

-continued

```
Pro Gly Gln Met Arg Glu Pro Arg Gly Ser Asp Ile Ala Gly Thr Thr
            260                 265                 270

Ser Asn Leu Gln Glu Gln Ile Gly Trp Met Thr Asn Pro Pro Ile
        275                 280                 285

Pro Val Gly Glu Ile Tyr Lys Arg Trp Ile Ile Leu Gly Leu Asn Lys
    290                 295                 300

Ile Val Arg Met Tyr Ser Pro Thr Ser Ile Leu Asp Ile Arg Gln Gly
305                 310                 315                 320

Pro Lys Glu Pro Phe Arg Asp Tyr Val Asp Arg Phe Tyr Lys Thr Leu
                325                 330                 335

Arg Ala Glu Gln Ala Ser Gln Glu Val Lys Asn Trp Met Thr Glu Thr
            340                 345                 350

Leu Leu Val Gln Asn Ser Asn Pro Asp Cys Lys Thr Ile Leu Lys Ala
        355                 360                 365

Leu Gly Pro Ala Ala Thr Leu Glu Glu Met Met Thr Ala Cys Gln Gly
    370                 375                 380

Val Gly Gly Pro Gly His Lys Ala Arg Val Leu Met Gln Tyr Ile Lys
385                 390                 395                 400

Ala Asn Ser Lys Phe Ile Gly Ile Thr Glu Leu Lys Lys Leu Gly Gly
                405                 410                 415

Ser Asn Asp Ile Phe Asn Asn Phe Thr Val Ser Phe Trp Leu Arg Val
            420                 425                 430

Pro Lys Val Ser Ala Ser His Leu Glu Gln Tyr Leu Glu Ala Thr Asn
        435                 440                 445

Thr Lys Val Asp Lys Thr Val Ala Pro Ser Thr Cys Ser Lys Pro Met
    450                 455                 460

Cys Pro Pro Pro Glu Leu Leu Gly Gly Pro Ser Val Phe Ile Phe Pro
465                 470                 475                 480

Pro Lys Pro Lys Asp Thr Leu Met Ile Ser Arg Thr Pro Glu Val Thr
                485                 490                 495

Cys Val Val Val Asp Val Ser Gln Asp Asp Pro Glu Val Gln Phe Thr
            500                 505                 510

Trp Tyr Ile Asn Asn Glu Gln Val Arg Thr Ala Arg Pro Pro Leu Arg
        515                 520                 525

Glu Gln Gln Phe Asn Ser Thr Ile Arg Val Val Ser Thr Leu Pro Ile
    530                 535                 540

Ala His Gln Asp Trp Leu Arg Gly Lys Glu Phe Lys Cys Lys Val His
545                 550                 555                 560

Asn Lys Ala Leu Pro Ala Pro Ile Glu Lys Thr Ile Ser Lys Ala Arg
                565                 570                 575

Gly Gln Pro Leu Glu Pro Lys Val Tyr Thr Met Gly Pro Pro Arg Glu
            580                 585                 590

Glu Leu Ser Ser Arg Ser Val Ser Leu Thr Cys Met Ile Asn Gly Phe
        595                 600                 605

Tyr Pro Ser Asp Ile Ser Val Glu Trp Glu Lys Asn Gly Lys Ala Glu
    610                 615                 620

Asp Asn Tyr Lys Thr Thr Pro Thr Val Leu Asp Ser Asp Gly Ser Tyr
625                 630                 635                 640

Phe Leu Tyr Ser Lys Leu Ser Val Pro Thr Ser Glu Trp Gln Arg Gly
                645                 650                 655

Asp Val Phe Thr Cys Ser Val Met His Glu Ala Leu His Asn His Tyr
            660                 665                 670
```

Thr Gln Lys Ser Ile Ser His Ser Pro Gly Lys
         675                 680

<210> SEQ ID NO 14
<211> LENGTH: 2068
<212> TYPE: DNA
<213> ORGANISM: Artificial Sequence
<220> FEATURE:
<223> OTHER INFORMATION: mspd1-14del-p24-Fc

<400> SEQUENCE: 14

| | | | | | |
|---|---|---|---|---|---|
| atgtgggtcc | ggcaggtacc | ctggtcattc | acttgggctg | tgctgcagtt | gagctggcaa | 60 |
| tcagggtggc | ttctagcctg | gctcacagtg | tcagagggag | caaatgccac | cttcacctgc | 120 |
| agcttgtcca | actggtcgga | ggatcttatg | ctgaactgga | accgcctgag | tcccagcaac | 180 |
| cagactgaaa | acaggccgc | cttctgtaat | ggtttgagcc | aacccgtcca | ggatgcccgc | 240 |
| ttccagatca | tacagctgcc | aacaggcat | gacttccaca | tgaacatcct | tgacacacgg | 300 |
| cgcaatgaca | gtggcatcta | cctctgtggg | gccatctccc | tgcacccaa | ggcaaaaatc | 360 |
| gaggagagcc | ctggagcaga | gctcgtggta | acagagaaa | tcctggagac | ctcaacaaga | 420 |
| tatcccagcc | cctcgcccaa | accagaaggc | cggtttcaac | cggaattccg | ggtggtggt | 480 |
| ggttcaggag | gaggacctat | agtgcaaaac | tccaggggc | aaatggtaca | tcagcccata | 540 |
| tcacctagaa | ctttaaatgc | atgggtaaaa | gtaatagaag | agaaggcttt | tagtccagaa | 600 |
| gtaatacccca | tgttttcagc | attatcagaa | ggagccaccc | acaagatttt | aaacaccatg | 660 |
| ctaaacacag | tggggggaca | tcaagcagcc | atgcaaatgt | taaagaaaac | catcaatgag | 720 |
| gaagctgcag | aatgggatag | attgcatcca | gtgcaggcag | ggccagttgc | accaggccag | 780 |
| atgagagaac | caaggggaag | tgacatagca | ggaactacta | gtaatcttca | ggagcaaata | 840 |
| ggatggatga | caaataatcc | acctatccca | gtaggagaaa | tctataaaag | atggataatc | 900 |
| ctggggttaa | ataaaatagt | aagaatgtat | agccctacca | gcattctgga | cataagacaa | 960 |
| ggaccaaagg | aaccctttag | agactatgta | gaccggttct | ataaaactct | aagagccgag | 1020 |
| caagcttcac | aagaggtaaa | aaattggatg | acagaaacct | tgttggtcca | aaattcgaac | 1080 |
| ccagattgta | agactatttt | aaaagcattg | ggaccagcag | ctacactaga | agaaatgatg | 1140 |
| acagcatgtc | agggagtggg | gggacctggc | cataaagcaa | gagttttgat | cctgatgcag | 1200 |
| tacatcaagg | ccaacagtaa | gttcatcgga | atcaccgagc | ttaagaagct | gggaggctca | 1260 |
| aacgacatat | tcaacaactt | cacagtgtcc | ttctggttgc | gggttcccaa | ggtctctgct | 1320 |
| agccacctcg | aacaataccct | ggaggccacc | aacaccaaag | tggacaagac | cgttgcgccc | 1380 |
| tcgacatgca | gcaagcccat | gtgcccaccc | cctgaactcc | tgggggggacc | gtctgtcttc | 1440 |
| atcttccccc | caaaacccaa | ggacaccctc | atgatctcac | gcacccccga | ggtcacatgc | 1500 |
| gtggtggtgg | acgtgagcca | ggatgacccc | gaggtgcagt | tcacatggta | cataaacaac | 1560 |
| gagcaggtgc | gcaccgcccg | gccgccgcta | cgggagcagc | agttcaacag | cacgatccgc | 1620 |
| gtggtcagca | ccctccccat | cgcgcaccag | gactggctga | ggggcaagga | gttcaagtgc | 1680 |
| aaagtccaca | acaaggcact | cccggccccc | atcgagaaaa | ccatctccaa | agccagaggg | 1740 |
| cagcccctgg | agccgaaggt | ctacaccatg | ggccctcccc | gggaggagct | gagcagcagg | 1800 |
| tcggtcagcc | tgacctgcat | gatcaacggc | ttctacccctt | ccgacatctc | ggtggagtgg | 1860 |
| gagaagaacg | ggaaggcaga | ggacaactac | aagaccacgc | cgaccgtgct | ggacagcgac | 1920 |
| ggctcctact | tcctctacag | caagctctca | gtgcccacga | gtgagtggca | gcggggcgac | 1980 |

```
gtcttcacct gctccgtgat gcacgaggcc ttgcacaacc actacacgca gaagtccatc    2040
tcccactctc ctggtaaata atctagag                                       2068

<210> SEQ ID NO 15
<211> LENGTH: 178
<212> TYPE: PRT
<213> ORGANISM: Artificial Sequence
<220> FEATURE:
<223> OTHER INFORMATION: mspd1-322mu

<400> SEQUENCE: 15

Met Trp Val Arg Gln Val Pro Trp Ser Phe Thr Trp Ala Val Leu Gln
1               5                   10                  15

Leu Ser Trp Gln Ser Gly Trp Leu Leu Glu Val Pro Asn Gly Pro Trp
            20                  25                  30

Arg Ser Leu Thr Phe Tyr Pro Ala Trp Leu Thr Val Ser Glu Gly Ala
        35                  40                  45

Asn Ala Thr Phe Thr Cys Ser Leu Ser Asn Trp Ser Glu Asp Leu Met
    50                  55                  60

Leu Asn Trp Asn Arg Leu Ser Pro Ser Asn Gln Thr Glu Lys Gln Ala
65                  70                  75                  80

Ala Phe Cys Asn Gly Leu Ser Gln Pro Val Gln Asp Ala Arg Phe Gln
                85                  90                  95

Ile Ile Gln Leu Pro Asn Arg His Asp Phe His Val Asn Ile Leu Asp
            100                 105                 110

Thr Arg Arg Asn Asp Ser Gly Ile Tyr Leu Cys Gly Ala Ile Ser Leu
        115                 120                 125

His Pro Lys Ala Lys Ile Glu Glu Ser Pro Gly Ala Glu Leu Val Val
    130                 135                 140

Thr Glu Arg Ile Leu Glu Thr Ser Thr Arg Tyr Pro Ser Pro Ser Pro
145                 150                 155                 160

Lys Pro Glu Gly Arg Phe Gln Pro Glu Phe Arg Gly Gly Gly Ser Gly
                165                 170                 175

Gly Gly

<210> SEQ ID NO 16
<211> LENGTH: 537
<212> TYPE: DNA
<213> ORGANISM: Artificial Sequence
<220> FEATURE:
<223> OTHER INFORMATION: mspd1-322mu

<400> SEQUENCE: 16
atgtgggtcc ggcaggtacc ctggtcattc acttgggctg tgctgcagtt gagctggcaa    60
tcagggtggc ttctagaggt ccccaatggg ccctggaggt ccctcacctt ctacccagcc   120
tggctcacag tgtcagaggg agcaaatgcc accttcacct gcagcttgtc caactggtcg   180
gaggatctta tgctgaactg gaaccgcctg agtcccagca accagactga aaaacaggcc   240
gccttctgta atggtttgag ccaacccgtc aggatgcccg cttccagat catacagctg   300 cccaacaggc atgacttcca cgtgaacatc cttgacacac ggcgcaatga cagtggcatc   360
tacctctgtg gggccatctc cctgcacccc aaggcaaaaa tcgaggagag ccctggagca   420
gagctcgtgg taacagagag aatcctggag acctcaacaa gatatcccag ccctcgccc    480 aaaccagaag gccggtttca accggaattc cggggtggtg gtggttcagg aggagga     537

<210> SEQ ID NO 17
```

<211> LENGTH: 697
<212> TYPE: PRT
<213> ORGANISM: Artificial Sequence
<220> FEATURE:
<223> OTHER INFORMATION: mspd1-322mu-p24-Fc

<400> SEQUENCE: 17

```
Met Trp Val Arg Gln Val Pro Trp Ser Phe Thr Trp Ala Val Leu Gln
1               5                   10                  15

Leu Ser Trp Gln Ser Gly Trp Leu Leu Glu Val Pro Asn Gly Pro Trp
            20                  25                  30

Arg Ser Leu Thr Phe Tyr Pro Ala Trp Leu Thr Val Ser Glu Gly Ala
        35                  40                  45

Asn Ala Thr Phe Thr Cys Ser Leu Ser Asn Trp Ser Glu Asp Leu Met
50                  55                  60

Leu Asn Trp Asn Arg Leu Ser Pro Ser Asn Gln Thr Glu Lys Gln Ala
65                  70                  75                  80

Ala Phe Cys Asn Gly Leu Ser Gln Pro Val Gln Asp Ala Arg Phe Gln
                85                  90                  95

Ile Ile Gln Leu Pro Asn Arg His Asp Phe His Val Asn Ile Leu Asp
            100                 105                 110

Thr Arg Arg Asn Asp Ser Gly Ile Tyr Leu Cys Gly Ala Ile Ser Leu
        115                 120                 125

His Pro Lys Ala Lys Ile Glu Glu Ser Pro Gly Ala Glu Leu Val Val
130                 135                 140

Thr Glu Arg Ile Leu Glu Thr Ser Thr Arg Tyr Pro Ser Pro Ser Pro
145                 150                 155                 160

Lys Pro Glu Gly Arg Phe Gln Pro Glu Phe Arg Gly Gly Gly Ser Gly
                165                 170                 175

Gly Gly Pro Ile Val Gln Asn Leu Gln Gly Gln Met Val His Gln Pro
            180                 185                 190

Ile Ser Pro Arg Thr Leu Asn Ala Trp Val Lys Val Ile Glu Glu Lys
        195                 200                 205

Ala Phe Ser Pro Glu Val Ile Pro Met Phe Ser Ala Leu Ser Glu Gly
210                 215                 220

Ala Thr Pro Gln Asp Leu Asn Thr Met Leu Asn Thr Val Gly Gly His
225                 230                 235                 240

Gln Ala Ala Met Gln Met Leu Lys Glu Thr Ile Asn Glu Glu Ala Ala
                245                 250                 255

Glu Trp Asp Arg Leu His Pro Val Gln Ala Gly Pro Val Ala Pro Gly
            260                 265                 270

Gln Met Arg Glu Pro Arg Gly Ser Asp Ile Ala Gly Thr Thr Ser Asn
        275                 280                 285

Leu Gln Glu Gln Ile Gly Trp Met Thr Asn Asn Pro Ile Pro Val
290                 295                 300

Gly Glu Ile Tyr Lys Arg Trp Ile Ile Leu Gly Leu Asn Lys Ile Val
305                 310                 315                 320

Arg Met Tyr Ser Pro Thr Ser Ile Leu Asp Ile Arg Gln Gly Pro Lys
                325                 330                 335

Glu Pro Phe Arg Asp Tyr Val Asp Arg Phe Tyr Lys Thr Leu Arg Ala
            340                 345                 350

Glu Gln Ala Ser Gln Glu Val Lys Asn Trp Met Thr Glu Thr Leu Leu
        355                 360                 365

Val Gln Asn Ser Asn Pro Asp Cys Lys Thr Ile Leu Lys Ala Leu Gly
370                 375                 380
```

```
Pro Ala Ala Thr Leu Glu Glu Met Met Thr Ala Cys Gln Gly Val Gly
385                 390                 395                 400

Gly Pro Gly His Lys Ala Arg Val Leu Met Gln Tyr Ile Lys Ala Asn
            405                 410                 415

Ser Lys Phe Ile Gly Ile Thr Glu Leu Lys Lys Leu Gly Gly Ser Asn
        420                 425                 430

Asp Ile Phe Asn Asn Phe Thr Val Ser Phe Trp Leu Arg Val Pro Lys
    435                 440                 445

Val Ser Ala Ser His Leu Glu Gln Tyr Leu Glu Ala Thr Asn Thr Lys
450                 455                 460

Val Asp Lys Thr Val Ala Pro Ser Thr Cys Ser Lys Pro Met Cys Pro
465                 470                 475                 480

Pro Pro Glu Leu Leu Gly Gly Pro Ser Val Phe Ile Phe Pro Pro Lys
            485                 490                 495

Pro Lys Asp Thr Leu Met Ile Ser Arg Thr Pro Glu Val Thr Cys Val
        500                 505                 510

Val Val Asp Val Ser Gln Asp Pro Glu Val Gln Phe Thr Trp Tyr
    515                 520                 525

Ile Asn Asn Glu Gln Val Arg Thr Ala Arg Pro Leu Arg Glu Gln
530                 535                 540

Gln Phe Asn Ser Thr Ile Arg Val Val Ser Thr Leu Pro Ile Ala His
545                 550                 555                 560

Gln Asp Trp Leu Arg Gly Lys Glu Phe Lys Cys Lys Val His Asn Lys
            565                 570                 575

Ala Leu Pro Ala Pro Ile Glu Lys Thr Ile Ser Lys Ala Arg Gly Gln
        580                 585                 590

Pro Leu Glu Pro Lys Val Tyr Thr Met Gly Pro Pro Arg Glu Glu Leu
    595                 600                 605

Ser Ser Arg Ser Val Ser Leu Thr Cys Met Ile Asn Gly Phe Tyr Pro
610                 615                 620

Ser Asp Ile Ser Val Glu Trp Glu Lys Asn Gly Lys Ala Glu Asp Asn
625                 630                 635                 640

Tyr Lys Thr Thr Pro Thr Val Leu Asp Ser Asp Gly Ser Tyr Phe Leu
            645                 650                 655

Tyr Ser Lys Leu Ser Val Pro Thr Ser Glu Trp Gln Arg Gly Asp Val
        660                 665                 670

Phe Thr Cys Ser Val Met His Glu Ala Leu His Asn His Tyr Thr Gln
    675                 680                 685

Lys Ser Ile Ser His Ser Pro Gly Lys
    690                 695

<210> SEQ ID NO 18
<211> LENGTH: 2110
<212> TYPE: DNA
<213> ORGANISM: Artificial Sequence
<220> FEATURE:
<223> OTHER INFORMATION: mspd1-322mu-p24-Fc

<400> SEQUENCE: 18
atgtgggtcc ggcaggtacc ctggtcattc acttgggctg tgctgcagtt gagctggcaa      60
tcagggtggc ttctagaggt cccccaatggg ccctggaggt ccctcacctt ctacccagcc    120
tggctcacag tgtcagaggg agcaaatgcc accttcacct gcagcttgtc caactggtcg    180
gaggatctta tgctgaactg gaaccgcctg agtcccagca accagactga aaaacaggcc    240
```

```
gccttctgta atggtttgag ccaacccgtc caggatgccc gcttccagat catacagctg    300
cccaacaggc atgacttcca cgtgaacatc cttgacacac ggcgcaatga cagtggcatc    360
tacctctgtg gggccatctc cctgcacccc aaggcaaaaa tcgaggagag ccctggagca    420
gagctcgtgg taacagagag aatcctggag acctcaacaa gatatcccag ccctcgccc     480
aaaccagaag gccggtttca accggaattc cggggtggtg gtggttcagg aggaggacct    540
atagtgcaaa acctccaggg gcaaatggta catcagccca tatcacctag aactttaaat    600
gcatgggtaa aagtaataga agagaaggct tttagtccag aagtaatacc catgttttca    660
gcattatcag aaggagccac cccacaagat ttaaacacca tgctaaacac agtggggggga   720
catcaagcag ccatgcaaat gttaaaagaa accatcaatg aggaagctgc agaatgggat    780
agattgcatc cagtgcaggc agggccagtt gcaccaggcc agatgagaga accaaggggga   840
agtgacatag caggaactac tagtaatctt caggagcaaa taggatggat gacaaataat    900
ccacctatcc cagtaggaga aatctataaa agatggataa tcctgggttt aaataaaata    960
gtaagaatgt atagccctac cagcattctg gacataagac aaggaccaaa ggaacccttt   1020
agagactatg tagaccggtt ctataaaact ctaagagccg agcaagcttc acaagaggta   1080
aaaaattgga tgacagaaac cttgttggtc caaaattcga acccagattg taagactatt   1140
ttaaaagcat tgggaccagc agctacacta gaagaaatga tgacagcatg tcagggagtg   1200
gggggacctg gccataaagc aagagttttg atcctgatgc agtacatcaa ggccaacagt   1260
aagttcatcg gaatcaccga gcttaagaag ctgggaggct caaacgacat attcaacaac   1320
ttcacagtgt ccttctggtt gcgggttccc aaggtctctg ctagccacct cgaacaatac   1380
ctggaggcca ccaacaccaa agtggacaag accgttgcgc cctcgacatg cagcaagccc   1440
atgtgcccac cccctgaact cctgggggga ccgtctgtct tcatcttccc cccaaaaccc   1500
aaggacaccc tcatgatctc acgcaccccc gaggtcacat gcgtggtggt ggacgtgagc   1560
caggatgacc ccgaggtgca gttcacatgg tacataaaca cgagcaggt gcgcaccgcc    1620
cggccgccgc tacgggagca gcagttcaac agcacgatcc gcgtggtcag caccctcccc   1680
atcgcgcacc aggactggct gaggggcaag gagttcaagt gcaaagtcca acaaggca     1740
ctcccggccc ccatcgagaa aaccatctcc aaagccagag gcagcccct ggagccgaag    1800
gtctacacca tgggccctcc ccgggaggag ctgagcagca ggtcggtcag cctgacctgc   1860
atgatcaacg gcttctaccc ttccgacatc tcggtggagt gggagaagaa cgggaaggca   1920
gaggacaact acaagaccac gccgaccgtg ctggacagcg acggctccta cttcctctac   1980
agcaagctct cagtgcccac gagtgagtgg cagcggggcg acgtcttcac ctgctccgtg   2040
atgcacgagg ccttgcacaa ccactacacg cagaagtcca tctcccactc tcctggtaaa   2100
taatctagag                                                          2110
```

<210> SEQ ID NO 19
<211> LENGTH: 697
<212> TYPE: PRT
<213> ORGANISM: Artificial Sequence
<220> FEATURE:
<223> OTHER INFORMATION: mspd1-p24-Fc

<400> SEQUENCE: 19

Met Trp Val Arg Gln Val Pro Trp Ser Phe Thr Trp Ala Val Leu Gln
1               5                   10                  15

Leu Ser Trp Gln Ser Gly Trp Leu Leu Glu Val Pro Asn Gly Pro Trp
            20                  25                  30

```
Arg Ser Leu Thr Phe Tyr Pro Ala Trp Leu Thr Val Ser Glu Gly Ala
         35                  40                  45

Asn Ala Thr Phe Thr Cys Ser Leu Ser Asn Trp Ser Glu Asp Leu Met
 50                  55                  60

Leu Asn Trp Asn Arg Leu Ser Pro Ser Asn Gln Thr Glu Lys Gln Ala
 65                  70                  75                  80

Ala Phe Cys Asn Gly Leu Ser Gln Pro Val Gln Asp Ala Arg Phe Gln
                 85                  90                  95

Ile Ile Gln Leu Pro Asn Arg His Asp Phe His Met Asn Ile Leu Asp
            100                 105                 110

Thr Arg Arg Asn Asp Ser Gly Ile Tyr Leu Cys Gly Ala Ile Ser Leu
            115                 120                 125

His Pro Lys Ala Lys Ile Glu Glu Ser Pro Gly Ala Glu Leu Val Val
130                 135                 140

Thr Glu Arg Ile Leu Glu Thr Ser Thr Arg Tyr Pro Ser Pro Ser Pro
145                 150                 155                 160

Lys Pro Glu Gly Arg Phe Gln Pro Glu Phe Arg Gly Gly Gly Ser Gly
                165                 170                 175

Gly Gly Pro Ile Val Gln Asn Leu Gln Gly Gln Met Val His Gln Pro
            180                 185                 190

Ile Ser Pro Arg Thr Leu Asn Ala Trp Val Lys Val Ile Glu Glu Lys
            195                 200                 205

Ala Phe Ser Pro Glu Val Ile Pro Met Phe Ser Ala Leu Ser Glu Gly
            210                 215                 220

Ala Thr Pro Gln Asp Leu Asn Thr Met Leu Asn Thr Val Gly Gly His
225                 230                 235                 240

Gln Ala Ala Met Gln Met Leu Lys Glu Thr Ile Asn Glu Glu Ala Ala
                245                 250                 255

Glu Trp Asp Arg Leu His Pro Val Gln Ala Gly Pro Val Ala Pro Gly
            260                 265                 270

Gln Met Arg Glu Pro Arg Gly Ser Asp Ile Ala Gly Thr Thr Ser Asn
            275                 280                 285

Leu Gln Glu Gln Ile Gly Trp Met Thr Asn Asn Pro Pro Ile Pro Val
            290                 295                 300

Gly Glu Ile Tyr Lys Arg Trp Ile Ile Leu Gly Leu Asn Lys Ile Val
305                 310                 315                 320

Arg Met Tyr Ser Pro Thr Ser Ile Leu Asp Ile Arg Gln Gly Pro Lys
                325                 330                 335

Glu Pro Phe Arg Asp Tyr Val Asp Arg Phe Tyr Lys Thr Leu Arg Ala
            340                 345                 350

Glu Gln Ala Ser Gln Glu Val Lys Asn Trp Met Thr Glu Thr Leu Leu
            355                 360                 365

Val Gln Asn Ser Asn Pro Asp Cys Lys Thr Ile Leu Lys Ala Leu Gly
370                 375                 380

Pro Ala Ala Thr Leu Glu Glu Met Met Thr Ala Cys Gln Gly Val Gly
385                 390                 395                 400

Gly Pro Gly His Lys Ala Arg Val Leu Met Gln Tyr Ile Lys Ala Asn
                405                 410                 415

Ser Lys Phe Ile Gly Ile Thr Glu Leu Lys Lys Leu Gly Gly Ser Asn
            420                 425                 430

Asp Ile Phe Asn Asn Phe Thr Val Ser Phe Trp Leu Arg Val Pro Lys
            435                 440                 445
```

Val Ser Ala Ser His Leu Glu Gln Tyr Leu Glu Ala Thr Asn Thr Lys
450                 455                 460

Val Asp Lys Thr Val Ala Pro Ser Thr Cys Ser Lys Pro Met Cys Pro
465                 470                 475                 480

Pro Pro Glu Leu Leu Gly Gly Pro Ser Val Phe Ile Phe Pro Pro Lys
            485                 490                 495

Pro Lys Asp Thr Leu Met Ile Ser Arg Thr Pro Glu Val Thr Cys Val
            500                 505                 510

Val Val Asp Val Ser Gln Asp Asp Pro Glu Val Gln Phe Thr Trp Tyr
            515                 520                 525

Ile Asn Asn Glu Gln Val Arg Thr Ala Arg Pro Pro Leu Arg Glu Gln
530                 535                 540

Gln Phe Asn Ser Thr Ile Arg Val Val Ser Thr Leu Pro Ile Ala His
545                 550                 555                 560

Gln Asp Trp Leu Arg Gly Lys Glu Phe Lys Cys Lys Val His Asn Lys
            565                 570                 575

Ala Leu Pro Ala Pro Ile Glu Lys Thr Ile Ser Lys Ala Arg Gly Gln
            580                 585                 590

Pro Leu Glu Pro Lys Val Tyr Thr Met Gly Pro Pro Arg Glu Glu Leu
        595                 600                 605

Ser Ser Arg Ser Val Ser Leu Thr Cys Met Ile Asn Gly Phe Tyr Pro
    610                 615                 620

Ser Asp Ile Ser Val Glu Trp Glu Lys Asn Gly Lys Ala Glu Asp Asn
625                 630                 635                 640

Tyr Lys Thr Thr Pro Thr Val Leu Asp Ser Asp Gly Ser Tyr Phe Leu
            645                 650                 655

Tyr Ser Lys Leu Ser Val Pro Thr Ser Glu Trp Gln Arg Gly Asp Val
            660                 665                 670

Phe Thr Cys Ser Val Met His Glu Ala Leu His Asn His Tyr Thr Gln
        675                 680                 685

Lys Ser Ile Ser His Ser Pro Gly Lys
    690                 695

<210> SEQ ID NO 20
<211> LENGTH: 2110
<212> TYPE: DNA
<213> ORGANISM: Artificial Sequence
<220> FEATURE:
<223> OTHER INFORMATION: mspd1-p24-Fc

<400> SEQUENCE: 20
atgtgggtcc ggcaggtacc ctggtcattc acttgggctg tgctgcagtt gagctggcaa      60
tcagggtggc ttctagaggt ccccaatggg ccctggaggt ccctcacctt ctacccagcc     120
tggctcacag tgtcagaggg agcaaatgcc accttcacct gcagcttgtc caactggtcg     180
gaggatctta tgctgaactg gaaccgcctg agtcccagca accagactga aaaacaggcc     240
gccttctgta atggtttgag ccaacccgtc aggatgccc gcttccagat catacagctg     300
cccaacaggc atgacttcca catgaacatc cttgacacac ggcgcaatga cagtggcatc     360
tacctctgtg ggccatctc cctgcacccc aaggcaaaaa tcgaggagag ccctggagca     420
gagctcgtgg taacagagag aatcctggag acctcaacaa gatatcccag cccctcgccc     480
aaaccagaag gccggtttca accggaattc cggggtggtg gtggttcagg aggaggacct     540
atagtgcaaa acctccaggg gcaaatggta catcagccca tatcacctag aactttaaat     600
gcatgggtaa aagtaataga agagaaggct tttagtccag aagtaatacc catgttttca     660

```
gcattatcag aaggagccac cccacaagat ttaaacacca tgctaaacac agtgggggga    720
catcaagcag ccatgcaaat gttaaaagaa accatcaatg aggaagctgc agaatgggat    780
agattgcatc cagtgcaggc agggccagtt gcaccaggcc agatgagaga accaaggggga   840 agtgacatag caggaactac tagtaatctt caggagcaaa taggatggat gacaaataat    900
ccacctatcc cagtaggaga aatctataaa agatggataa tcctggggtt aaataaaata    960
gtaagaatgt atagccctac cagcattctg gacataagac aaggaccaaa ggaacccttt   1020
agagactatg tagaccggtt ctataaaact ctaagagccg agcaagcttc acaagaggta   1080
aaaaattgga tgacagaaac cttgttggtc caaaattcga acccagattg taagactatt   1140
ttaaaagcat tgggaccagc agctacacta gaagaaatga tgacagcatg tcagggagtg   1200
gggggacctg gccataaagc aagagttttg atcctgatgc agtacatcaa ggccaacagt   1260
aagttcatcg gaatcaccga gcttaagaag ctgggaggct caaacgacat attcaacaac   1320
ttcacagtgt ccttctggtt gcgggttccc aaggtctctg ctagccacct cgaacaatac   1380
ctggaggcca ccaacaccaa agtggacaag accgttgcgc cctcgacatg cagcaagccc   1440
atgtgcccac cccctgaact cctgggggga ccgtctgtct tcatcttccc cccaaaaccc   1500
aaggacaccc tcatgatctc acgcaccccc gaggtcacat gcgtggtggt ggacgtgagc   1560
caggatgacc ccgaggtgca gttcacatgg tacataaaca acgagcaggt gcgcaccgcc   1620
cggccgccgc tacgggagca gcagttcaac agcacgatcc gcgtggtcag caccctcccc   1680
atcgcgcacc aggactggct gaggggcaag gagttcaagt gcaaagtcca acaaggca    1740 ctcccggccc ccatcgagaa aaccatctcc aaagccagag ggcagcccct ggagccgaag   1800
gtctacacca tgggcctcc ccgggaggag ctgagcagca ggtcggtcag cctgacctgc   1860
atgatcaacg gcttctaccc ttccgacatc tcggtggagt gggagaagaa cgggaaggca   1920
gaggacaact acaagaccac gccgaccgtg ctggacagcg acggctccta cttcctctac   1980
agcaagctct cagtgcccac gagtgagtgg cagcggggcg acgtcttcac ctgctccgtg   2040
atgcacgagg ccttgcacaa ccactacacg cagaagtcca tctcccactc tcctggtaaa   2100
taatctagag                                                          2110
```

<210> SEQ ID NO 21
<211> LENGTH: 176
<212> TYPE: PRT
<213> ORGANISM: human
<220> FEATURE:
<223> OTHER INFORMATION: human spd1

<400> SEQUENCE: 21

```
Met Gln Ile Pro Gln Ala Pro Trp Pro Val Val Trp Ala Val Leu Gln
1               5                   10                  15

Leu Gly Trp Arg Pro Gly Trp Phe Leu Asp Ser Pro Asp Arg Pro Trp
            20                  25                  30

Asn Pro Pro Thr Phe Ser Pro Ala Leu Leu Val Val Thr Glu Gly Asp
        35                  40                  45

Asn Ala Thr Phe Thr Cys Ser Phe Ser Asn Thr Ser Glu Ser Phe Val
    50                  55                  60

Leu Asn Trp Tyr Arg Met Ser Pro Ser Asn Gln Thr Asp Lys Leu Ala
65                  70                  75                  80

Ala Phe Pro Glu Asp Arg Ser Gln Pro Gly Gln Asp Cys Arg Phe Arg
                85                  90                  95
```

Val Thr Gln Leu Pro Asn Gly Arg Asp Phe His Met Ser Val Val Arg
            100                 105                 110

Ala Arg Arg Asn Asp Ser Gly Thr Tyr Leu Cys Gly Ala Ile Ser Leu
        115                 120                 125

Ala Pro Lys Ala Gln Ile Lys Glu Ser Leu Arg Ala Glu Leu Arg Val
    130                 135                 140

Thr Glu Arg Arg Ala Glu Val Pro Thr Ala His Pro Ser Pro Ser Pro
145                 150                 155                 160

Arg Pro Ala Gly Gln Pro Glu Phe Arg Gly Gly Ser Gly Gly Gly
                165                 170                 175

<210> SEQ ID NO 22
<211> LENGTH: 531
<212> TYPE: DNA
<213> ORGANISM: human
<220> FEATURE:
<223> OTHER INFORMATION: human spd1

<400> SEQUENCE: 22
atgcagatcc cacaggcgcc ctggccagtc gtctgggcgg tgctacaact gggctggcgg     60
ccaggatggt tcttagactc cccagacagg ccctggaacc cccccacctt ctccccagcc    120
ctgctcgtgg tgaccgaagg ggacaacgcc accttcacct gcagcttctc caacacatcg    180
gagagcttcg tgctaaactg gtaccgcatg agccccagca accagacgga caagctggcc    240
gccttccccg aggaccgcag ccagcccggc caggactgcc gcttccgtgt cacacaactg    300
cccaacgggc gtgacttcca catgagcgtg gtcaggcccc ggcgcaatga cagcggcacc    360
tacctctgtg gggccatctc cctggccccc aagacgcaga tcaaagagag cctgcgggca    420
gagctcaggg tgacagagag aagggcagaa gtgcccacag cccacccag ccccctcaccc    480 aggccagccg gccagccgga attccggggt ggtggtggtt caggaggagg a             531

<210> SEQ ID NO 23
<211> LENGTH: 695
<212> TYPE: PRT
<213> ORGANISM: Artificial Sequence
<220> FEATURE:
<223> OTHER INFORMATION: hspd1-p24-Fc

<400> SEQUENCE: 23

Met Gln Ile Pro Gln Ala Pro Trp Pro Val Val Trp Ala Val Leu Gln
1               5                   10                  15

Leu Gly Trp Arg Pro Gly Trp Phe Leu Asp Ser Pro Asp Arg Pro Trp
            20                  25                  30

Asn Pro Pro Thr Phe Ser Pro Ala Leu Leu Val Val Thr Glu Gly Asp
        35                  40                  45

Asn Ala Thr Phe Thr Cys Ser Phe Ser Asn Thr Ser Glu Ser Phe Val
    50                  55                  60

Leu Asn Trp Tyr Arg Met Ser Pro Ser Asn Gln Thr Asp Lys Leu Ala
65                  70                  75                  80

Ala Phe Pro Glu Asp Arg Ser Gln Pro Gly Gln Asp Cys Arg Phe Arg
                85                  90                  95

Val Thr Gln Leu Pro Asn Gly Arg Asp Phe His Met Ser Val Val Arg
            100                 105                 110

Ala Arg Arg Asn Asp Ser Gly Thr Tyr Leu Cys Gly Ala Ile Ser Leu
        115                 120                 125

Ala Pro Lys Ala Gln Ile Lys Glu Ser Leu Arg Ala Glu Leu Arg Val
    130                 135                 140

```
Thr Glu Arg Arg Ala Glu Val Pro Thr Ala His Pro Ser Pro Ser Pro
145                 150                 155                 160

Arg Pro Ala Gly Gln Pro Glu Phe Arg Gly Gly Ser Gly Gly Gly
        165                 170                 175

Pro Ile Val Gln Asn Leu Gln Gly Gln Met Val His Gln Pro Ile Ser
            180                 185                 190

Pro Arg Thr Leu Asn Ala Trp Val Lys Val Ile Glu Glu Lys Ala Phe
        195                 200                 205

Ser Pro Glu Val Ile Pro Met Phe Ser Ala Leu Ser Glu Gly Ala Thr
        210                 215                 220

Pro Gln Asp Leu Asn Thr Met Leu Asn Thr Val Gly Gly His Gln Ala
225                 230                 235                 240

Ala Met Gln Met Leu Lys Glu Thr Ile Asn Glu Glu Ala Ala Glu Trp
            245                 250                 255

Asp Arg Leu His Pro Val Gln Ala Gly Pro Val Ala Pro Gly Gln Met
        260                 265                 270

Arg Glu Pro Arg Gly Ser Asp Ile Ala Gly Thr Thr Ser Asn Leu Gln
        275                 280                 285

Glu Gln Ile Gly Trp Met Thr Asn Asn Pro Pro Ile Pro Val Gly Glu
290                 295                 300

Ile Tyr Lys Arg Trp Ile Ile Leu Gly Leu Asn Lys Ile Val Arg Met
305                 310                 315                 320

Tyr Ser Pro Thr Ser Ile Leu Asp Ile Arg Gln Gly Pro Lys Glu Pro
            325                 330                 335

Phe Arg Asp Tyr Val Asp Arg Phe Tyr Lys Thr Leu Arg Ala Glu Gln
        340                 345                 350

Ala Ser Gln Glu Val Lys Asn Trp Met Thr Glu Thr Leu Leu Val Gln
        355                 360                 365

Asn Ser Asn Pro Asp Cys Lys Thr Ile Leu Lys Ala Leu Gly Pro Ala
370                 375                 380

Ala Thr Leu Glu Glu Met Met Thr Ala Cys Gln Gly Val Gly Gly Pro
385                 390                 395                 400

Gly His Lys Ala Arg Val Leu Met Gln Tyr Ile Lys Ala Asn Ser Lys
            405                 410                 415

Phe Ile Gly Ile Thr Glu Leu Lys Lys Leu Gly Gly Ser Asn Asp Ile
        420                 425                 430

Phe Asn Asn Phe Thr Val Ser Phe Trp Leu Arg Val Pro Lys Val Ser
        435                 440                 445

Ala Ser His Leu Glu Gln Tyr Leu Glu Ala Thr Asn Thr Lys Val Asp
        450                 455                 460

Lys Thr Val Ala Pro Ser Thr Cys Ser Lys Pro Met Cys Pro Pro
465                 470                 475                 480

Glu Leu Leu Gly Gly Pro Ser Val Phe Ile Phe Pro Pro Lys Pro Lys
            485                 490                 495

Asp Thr Leu Met Ile Ser Arg Thr Pro Glu Val Thr Cys Val Val Val
        500                 505                 510

Asp Val Ser Gln Asp Asp Pro Glu Val Gln Phe Thr Trp Tyr Ile Asn
        515                 520                 525

Asn Glu Gln Val Arg Thr Ala Arg Pro Pro Leu Arg Glu Gln Gln Phe
        530                 535                 540

Asn Ser Thr Ile Arg Val Val Ser Thr Leu Pro Ile Ala His Gln Asp
545                 550                 555                 560
```

```
Trp Leu Arg Gly Lys Glu Phe Lys Cys Lys Val His Asn Lys Ala Leu
            565                 570                 575
Pro Ala Pro Ile Glu Lys Thr Ile Ser Lys Ala Arg Gly Gln Pro Leu
        580                 585                 590
Glu Pro Lys Val Tyr Thr Met Gly Pro Pro Arg Glu Glu Leu Ser Ser
    595                 600                 605
Arg Ser Val Ser Leu Thr Cys Met Ile Asn Gly Phe Tyr Pro Ser Asp
610                 615                 620
Ile Ser Val Glu Trp Glu Lys Asn Gly Lys Ala Glu Asp Asn Tyr Lys
625                 630                 635                 640
Thr Thr Pro Thr Val Leu Asp Ser Asp Gly Ser Tyr Phe Leu Tyr Ser
            645                 650                 655
Lys Leu Ser Val Pro Thr Ser Glu Trp Gln Arg Gly Asp Val Phe Thr
        660                 665                 670
Cys Ser Val Met His Glu Ala Leu His Asn His Tyr Thr Gln Lys Ser
    675                 680                 685
Ile Ser His Ser Pro Gly Lys
    690                 695

<210> SEQ ID NO 24
<211> LENGTH: 2104
<212> TYPE: DNA
<213> ORGANISM: Artificial Sequence
<220> FEATURE:
<223> OTHER INFORMATION: hspd1-p24-Fc

<400> SEQUENCE: 24
atgcagatcc acaggcgcc ctggccagtc gtctgggcgg tgctacaact gggctggcgg      60
ccaggatggt tcttagactc cccagacagg ccctggaacc ccccaccctt ctccccagcc    120
ctgctcgtgg tgaccgaagg ggacaacgcc accttcacct gcagcttctc caacacatcg    180
gagagcttcg tgctaaactg gtaccgcatg agccccagca accagacgga caagctggcc    240
gccttccccg aggaccgcag ccagcccggc caggactgcc gcttccgtgt cacacaactg    300
cccaacgggc gtgacttcca catgagcgtg gtcagggccc ggcgcaatga cagcggcacc    360
tacctctgtg gggccatctc cctggccccc aagacgcaga tcaaagagag cctgcgggca    420
gagctcaggg tgacagagag aagggcagaa gtgcccacag cccaccccag ccctcacccc    480
aggccagccg gccagccgga attccggggt ggtggtggtt caggaggagg acctatagtg    540
caaaacctcc aggggcaaat ggtacatcag cccatatcac ctagaacttt aaatgcatgg    600
gtaaaagtaa tagaagagaa gcttttagt ccagaagtaa tacccatgtt ttcagcatta    660
tcagaaggag ccaccccaca agatttaaac accatgctaa acacagtggg gggacatcaa    720
gcagccatgc aaatgttaaa agaaaccatc aatgaggaag ctgcagaatg ggatagattg    780
catccagtgc aggcagggcc agttgcacca ggccagatga gaaaccaag ggaagtgac     840 atagcaggaa ctactagtaa tcttcaggag caaataggat ggatgacaaa taatccacct    900
atcccagtag gagaaatcta taaaagatgg ataatcctgg ggttaaataa aatagtaaga    960
atgtatagcc taccagcat tctggacata agacaaggac caaaggaacc ctttagagac   1020
tatgtagacc ggttctataa aactctaaga gccgagcaag cttcacaaga ggtaaaaaat   1080
tggatgacag aaaccttgtt ggtccaaaat tcgaacccag attgtaagac tattttaaaa   1140
gcattgggac cagcagctac actagaagaa atgatgacag catgtcaggg agtgggggga   1200
cctggccata agcaagagt tttgatcctg atgcagtaca tcaaggccaa cagtaagttc   1260
```

```
atcggaatca ccgagcttaa gaagctggga ggctcaaacg acatattcaa caacttcaca    1320
gtgtccttct ggttgcgggt tcccaaggtc tctgctagcc acctcgaaca ataccctggag   1380 gccaccaaca ccaaagtgga caagaccgtt gcgccctcga catgcagcaa gcccatgtgc    1440 ccacccctg aactcctggg gggaccgtct gtcttcatct ccccccaaa acccaaggac      1500 accctcatga tctcacgcac ccccgaggtc acatgcgtgg tggtggacgt gagccaggat   1560
gaccccgagg tgcagttcac atggtacata aacaacgagc aggtgcgcac cgcccggccg   1620
ccgctacggg agcagcagtt caacagcacg atccgcgtgg tcagcaccct ccccatcgcg   1680
caccaggact ggctgagggg caaggagttc aagtgcaaag tccacaacaa ggcactcccg   1740
gcccccatcg agaaaaccat ctccaaagcc agagggcagc cctggagcc gaaggtctac    1800 accatgggcc ctccccggga ggagctgagc agcaggtcgg tcagcctgac ctgcatgatc   1860
aacggcttct acccttccga catctcggtg gagtgggaga gaacgggaa ggcagaggac    1920 aactacaaga ccacgccgac cgtgctggac agcgacggct cctacttcct ctacagcaag   1980
ctctcagtgc ccacgagtga gtggcagcgg ggcgacgtct tcacctgctc cgtgatgcac   2040
gaggccttgc acaaccacta cacgcagaag tccatctccc actctcctgg taaataatct   2100
agag                                                                2104
```

<210> SEQ ID NO 25
<211> LENGTH: 162
<212> TYPE: PRT
<213> ORGANISM: Artificial Sequence
<220> FEATURE:
<223> OTHER INFORMATION: hspd1-14del

<400> SEQUENCE: 25

```
Met Gln Ile Pro Gln Ala Pro Trp Pro Val Val Trp Ala Val Leu Gln
 1               5                  10                  15

Leu Gly Trp Arg Pro Gly Trp Phe Leu Ala Leu Leu Val Val Thr Glu
            20                  25                  30

Gly Asp Asn Ala Thr Phe Thr Cys Ser Phe Ser Asn Thr Ser Glu Ser
        35                  40                  45

Phe Val Leu Asn Trp Tyr Arg Met Ser Pro Ser Asn Gln Thr Asp Lys
    50                  55                  60

Leu Ala Ala Phe Pro Glu Asp Arg Ser Gln Pro Gly Gln Asp Cys Arg
65                  70                  75                  80

Phe Arg Val Thr Gln Leu Pro Asn Gly Arg Asp Phe His Met Ser Val
                85                  90                  95

Val Arg Ala Arg Arg Asn Asp Ser Gly Thr Tyr Leu Cys Gly Ala Ile
            100                 105                 110

Ser Leu Ala Pro Lys Ala Gln Ile Lys Glu Ser Leu Arg Ala Glu Leu
        115                 120                 125

Arg Val Thr Glu Arg Arg Ala Glu Val Pro Thr Ala His Pro Ser Pro
    130                 135                 140

Ser Pro Arg Pro Ala Gly Gln Pro Glu Phe Arg Gly Gly Gly Ser Gly
145                 150                 155                 160

Gly Gly
```

<210> SEQ ID NO 26
<211> LENGTH: 489
<212> TYPE: PRT
<213> ORGANISM: Artificial Sequence
<220> FEATURE:
<223> OTHER INFORMATION: hspd1-14del

<400> SEQUENCE: 26

Ala Thr Gly Cys Ala Gly Ala Thr Cys Cys Cys Ala Cys Ala Gly Gly
1               5                   10                  15

Cys Gly Cys Cys Cys Thr Gly Gly Cys Cys Ala Gly Thr Cys Gly Thr
            20                  25                  30

Cys Thr Gly Gly Gly Cys Gly Gly Thr Gly Cys Thr Ala Cys Ala Ala
        35                  40                  45

Cys Thr Gly Gly Gly Cys Thr Gly Gly Cys Gly Gly Cys Cys Ala Gly
    50                  55                  60

Gly Ala Thr Gly Gly Thr Thr Cys Thr Thr Ala Gly Cys Cys Cys Thr
65                  70                  75                  80

Gly Cys Thr Cys Gly Thr Gly Gly Thr Gly Ala Cys Cys Gly Ala Ala
                85                  90                  95

Gly Gly Gly Gly Ala Cys Ala Ala Cys Gly Cys Cys Ala Cys Cys Thr
            100                 105                 110

Thr Cys Ala Cys Cys Thr Gly Cys Ala Gly Cys Thr Thr Cys Thr Cys
        115                 120                 125

Cys Ala Ala Cys Ala Cys Ala Thr Cys Gly Gly Ala Gly Ala Gly Cys
    130                 135                 140

Thr Thr Cys Gly Thr Gly Cys Thr Ala Ala Ala Cys Thr Gly Gly Thr
145                 150                 155                 160

Ala Cys Cys Gly Cys Ala Thr Gly Ala Gly Cys Cys Cys Cys Ala Gly
                165                 170                 175

Cys Ala Ala Cys Cys Ala Gly Ala Cys Gly Gly Ala Cys Ala Ala Gly
            180                 185                 190

Cys Thr Gly Gly Cys Cys Gly Cys Cys Thr Thr Cys Cys Cys Cys Gly
        195                 200                 205

Ala Gly Gly Ala Cys Cys Gly Cys Ala Gly Cys Cys Ala Gly Cys Cys
    210                 215                 220

Cys Gly Gly Cys Cys Ala Gly Gly Ala Cys Thr Gly Cys Cys Gly Cys
225                 230                 235                 240

Thr Thr Cys Cys Gly Thr Gly Thr Cys Ala Cys Ala Cys Ala Ala Cys
                245                 250                 255

Thr Gly Cys Cys Cys Ala Ala Cys Gly Gly Gly Cys Gly Thr Gly Ala
            260                 265                 270

Cys Thr Thr Cys Cys Ala Cys Ala Thr Gly Ala Gly Cys Gly Thr Gly
        275                 280                 285

Gly Thr Cys Ala Gly Gly Gly Cys Cys Cys Gly Gly Cys Gly Cys Ala
    290                 295                 300

Ala Thr Gly Ala Cys Ala Gly Cys Gly Gly Cys Ala Cys Cys Thr Ala
305                 310                 315                 320

Cys Cys Thr Cys Thr Gly Thr Gly Gly Gly Gly Cys Cys Ala Thr Cys
                325                 330                 335

Thr Cys Cys Cys Thr Gly Gly Cys Cys Cys Cys Cys Ala Ala Gly Ala
            340                 345                 350

Cys Gly Cys Ala Gly Ala Thr Cys Ala Ala Ala Gly Ala Gly Ala Gly
        355                 360                 365

Cys Cys Thr Gly Cys Gly Gly Gly Cys Ala Gly Ala Gly Cys Thr Cys
    370                 375                 380

Ala Gly Gly Gly Thr Gly Ala Cys Ala Gly Ala Gly Ala Gly Ala Ala
385                 390                 395                 400

Gly Gly Gly Cys Ala Gly Ala Ala Gly Thr Gly Cys Cys Cys Ala Cys

```
                        405                 410                 415
Ala Gly Cys Cys Cys Ala Cys Cys Cys Ala Gly Cys Cys Cys Cys
                420                 425                 430

Thr Cys Ala Cys Cys Ala Gly Gly Cys Cys Ala Gly Cys Cys Gly
            435                 440                 445

Gly Cys Cys Ala Gly Cys Cys Gly Ala Ala Thr Thr Cys Cys Gly
        450                 455                 460

Gly Gly Gly Thr Gly Gly Thr Gly Gly Thr Gly Gly Thr Thr Cys Ala
    465                 470                 475                 480

Gly Gly Ala Gly Gly Ala Gly Gly Ala
                485

<210> SEQ ID NO 27
<211> LENGTH: 681
<212> TYPE: PRT
<213> ORGANISM: Artificial Sequence
<220> FEATURE:
<223> OTHER INFORMATION: hspd1-14del-p24-Fc

<400> SEQUENCE: 27

Met Gln Ile Pro Gln Ala Pro Trp Pro Val Val Trp Ala Val Leu Gln
1               5                   10                  15

Leu Gly Trp Arg Pro Gly Trp Phe Leu Ala Leu Leu Val Val Thr Glu
            20                  25                  30

Gly Asp Asn Ala Thr Phe Thr Cys Ser Phe Ser Asn Thr Ser Glu Ser
        35                  40                  45

Phe Val Leu Asn Trp Tyr Arg Met Ser Pro Ser Asn Gln Thr Asp Lys
    50                  55                  60

Leu Ala Ala Phe Pro Glu Asp Arg Ser Gln Pro Gly Gln Asp Cys Arg
65                  70                  75                  80

Phe Arg Val Thr Gln Leu Pro Asn Gly Arg Asp Phe His Met Ser Val
                85                  90                  95

Val Arg Ala Arg Arg Asn Asp Ser Gly Thr Tyr Leu Cys Gly Ala Ile
            100                 105                 110

Ser Leu Ala Pro Lys Ala Gln Ile Lys Glu Ser Leu Arg Ala Glu Leu
        115                 120                 125

Arg Val Thr Glu Arg Arg Ala Glu Val Pro Thr Ala His Pro Ser Pro
    130                 135                 140

Ser Pro Arg Pro Ala Gly Gln Pro Glu Phe Arg Gly Gly Gly Ser Gly
145                 150                 155                 160

Gly Gly Pro Ile Val Gln Asn Leu Gln Gly Gln Met Val His Gln Pro
                165                 170                 175

Ile Ser Pro Arg Thr Leu Asn Ala Trp Val Lys Val Ile Glu Glu Lys
            180                 185                 190

Ala Phe Ser Pro Glu Val Ile Pro Met Phe Ser Ala Leu Ser Glu Gly
        195                 200                 205

Ala Thr Pro Gln Asp Leu Asn Thr Met Leu Asn Thr Val Gly Gly His
    210                 215                 220

Gln Ala Ala Met Gln Met Leu Lys Glu Thr Ile Asn Glu Glu Ala Ala
225                 230                 235                 240

Glu Trp Asp Arg Leu His Pro Val Gln Ala Gly Pro Val Ala Pro Gly
                245                 250                 255

Gln Met Arg Glu Pro Arg Gly Ser Asp Ile Ala Gly Thr Thr Ser Asn
            260                 265                 270

Leu Gln Glu Gln Ile Gly Trp Met Thr Asn Asn Pro Pro Ile Pro Val
```

```
            275                 280                 285
Gly Glu Ile Tyr Lys Arg Trp Ile Ile Leu Gly Leu Asn Lys Ile Val
290                 295                 300

Arg Met Tyr Ser Pro Thr Ser Ile Leu Asp Ile Arg Gln Gly Pro Lys
305                 310                 315                 320

Glu Pro Phe Arg Asp Tyr Val Asp Arg Phe Tyr Lys Thr Leu Arg Ala
            325                 330                 335

Glu Gln Ala Ser Gln Glu Val Lys Asn Trp Met Thr Glu Thr Leu Leu
        340                 345                 350

Val Gln Asn Ser Asn Pro Asp Cys Lys Thr Ile Leu Lys Ala Leu Gly
    355                 360                 365

Pro Ala Ala Thr Leu Glu Glu Met Met Thr Ala Cys Gln Gly Val Gly
370                 375                 380

Gly Pro Gly His Lys Ala Arg Val Leu Met Gln Tyr Ile Lys Ala Asn
385                 390                 395                 400

Ser Lys Phe Ile Gly Ile Thr Glu Leu Lys Lys Leu Gly Gly Ser Asn
            405                 410                 415

Asp Ile Phe Asn Asn Phe Thr Val Ser Phe Trp Leu Arg Val Pro Lys
        420                 425                 430

Val Ser Ala Ser His Leu Glu Gln Tyr Leu Glu Ala Thr Asn Thr Lys
    435                 440                 445

Val Asp Lys Thr Val Ala Pro Ser Thr Cys Ser Lys Pro Met Cys Pro
450                 455                 460

Pro Pro Glu Leu Leu Gly Gly Pro Ser Val Phe Ile Phe Pro Pro Lys
465                 470                 475                 480

Pro Lys Asp Thr Leu Met Ile Ser Arg Thr Pro Glu Val Thr Cys Val
            485                 490                 495

Val Val Asp Val Ser Gln Asp Asp Pro Glu Val Gln Phe Thr Trp Tyr
        500                 505                 510

Ile Asn Asn Glu Gln Val Arg Thr Ala Arg Pro Pro Leu Arg Glu Gln
    515                 520                 525

Gln Phe Asn Ser Thr Ile Arg Val Val Ser Thr Leu Pro Ile Ala His
530                 535                 540

Gln Asp Trp Leu Arg Gly Lys Glu Phe Lys Cys Lys Val His Asn Lys
545                 550                 555                 560

Ala Leu Pro Ala Pro Ile Glu Lys Thr Ile Ser Lys Ala Arg Gly Gln
            565                 570                 575

Pro Leu Glu Pro Lys Val Tyr Thr Met Gly Pro Pro Arg Glu Glu Leu
        580                 585                 590

Ser Ser Arg Ser Val Ser Leu Thr Cys Met Ile Asn Gly Phe Tyr Pro
    595                 600                 605

Ser Asp Ile Ser Val Glu Trp Glu Lys Asn Gly Lys Ala Glu Asp Asn
610                 615                 620

Tyr Lys Thr Thr Pro Thr Val Leu Asp Ser Asp Gly Ser Tyr Phe Leu
625                 630                 635                 640

Tyr Ser Lys Leu Ser Val Pro Thr Ser Glu Trp Gln Arg Gly Asp Val
            645                 650                 655

Phe Thr Cys Ser Val Met His Glu Ala Leu His Asn His Tyr Thr Gln
        660                 665                 670

Lys Ser Ile Ser His Ser Pro Gly Lys
    675                 680

<210> SEQ ID NO 28
```

<211> LENGTH: 2062
<212> TYPE: DNA
<213> ORGANISM: Artificial Sequence
<220> FEATURE:
<223> OTHER INFORMATION: hspd1-14del-p24-Fc

<400> SEQUENCE: 28

| | | | | | |
|---|---|---|---|---|---|
| atgcagatcc | cacaggcgcc | ctggccagtc | gtctgggcgg | tgctacaact | gggctggcgg | 60 |
| ccaggatggt | tcttagccct | gctcgtggtg | accgaagggg | acaacgccac | cttcacctgc | 120 |
| agcttctcca | acacatcgga | gagcttcgtg | ctaaactggt | accgcatgag | ccccagcaac | 180 |
| cagacggaca | agctggccgc | cttccccgag | gaccgcagcc | agcccggcca | ggactgccgc | 240 |
| ttccgtgtca | cacaactgcc | caacgggcgt | gacttccaca | tgagcgtggt | cagggcccgg | 300 |
| cgcaatgaca | gcggcaccta | cctctgtggg | gccatctccc | tggcccccaa | gacgcagatc | 360 |
| aaagagagcc | tgcgggcaga | gctcagggtg | acagagagaa | gggcagaagt | gcccacagcc | 420 |
| cacccccagcc | cctcacccag | gccagccggc | cagccggaat | tccggggtgg | tggtggttca | 480 |
| ggaggaggac | ctatagtgca | aaacctccag | gggcaaatgg | tacatcagcc | catatccacct | 540 |
| agaactttaa | atgcatgggt | aaaagtaata | gaagagaagg | cttttagtcc | agaagtaata | 600 |
| cccatgtttt | cagcattatc | agaaggagcc | accccacaa | atttaaacac | catgctaaac | 660 |
| acagtggggg | gacatcaagc | agccatgcaa | atgttaaaag | aaaccatcaa | tgaggaagct | 720 |
| gcagaatggg | atagattgca | tccagtgcag | gcagggccag | ttgcaccagg | ccagatgaga | 780 |
| gaaccaaggg | gaagtgacat | agcaggaact | actagtaatc | ttcaggagca | aataggatgg | 840 |
| atgacaaata | atccacctat | cccagtagga | gaaatctata | aaagatggat | aatcctgggg | 900 |
| ttaaataaaa | tagtaagaat | gtatagccct | accagcattc | tggacataag | acaaggacca | 960 |
| aaggaaccct | ttagagacta | tgtagaccgg | ttctataaaa | ctctaagagc | cgagcaagct | 1020 |
| tcacaagagg | taaaaaattg | gatgacagaa | accttgttgg | tccaaaattc | gaacccagat | 1080 |
| tgtaagacta | ttttaaaagc | attgggacca | gcagctacac | tagaagaaat | gatgacagca | 1140 |
| tgtcagggag | tggggggacc | tggccataaa | gcaagagttt | tgatcctgat | gcagtacatc | 1200 |
| aaggccaaca | gtaagttcat | cggaatcacc | gagcttaaga | agctgggagg | ctcaaacgac | 1260 |
| atattcaaca | acttcacagt | gtccttctgg | ttgcgggttc | ccaaggtctc | tgctagccac | 1320 |
| ctcgaacaat | acctggaggc | caccaacacc | aaagtggaca | agaccgttgc | gccctcgaca | 1380 |
| tgcagcaagc | ccatgtgccc | accccctgaa | ctcctggggg | gaccgtctgt | cttcatcttc | 1440 |
| cccccaaaac | ccaaggacac | cctcatgatc | tcacgcaccc | cgaggtcac | atgcgtggtg | 1500 |
| gtggacgtga | gccaggatga | ccccgaggtg | cagttcacat | ggtacataaa | caacgagcag | 1560 |
| gtgcgcaccg | cccggccgcc | gctacgggag | cagcagttca | acagcacgat | ccgcgtggtc | 1620 |
| agcaccctcc | ccatcgcgca | ccaggactgg | ctgaggggca | aggagttcaa | gtgcaaagtc | 1680 |
| cacaacaagg | cactcccggc | cccatcgag | aaaaccatct | ccaaagccag | agggcagccc | 1740 |
| ctggagccga | aggtctacac | catgggccct | cccgggagg | agctgagcag | caggtcggtc | 1800 |
| agcctgacct | gcatgatcaa | cggcttctac | ccttccgaca | tctcggtgga | gtgggagaag | 1860 |
| aacgggaagg | cagaggacaa | ctacaagacc | acgccgaccg | tgctggacag | cgacggctcc | 1920 |
| tacttcctct | acagcaagct | ctcagtgccc | acgagtgagt | ggcagcgggg | cgacgtcttc | 1980 |
| acctgctccg | tgatgcacga | ggccttgcac | aaccactaca | cgcagaagtc | catctcccac | 2040 |
| tctcctggta | ataatctag | ag | | | | 2062 |

```
<210> SEQ ID NO 29
<211> LENGTH: 7
<212> TYPE: PRT
<213> ORGANISM: Artificial Sequence
<220> FEATURE:
<223> OTHER INFORMATION: linker sequence

<400> SEQUENCE: 29

Gly Gly Gly Ser Gly Gly Gly
1               5

<210> SEQ ID NO 30
<211> LENGTH: 27
<212> TYPE: PRT
<213> ORGANISM: Artificial Sequence
<220> FEATURE:
<223> OTHER INFORMATION: linker sequence

<400> SEQUENCE: 30

Gly Leu Tyr Gly Leu Tyr Gly Leu Tyr Gly Leu Tyr Gly Leu Tyr Gly
1               5                   10                  15
Leu Tyr Gly Leu Tyr Gly Leu Tyr Gly Leu Tyr
            20                  25

<210> SEQ ID NO 31
<211> LENGTH: 9
<212> TYPE: PRT
<213> ORGANISM: Artificial Sequence
<220> FEATURE:
<223> OTHER INFORMATION: linking sequence

<400> SEQUENCE: 31

Glu Glu Glu Glu Glu Glu Glu Glu Glu
1               5

<210> SEQ ID NO 32
<211> LENGTH: 27
<212> TYPE: PRT
<213> ORGANISM: Artificial Sequence
<220> FEATURE:
<223> OTHER INFORMATION: linker sequence

<400> SEQUENCE: 32

Ser Glu Arg Ser Glu Arg Ser Glu Arg Ser Glu Arg Ser Glu Arg Ser
1               5                   10                  15
Glu Arg Ser Glu Arg Ser Glu Arg Ser Glu Arg
            20                  25

<210> SEQ ID NO 33
<211> LENGTH: 9
<212> TYPE: PRT
<213> ORGANISM: Artificial Sequence
<220> FEATURE:
<223> OTHER INFORMATION: linking sequence

<400> SEQUENCE: 33

Gly Gly Gly Gly Gly Cys Pro Pro Cys
1               5

<210> SEQ ID NO 34
<211> LENGTH: 21
<212> TYPE: PRT
<213> ORGANISM: Artificial Sequence
<220> FEATURE:
<223> OTHER INFORMATION: linking sequence

<400> SEQUENCE: 34
```

```
Gly Leu Tyr Gly Leu Tyr Gly Leu Tyr Gly Leu Tyr Ser Glu Arg Ser
1               5                   10                  15

Glu Arg Ser Glu Arg
            20

<210> SEQ ID NO 35
<211> LENGTH: 13
<212> TYPE: PRT
<213> ORGANISM: Artificial Sequence
<220> FEATURE:
<223> OTHER INFORMATION: linking sequence

<400> SEQUENCE: 35

Ser Cys Val Pro Leu Met Arg Cys Gly Gly Cys Cys Asn
1               5                   10

<210> SEQ ID NO 36
<211> LENGTH: 14
<212> TYPE: PRT
<213> ORGANISM: Artificial Sequence
<220> FEATURE:
<223> OTHER INFORMATION: linking sequence

<400> SEQUENCE: 36

Pro Ser Cys Val Pro Leu Met Arg Cys Gly Gly Cys Cys Asn
1               5                   10

<210> SEQ ID NO 37
<211> LENGTH: 9
<212> TYPE: PRT
<213> ORGANISM: Artificial Sequence
<220> FEATURE:
<223> OTHER INFORMATION: linking sequence

<400> SEQUENCE: 37

Gly Asp Leu Ile Tyr Arg Asn Gln Lys
1               5

<210> SEQ ID NO 38
<211> LENGTH: 23
<212> TYPE: PRT
<213> ORGANISM: Artificial Sequence
<220> FEATURE:
<223> OTHER INFORMATION: linking sequence

<400> SEQUENCE: 38

Gly Gly Gly Gly Gly Gly Gly Gly Pro Ser Cys Val Pro Leu Met
1               5                   10                  15

Arg Cys Gly Gly Cys Cys Asn
            20

<210> SEQ ID NO 39
<211> LENGTH: 9
<212> TYPE: PRT
<213> ORGANISM: Artificial Sequence
<220> FEATURE:
<223> OTHER INFORMATION: linking sequence

<400> SEQUENCE: 39

Ala Met Gln Met Leu Lys Asp Thr Ile
1               5

<210> SEQ ID NO 40
<211> LENGTH: 20
<212> TYPE: PRT
```

```
<213> ORGANISM: Artificial Sequence
<220> FEATURE:
<223> OTHER INFORMATION: linking sequence

<400> SEQUENCE: 40

Thr Ser Asn Pro Pro Ile Pro Val Gly Asp Ile Tyr Lys Arg Trp Ile
1               5                   10                  15

Ile Leu Gly Leu
            20
```